United States Patent
Ito et al.

(10) Patent No.: US 7,585,574 B2
(45) Date of Patent: Sep. 8, 2009

(54) PYRENE DERIVATIVE AND ORGANIC ELECTROLUMINESCENCE DEVICE MAKING USE OF THE SAME

(75) Inventors: Mitsunori Ito, Chiba (JP); Mineyuki Kubota, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 11/926,813

(22) Filed: Oct. 29, 2007

(65) Prior Publication Data

US 2008/0124571 A1 May 29, 2008

Related U.S. Application Data

(63) Continuation of application No. PCT/JP2006/310194, filed on May 23, 2006.

(30) Foreign Application Priority Data

Jul. 6, 2005 (JP) ............................. 2005-197765

(51) Int. Cl.
*H01L 51/54* (2006.01)
*C07C 15/20* (2006.01)
*C07D 217/02* (2006.01)
*C07D 333/50* (2006.01)

(52) U.S. Cl. ...................... 428/690; 428/917; 313/504; 313/506; 546/285; 585/26; 585/27; 257/103; 257/E51.049

(58) Field of Classification Search ................ 428/690, 428/917; 313/504, 506; 257/40, E51.044; 546/173, 285; 585/26, 27; 549/43, 49
See application file for complete search history.

(56) References Cited

U.S. PATENT DOCUMENTS

| | | | | |
|---|---|---|---|---|
| 6,635,364 | B1 * | 10/2003 | Igarashi | ...................... 428/690 |
| 2004/0076852 | A1 | 4/2004 | Cheng et al. | |
| 2004/0232409 | A1 | 11/2004 | Igarashi et al. | |
| 2005/0048318 | A1 | 3/2005 | Suzuki et al. | |
| 2005/0064233 | A1 | 3/2005 | Matsuura et al. | |
| 2006/0154107 | A1 * | 7/2006 | Kubota et al. | ............... 428/690 |

FOREIGN PATENT DOCUMENTS

| | | |
|---|---|---|
| EP | 1 533 290 | 5/2005 |
| JP | 2002-329580 | 11/2002 |
| JP | 2004-075567 | 3/2004 |
| JP | 2004-139957 | 5/2004 |
| JP | 2004-535051 | 11/2004 |
| JP | 2005-206551 | 8/2005 |
| JP | 2006-176494 | 7/2006 |
| WO | WO 2004/018588 | 3/2004 |

* cited by examiner

*Primary Examiner*—D. Lawrence Tarazano
*Assistant Examiner*—Michael Wilson
(74) *Attorney, Agent, or Firm*—Oblon, Spivak, McClelland, Maier & Neustadt, P.C.

(57) ABSTRACT

Provided are a pyrene derivative of a specified structure and an organic electroluminescence device including an organic thin film layer formed of one or multiple layers including at least a light emitting layer, the organic thin film layer being interposed between a cathode and an anode, in which at least one layer of the organic thin film layer contains the pyrene derivative alone or as a component of mixture. Thus, there are provided an organic electroluminescence device capable of obtaining long-life blue light emission with high luminous efficiency and a novel pyrene derivative for realization thereof.

10 Claims, No Drawings

PYRENE DERIVATIVE AND ORGANIC ELECTROLUMINESCENCE DEVICE MAKING USE OF THE SAME

TECHNICAL FIELD

The present invention relates to an organic electroluminescence (hereinafter, which may sometimes be abbreviated as EL) device, in particular, an organic EL device which uses a pyrene derivative as a light emitting material, has a long lifetime and high luminous efficiency, and can be produced at a low cost.

BACKGROUND ART

An organic electroluminescence device (hereinafter, electroluminescence may sometimes be abbreviated as EL) is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Page 913, 1987, or the like), many studies have been conducted on organic EL devices using organic materials as the constituent materials. Tang et al. used tris(8-quinolinolato)aluminum for a light emitting layer and a triphenyldiamine derivative for a hole transporting layer. Advantages of the laminate structure are that the efficiency of hole injection into the light emitting layer can be increased, that the efficiency of forming exciton which are formed by blocking and recombining electrons injected from the cathode can be increased, and that exciton formed within the light emitting layer can be enclosed. As described above, for the structure of the organic EL device, a two-layered structure having a hole transporting (injecting) layer and an electron-transporting light emitting layer and a three-layered structure having a hole transporting (injecting) layer, a light emitting layer, and an electron-transporting (injecting) layer are well known. In order to increase the efficiency of recombination of injected holes and electrons in the devices of the laminate type, the structure of the device and the process for forming the device have been studied.

Further, as the light emitting material, chelate complexes such as tris(8-quinolinolato)aluminum complexes, coumarin derivatives, tetraphenylbutadiene derivatives, bisstyrylarylene derivatives, and oxadiazole derivatives are known. It is reported that light in the visible region ranging from blue light to red light can be obtained by using those light emitting materials, and development of a device exhibiting color images is expected (for example, Patent Documents 1 to 3).

In recent years, a large number of investigations have been conducted on the use of a phosphorescent compound as a light emitting material and the use of energy in a triplet state in EL light emission. A group of Princeton University has reported that an organic light emitting device using an iridium complex as a light emitting material shows high luminous efficiency (Non-patent Document 1). In addition to the organic electroluminescence device using a low molecular weight material as described above, an organic electroluminescence device using a conjugated polymer has been reported by a group of Cambridge University (Non-patent Document 2). In this report, light emission has been confirmed from a monolayer of polyphenylene vinylene (PPV) formed in a coating system.

Recent advances in organic electroluminescence device are remarkable, and characteristics of the organic electroluminescence device allow formation of a thin and lightweight light-emitting device with high luminance under application of a low voltage, wide range of emission wavelengths, and high-speed response, thereby suggesting the possibility of extensive uses.

In association with the significant progress of an organic light emitting device, performance requested of a light emitting material has been growing, and Patent Documents 4 and 5 each disclose a pyrene compound using fluorene as a linker. In addition, Patent Document 6 discloses a pyrene compound using a phenylene or biphenylene group as a linker, and Patent Document 7 discloses tripyrenylbenzene as a comparative example. However, each of the compounds has problems such as an insufficient half life and a poor color purity. Accordingly, a light emitting material from which an optical output with additionally high luminance or additionally high conversion efficiency can be obtained has been requested. In addition, a light emitting material which: takes durability against, for example, a change over time due to long-term use and deterioration due to, for example, an atmospheric gas containing oxygen or moisture, and application to a full-color display or the like into consideration; and emits blue, green, or red light with a high color purity, has been desired.

Patent Document 1: JP 08-239655 A
Patent Document 2: JP 07-183561 A
Patent Document 3: JP 03-200289 A
Patent Document 4: JP 2004-83481 A
Patent Document 5: JP 2004-43349 A
Patent Document 6: JP 2004-139957 A
Patent Document 7: JP 2003-347056 A
Non-patent Document 1: Nature, 395, 151 (1998)
Non-patent Document 2: Nature, 347, 539 (1990)

DISCLOSURE OF THE INVENTION

Problem to be solved by the Invention

The present invention has been made with a view to solving the above-mentioned problems of the conventional art, and an object of the present invention is to provide an organic EL device capable of emitting blue light with high luminous efficiency for a long time period by using a pyrene derivative as a light emitting material. Another object of the present invention is to enable such organic EL device to be produced easily at a relatively low cost.

Means for Solving the Problems

The inventors of the present invention have made extensive studies with a view to solving the above-mentioned problems. As a result, the inventors have found that the use of a pyrene derivative represented by the following general formula (1) or (2) as a light emitting material enables the production of an organic EL device having high luminous efficiency and a long lifetime.

That is, the present invention provides a pyrene derivative represented by the following general formula (1):

  (1)

where: X's each represent a substituted or unsubstituted pyrene residue; A's and B's each independently represent a hydrogen atom, a substituted or unsubstituted aromatic hydrocarbon group having 3 to 50 ring carbon atoms, a substituted or unsubstituted aromatic heterocyclic group having 1 to 50 ring carbon atoms, a substituted or unsubstituted alkyl or alkylene group having 1 to 50 carbon atoms, or a substituted or unsubstituted alkenyl or alkenylene group having 1 to 50 carbon atoms; Ar's represent at least any one of a substituted or unsubstituted aromatic hydrocarbon group having 3 to 50 ring carbon atoms and a substituted or unsubstituted aromatic heterocyclic group having 1 to 50 ring carbon atoms; Y's represent at least any one of a substituted or unsubstituted fused ring group having 5 to 50 ring carbon atoms and a fused heterocyclic group; m represents an integer of 1 to 3; k and q each represent an integer of 0 to 4; p represents an integer of 0 to 3; and n represents an integer of 0 to 5; when n represents 2 or more, multiple Ar's may be identical to or different from each other.

Further, in an organic EL device including one or multiple organic thin film layers including at least a light emitting layer, the one or multiple organic thin film layers being interposed between a cathode and an anode, the present invention provides an organic EL device in which at least one layer of the one or more multiple organic thin film layers contains the pyrene derivative alone or as a component of a mixture.

Effect of the Invention

The use of the pyrene derivative compound represented by the above general formula (1) as a light emitting material enables the production of an organic EL device emitting blue light and having high luminous efficiency and a long lifetime.

BEST MODE FOR CARRYING OUT THE INVENTION

A pyrene derivative of the present invention is represented by the following general formula (1):

  (1)

where: X's each represent a substituted or unsubstituted pyrene residue; A's and B's each independently represent a hydrogen atom, a substituted or unsubstituted aromatic hydrocarbon group having 3 to 50 ring carbon atoms, a substituted or unsubstituted aromatic heterocyclic group having 1 to 50 ring carbon atoms, a substituted or unsubstituted alkyl or alkylene group having 1 to 50 carbon atoms, or a substituted or unsubstituted alkenyl or alkenylene group having 1 to 50 carbon atoms; Ar's represent at least any one of a substituted or unsubstituted aromatic hydrocarbon group having 3 to 50 ring carbon atoms and a substituted or unsubstituted aromatic heterocyclic group having 1 to 50 ring carbon atoms; Y's represent at least any one of a substituted or unsubstituted fused ring group having 5 to 50 ring carbon atoms and a fused heterocyclic group; m represents an integer of 1 to 3; k and q each represent an integer of 0 to 4; p represents an integer of 0 to 3; and n represents an integer of 0 to 5; when n represents 2 or more, multiple Ar's may be identical to or different from each other.

The pyrene derivative represented by the above general formula (1) of the present invention is preferably of a structure represented by the following general formula (2):

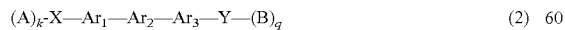  (2)

where: X, A, B, Y, k, and q each have the same meaning as that described above; and $Ar_1$ to $Ar_3$ each have the same meaning as that of Ar in the general formula (1).

In the general formula (1), at least one of an X—Ar bond, an Ar—Y bond, and an Ar—Ar bond is preferably a meta bond or an ortho bond. Further, in the general formula (2), at least one of an X—$Ar_1$ bond, an $Ar_1$—$Ar_2$ bond, an $Ar_2$—$Ar_3$ bond, and an $Ar_3$—Y bond is preferably a meta bond or an ortho bond.

At least any one of an Ar group in the general formula (1) and $Ar_1$ to $Ar_3$ groups in the general formula (2) is preferably an unsubstituted phenylene group.

Examples of the substituted or unsubstituted pyrene group represented by X in the above general formula (1) or (2) include such residues as shown below each obtained by removing a hydrogen atom from a pyrene compound.

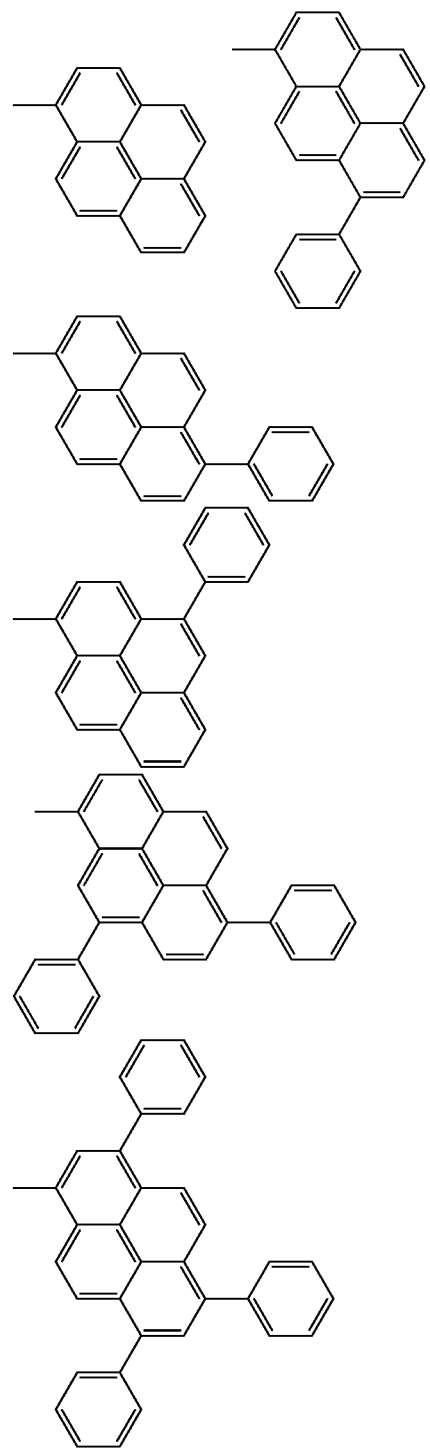

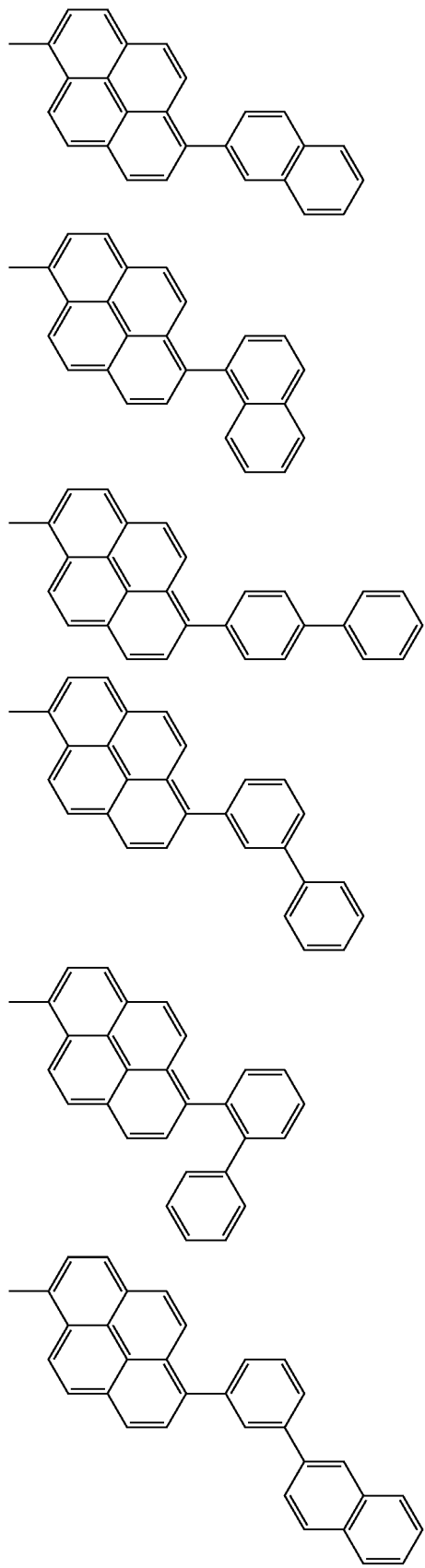
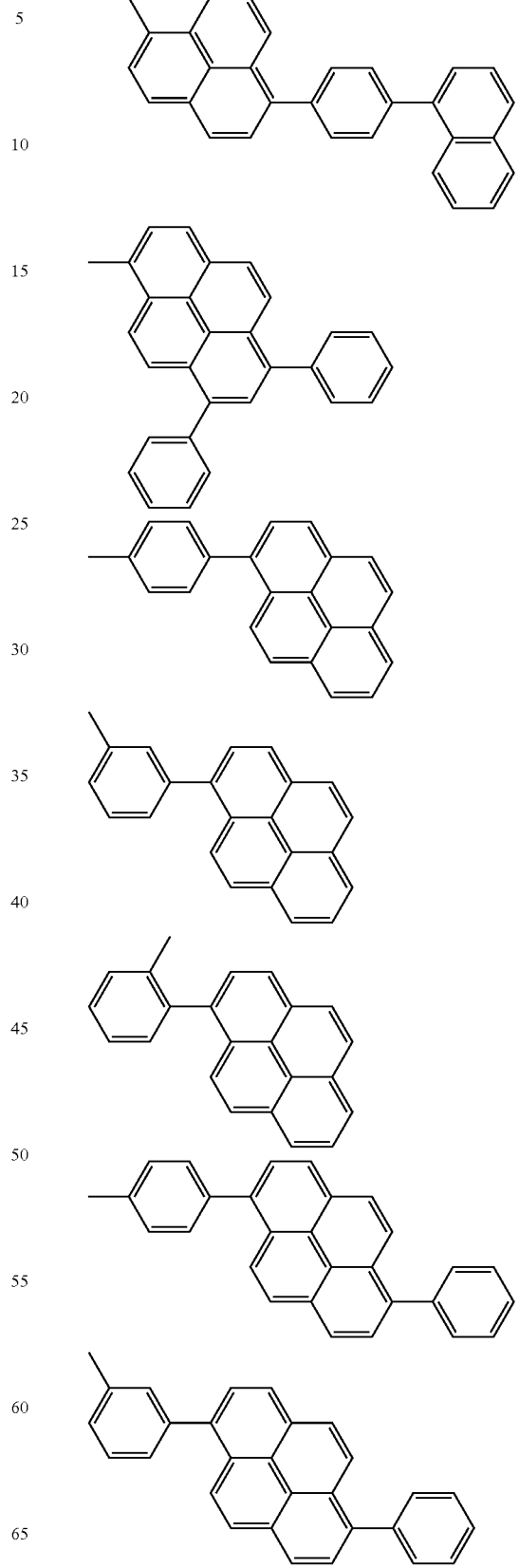

-continued
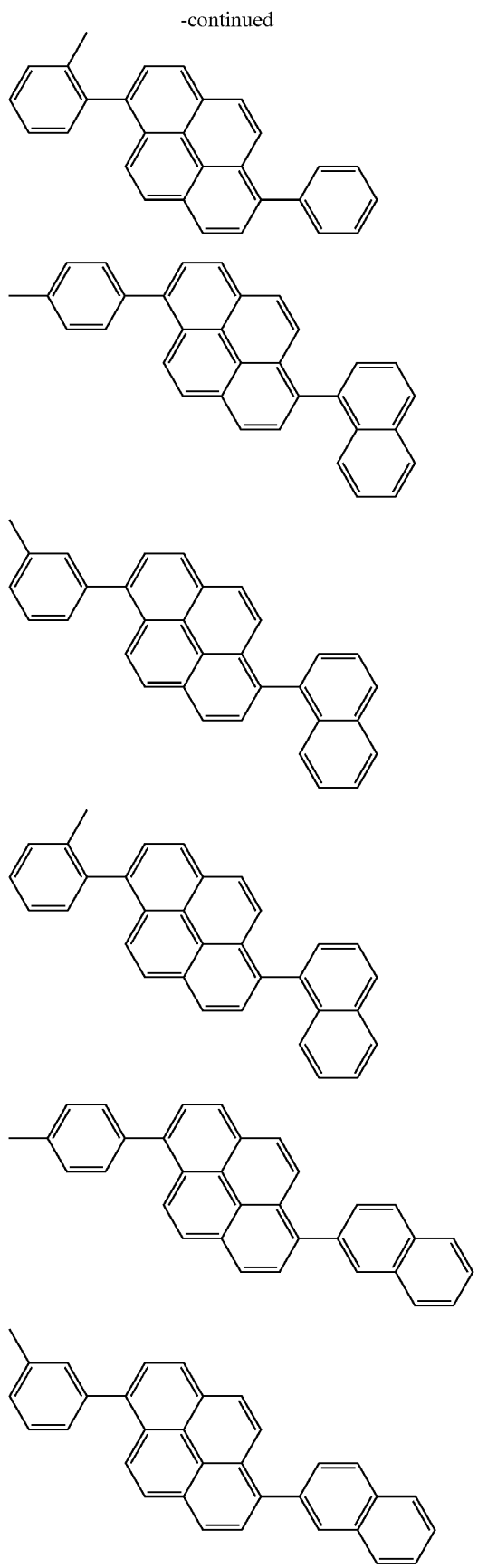
-continued
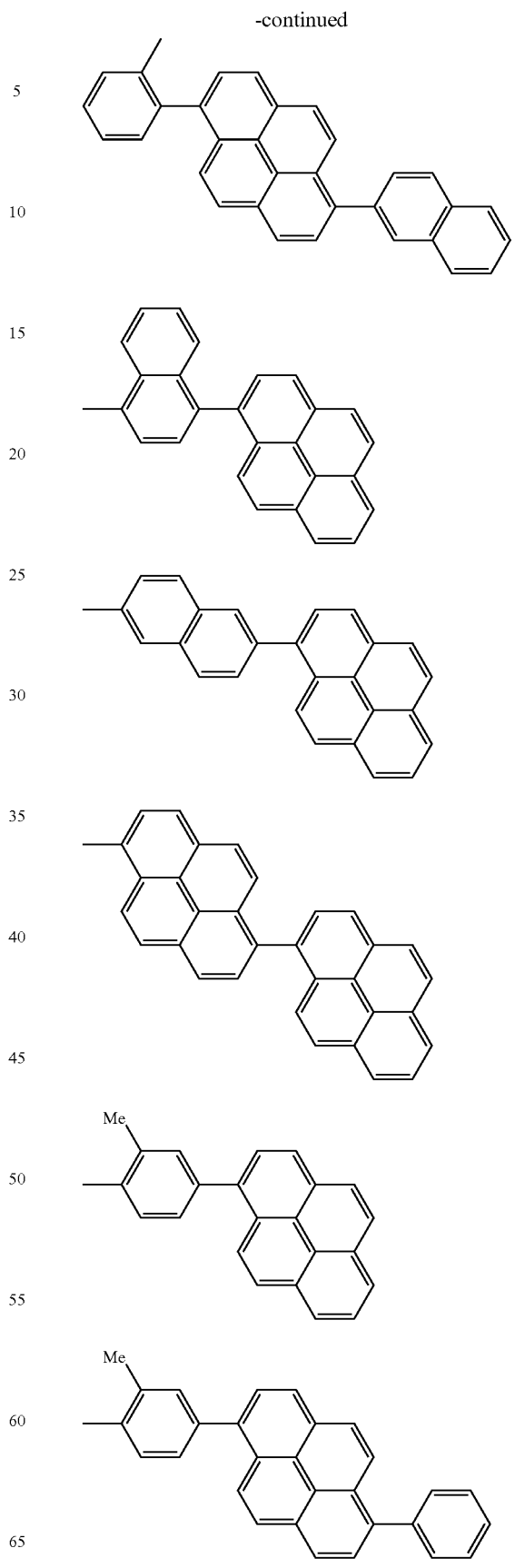

-continued
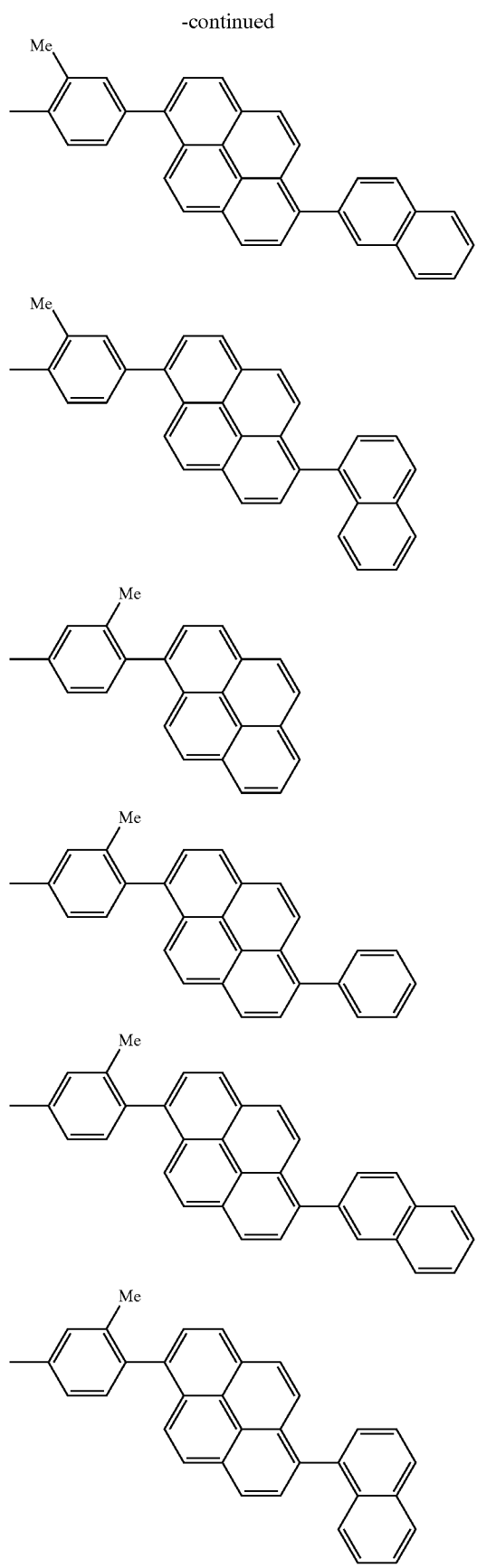
-continued
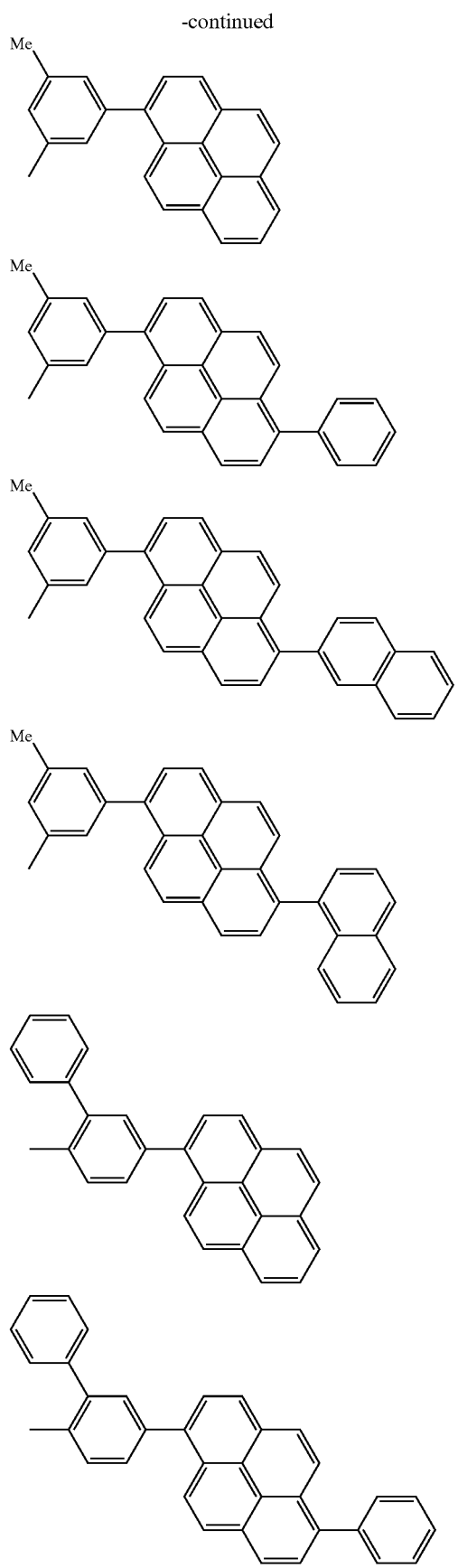

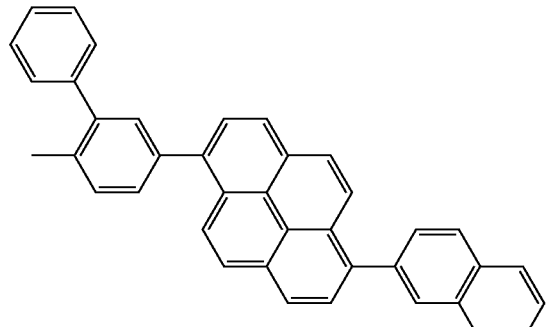
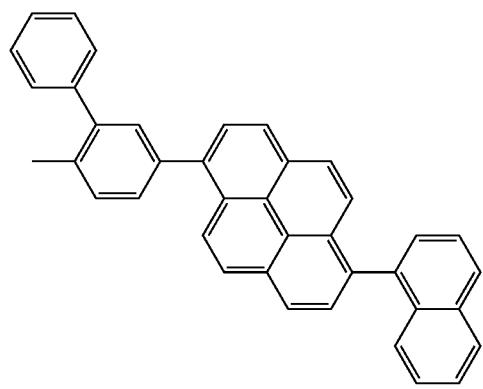
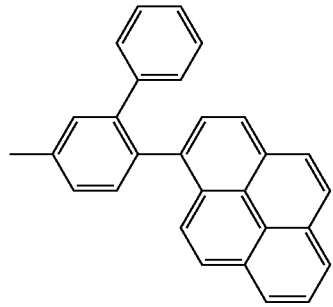
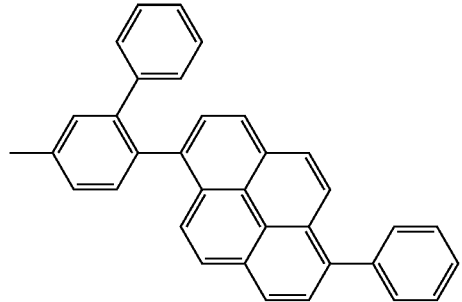
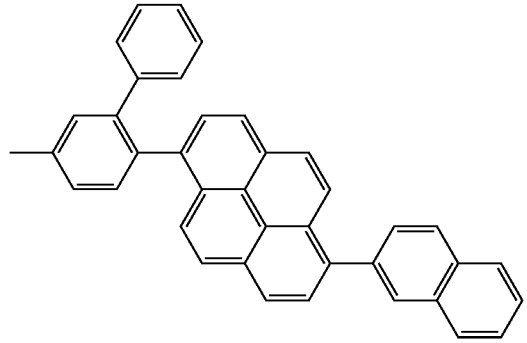
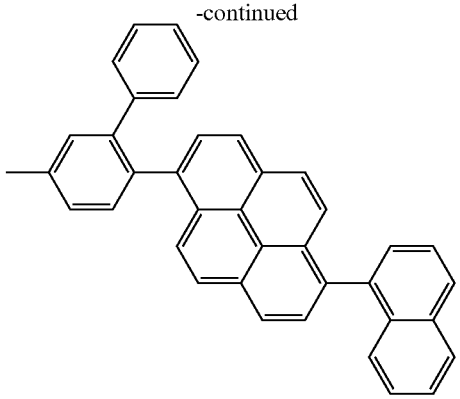
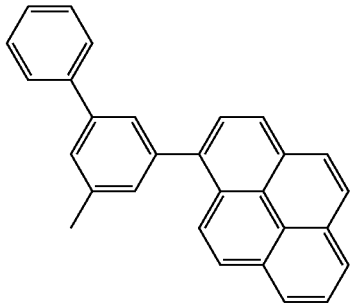
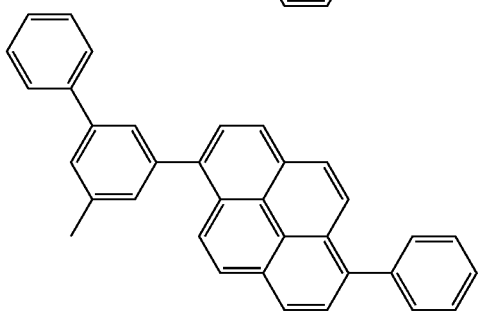
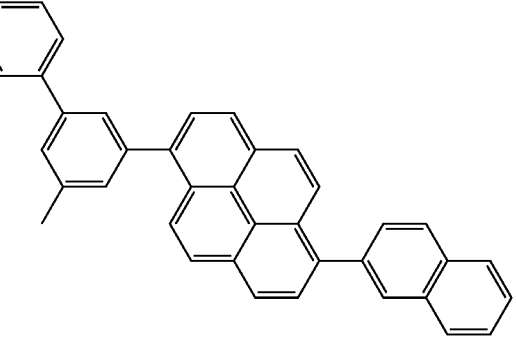
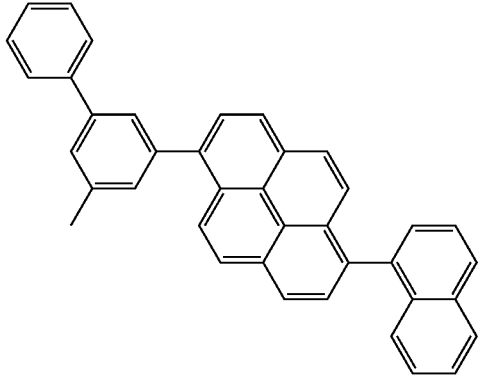

-continued
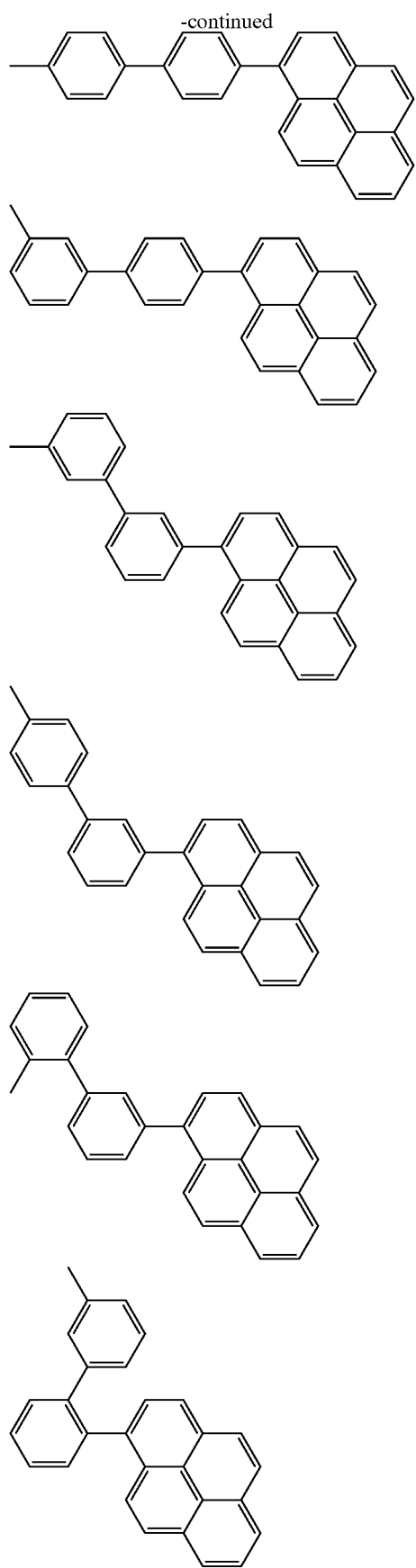
-continued
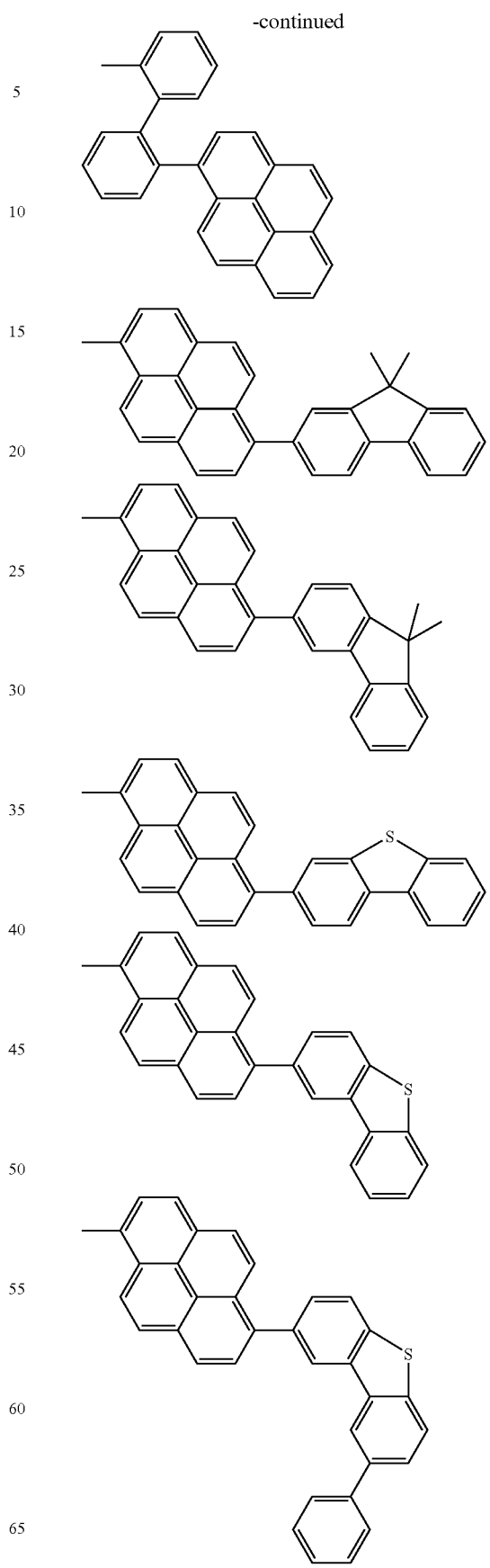

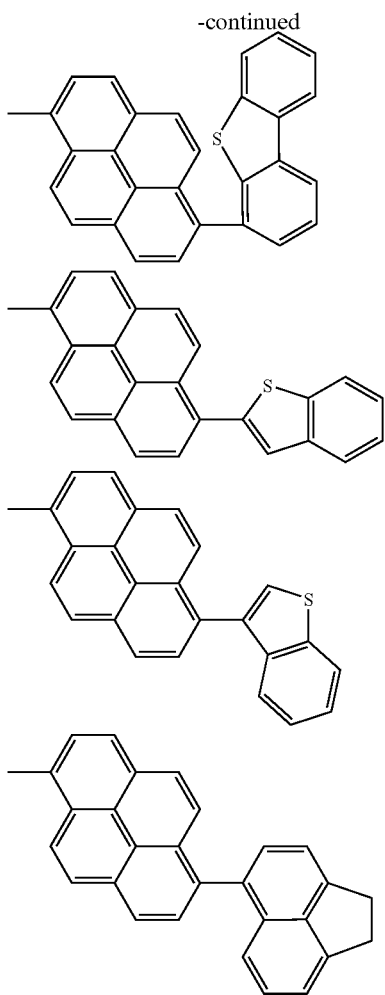

The substituted or unsubstituted aromatic hydrocarbon groups having 3 to 50 ring carbon atoms, represented by A, B, Ar and $Ar_1$ to $Ar_3$ in the general formula (1) or (2) include, for example, a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group, and groups each obtained by turning any one of those groups divalent.

The substituted or unsubstituted aromatic heterocyclic groups having 1 to 50 ring carbon atoms, represented by A, B, Ar and $Ar_1$ to $Ar_3$ in the general formula (1) or (2) include, for example, a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, and groups each obtained by turning any one of those groups divalent.
Preferable examples of the structural formulae represented by Ar and $Ar_1$ to $Ar_3$ in the above general formula (1) or (2) are shown below. However, the present invention is not limited to the examples.
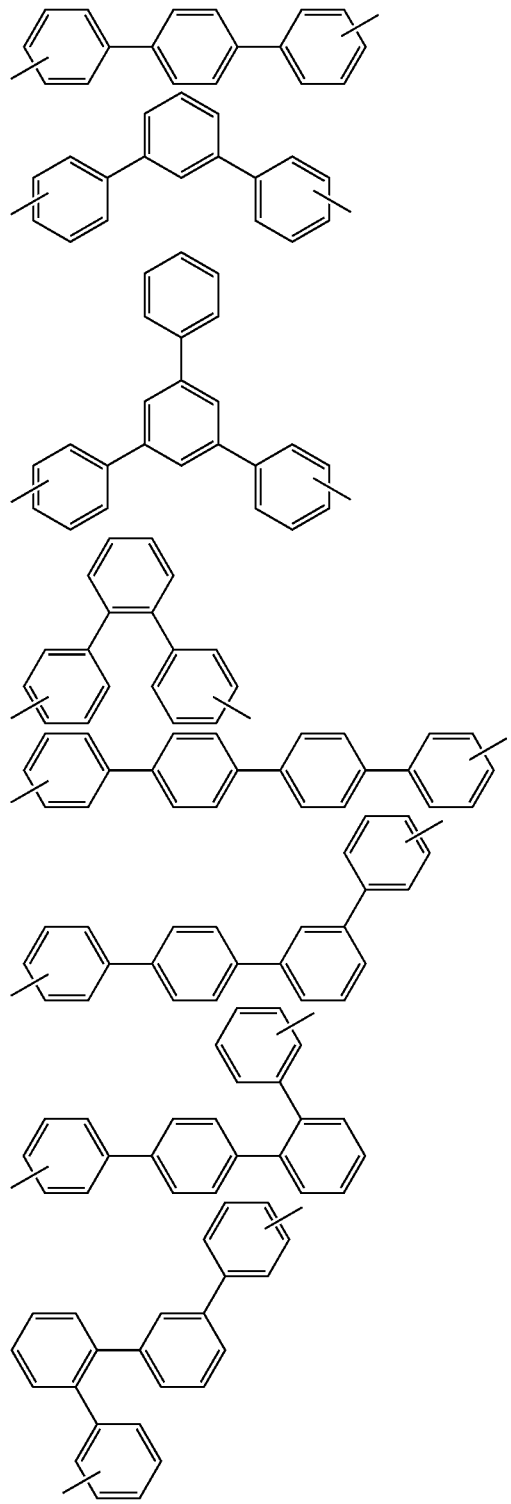
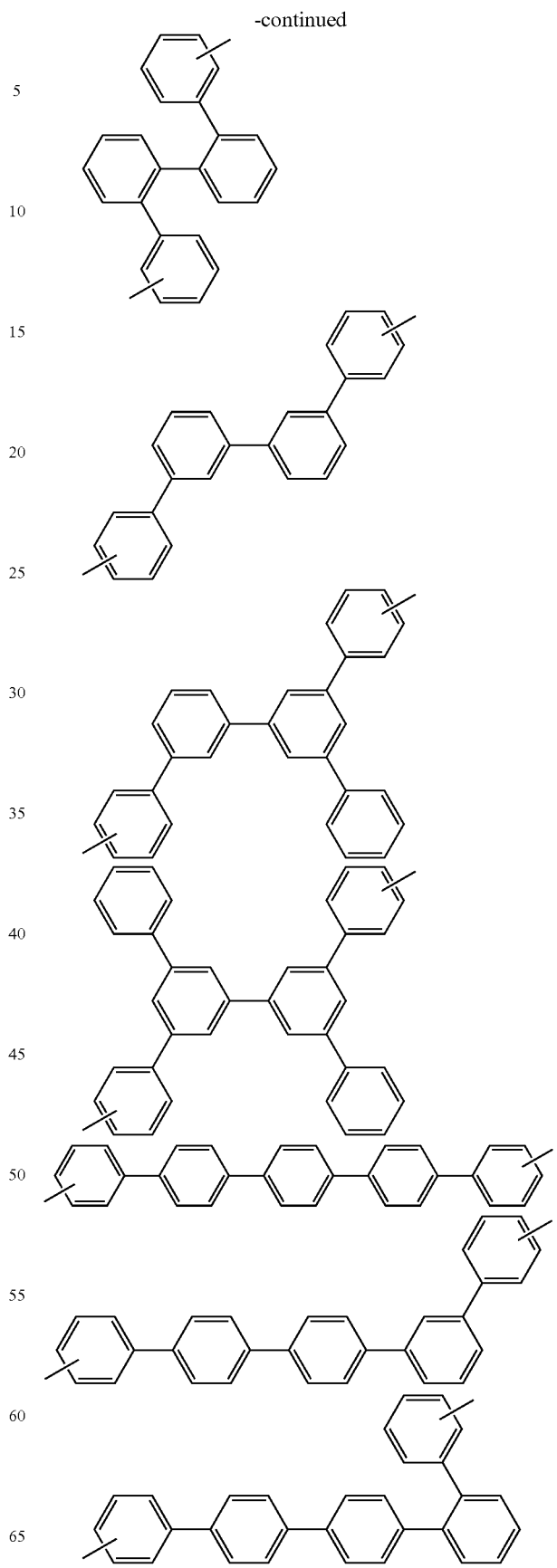
-continued

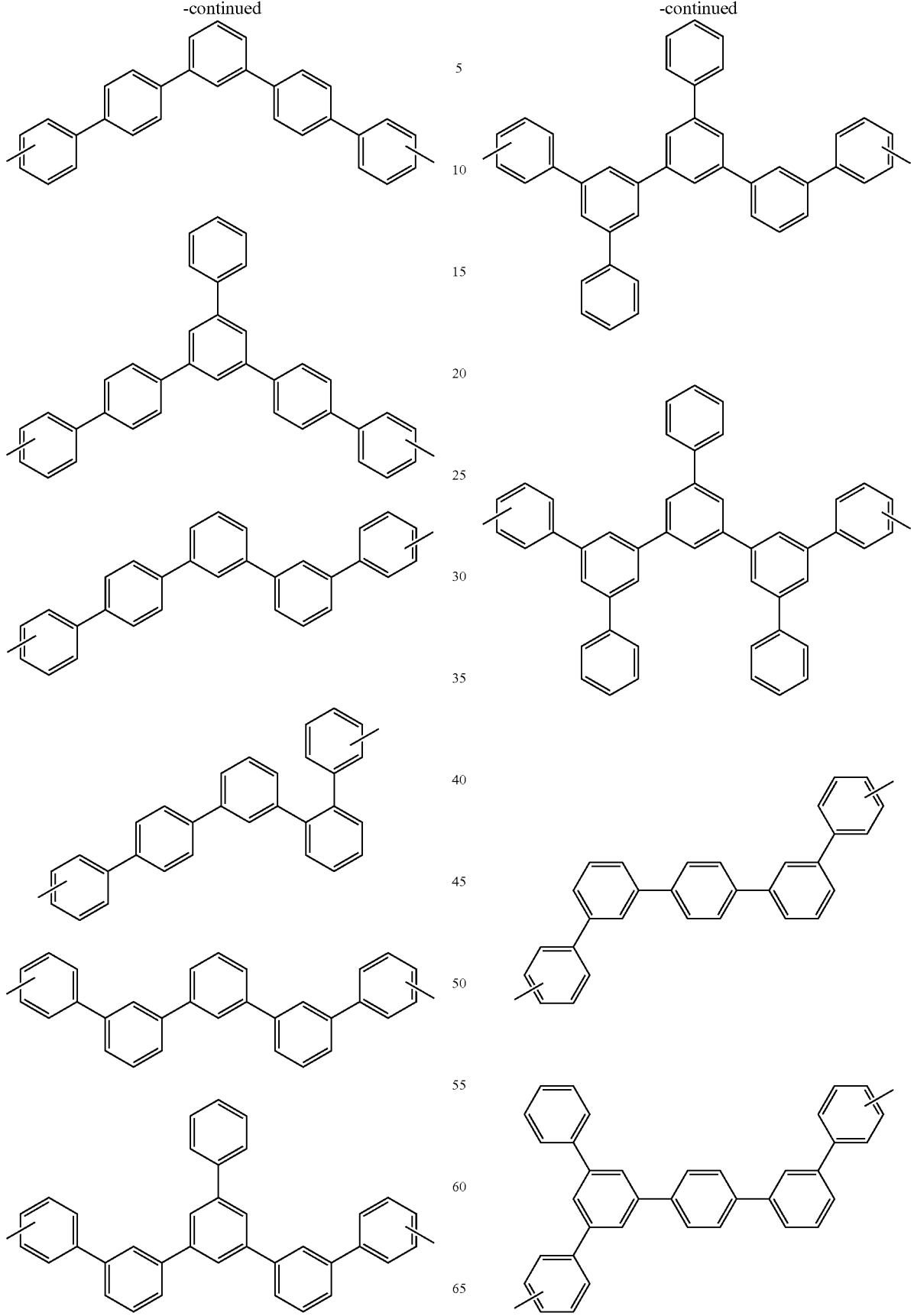

-continued

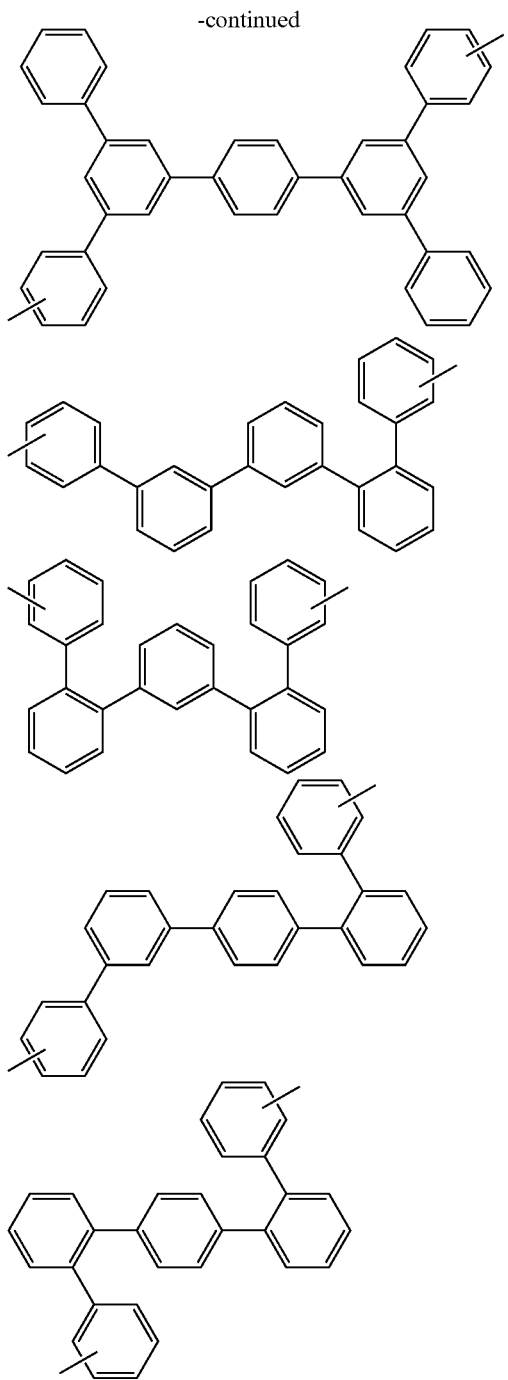

In the general formula (1) or (2), examples of the substituted or unsubstituted alkyl group or alkylene group represented by A and B having 1 to 50 carbon atoms include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, and bivalent groups thereof.

Examples of the substituted or unsubstituted alkenyl or alkenylene group having 1 to 50 carbon atoms represented by each of A's and B's in the above general formula (1) or (2) include a vinyl group, an allyl group, a 1-butenyl group, a 2-butenyl group, a 3-butenyl group, a 1,3-butanedienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, and a 3-phenyl-1-butenyl group, and groups each obtained by turning any one of those groups divalent.

In the general formula (1) or (2), examples of the substituted or unsubstituted fused ring group and the fused heterocyclic group represented by Y having 5 to 50 ring carbon atoms include residues of pyrene, anthracene, benzanthracene, naphthalene, fluoranthene, fluorene, benzfluorene, diazafluorene, phenanthrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, imine, diphenylethylene, vinylanthracene, diaminocarbazole, pyrane, thiopyrane, polymethine, merocyanine, imidazole-chelated oxynoid compounds, quinacridone, rubrene, stilbene-based derivatives, and fluorescent dyes. The residues of pyrene, anthracene, and fluoranthene are preferred.

Examples of the substituents of X, A, B, Ar, Y, $Ar_1$, $Ar_2$, and $Ar_3$ of the pyrene derivative, represented by the general formula (1) or (2), include, as an alkyl group, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

Of those, a methyl group, an ethyl group, a propyl group, an isopropyl group, an n-butyl group, an s-butyl group, an isobutyl group, a t-butyl group, and an n-pentyl group are preferable, and an isopropyl group, an s-butyl group, and a t-butyl group are particularly preferable.

Examples of the compound represented by the general formula (1) or (2) are shown below. However, the compound of the present invention is not limited to those examples.

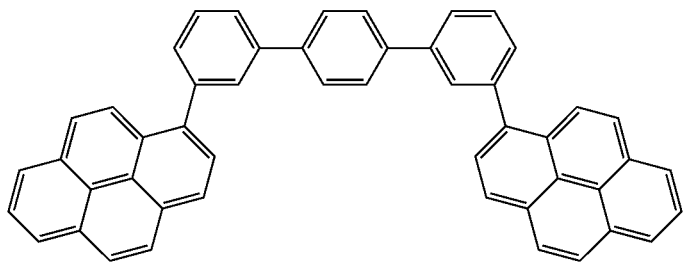

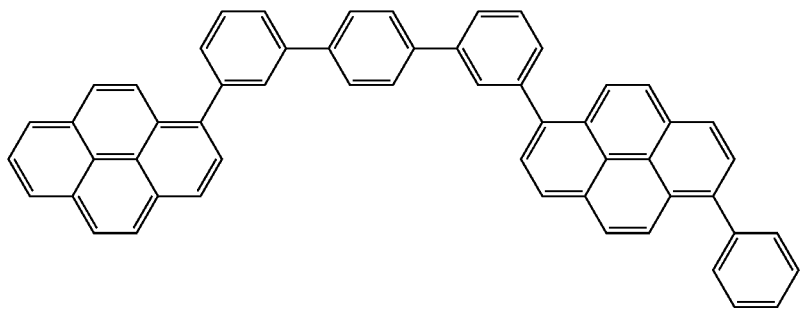

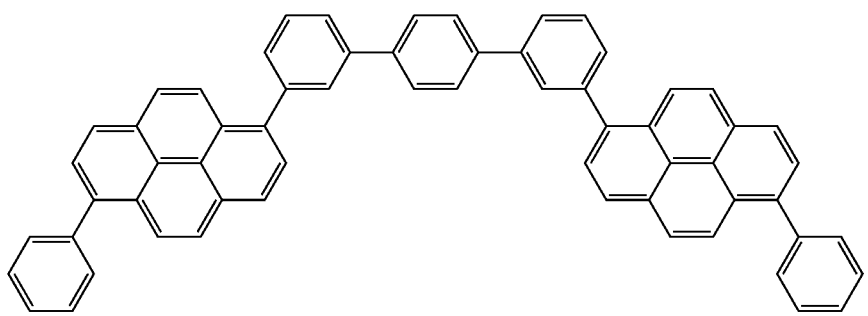

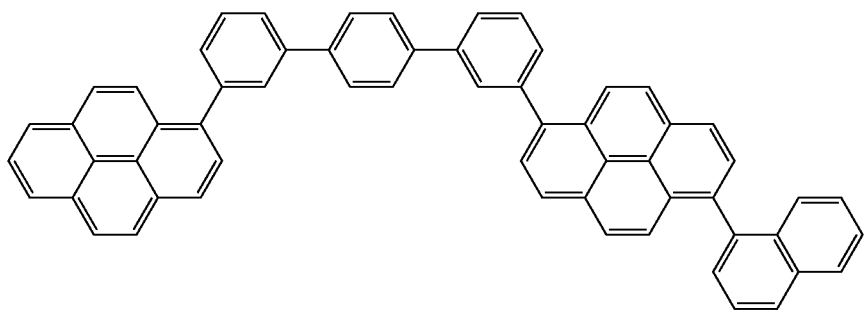

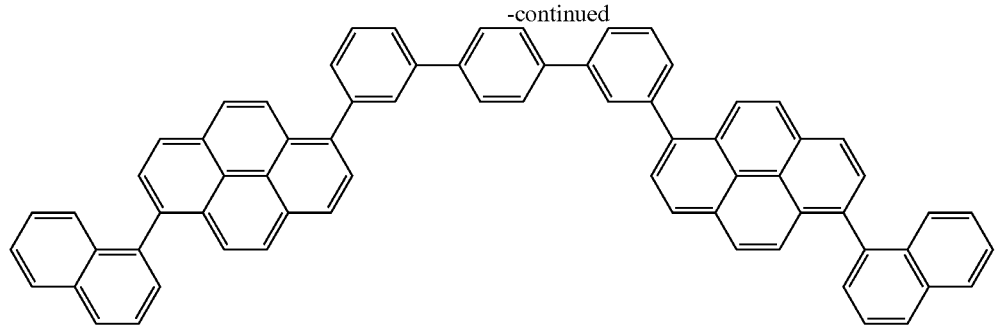
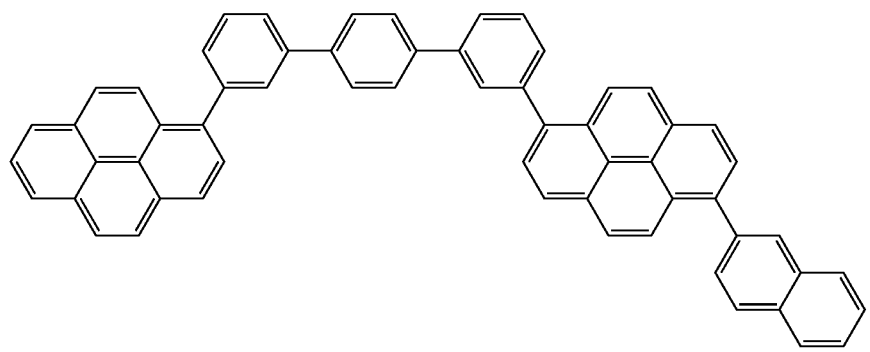
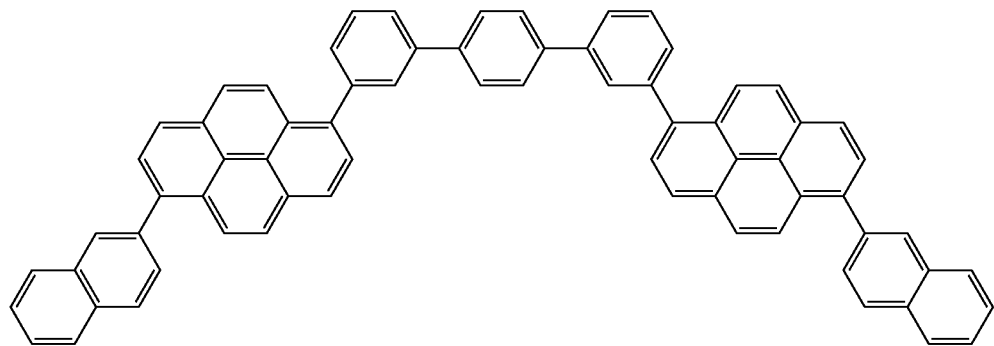
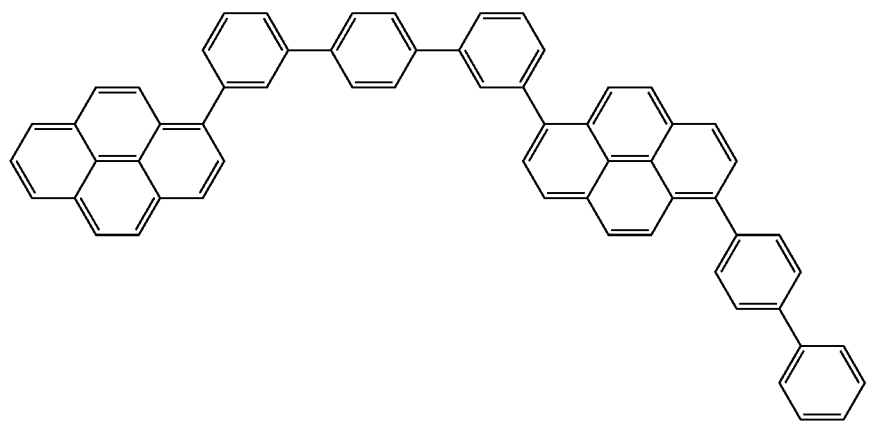

-continued
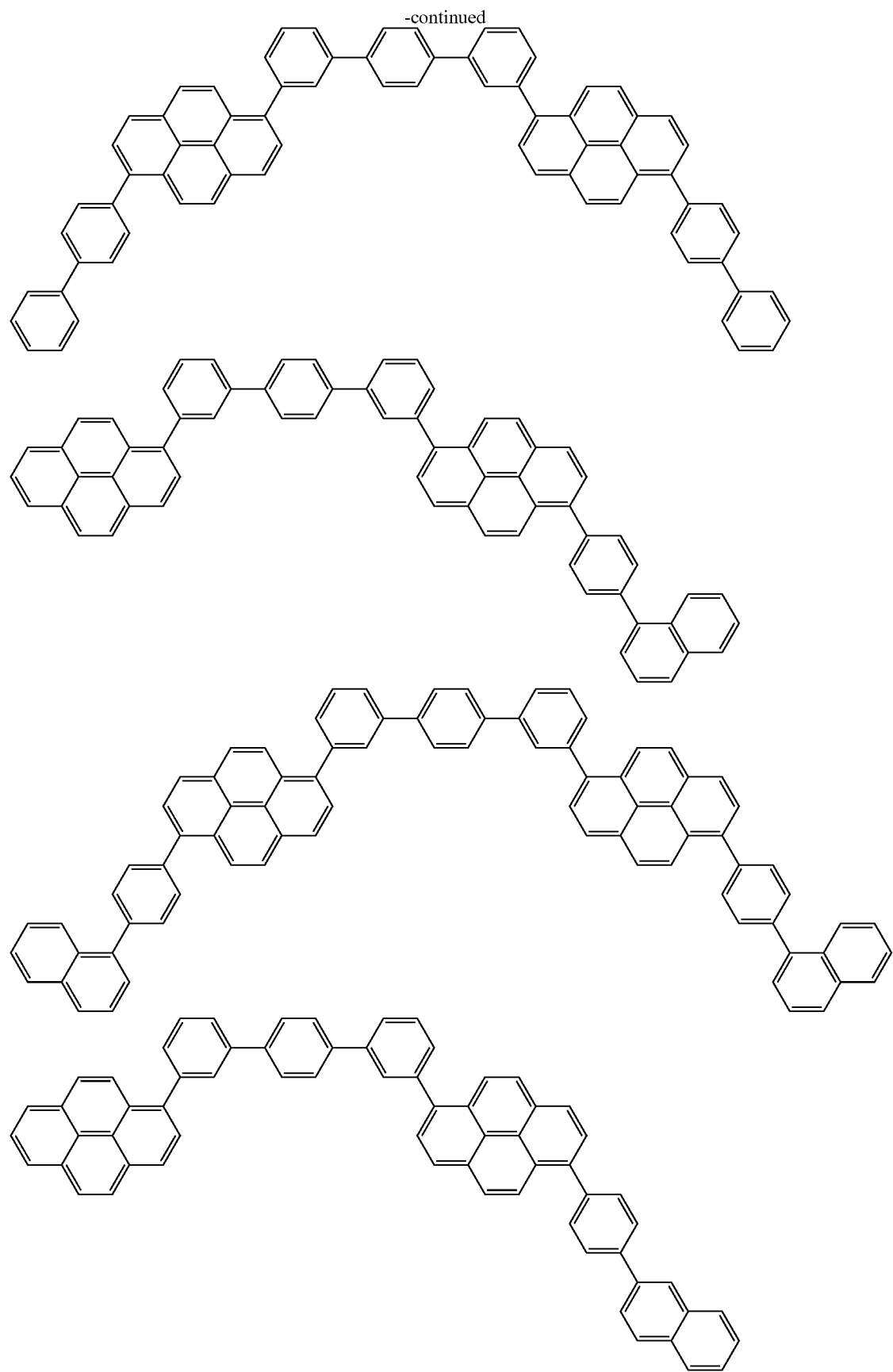

-continued
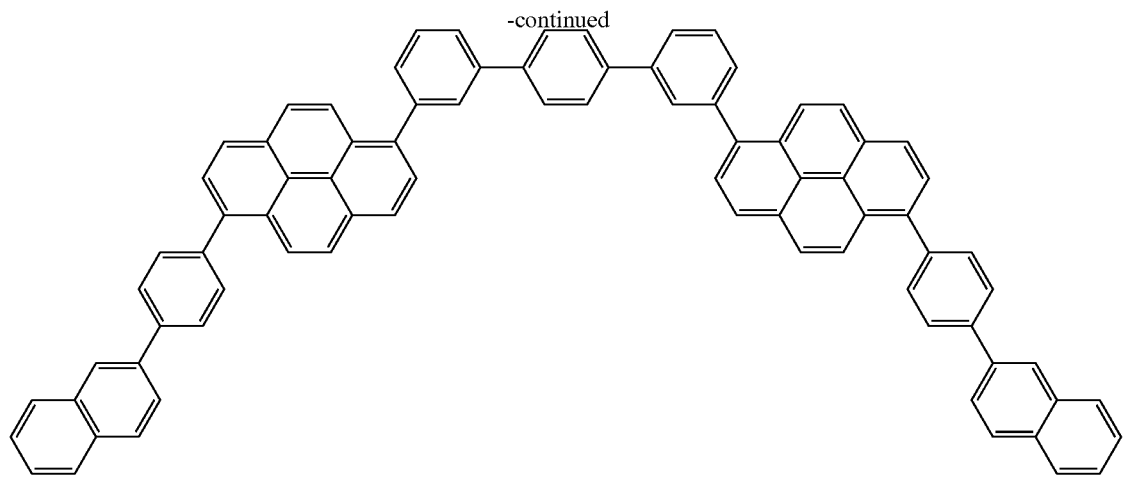
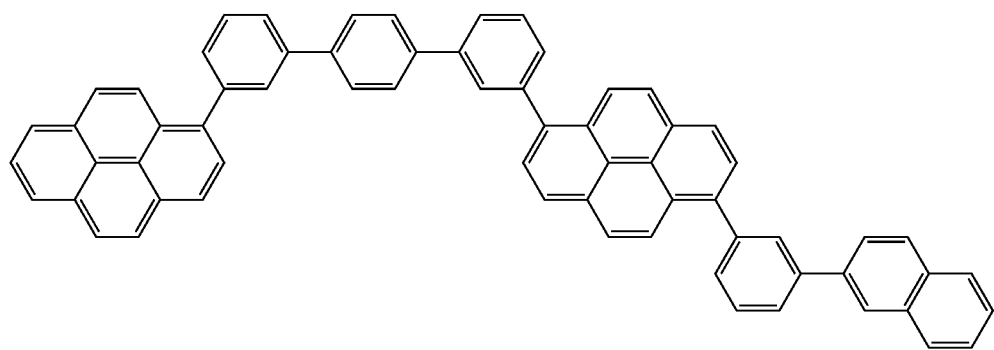
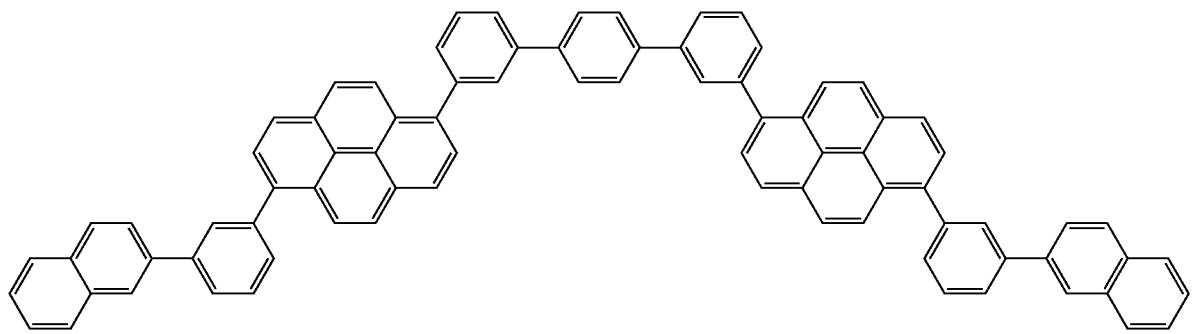
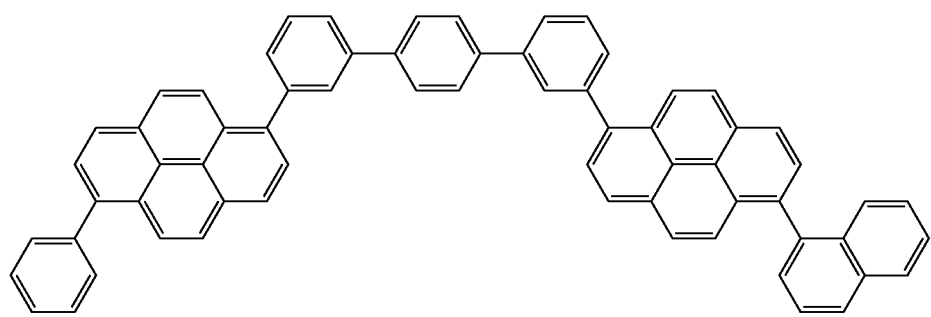

-continued
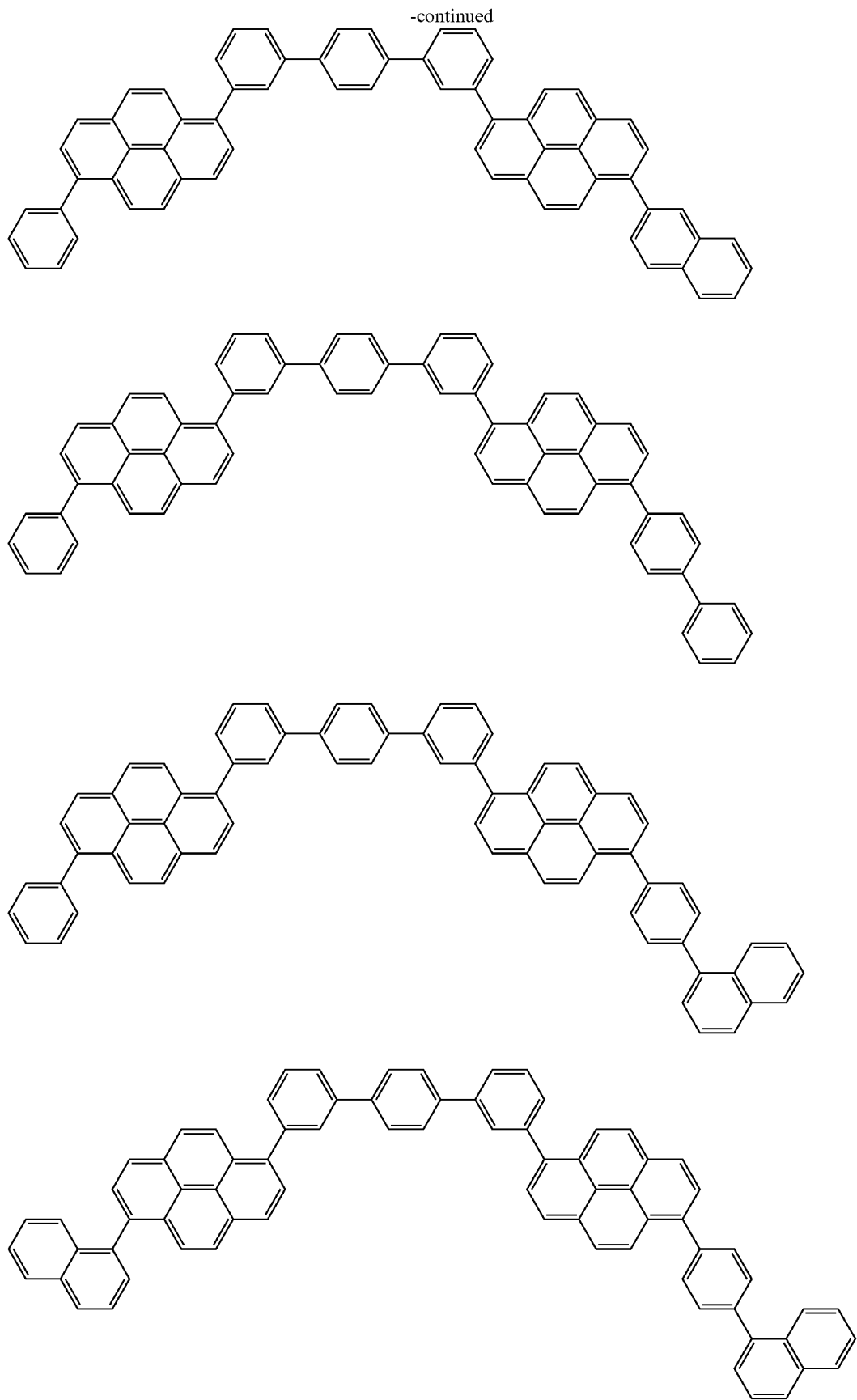

-continued
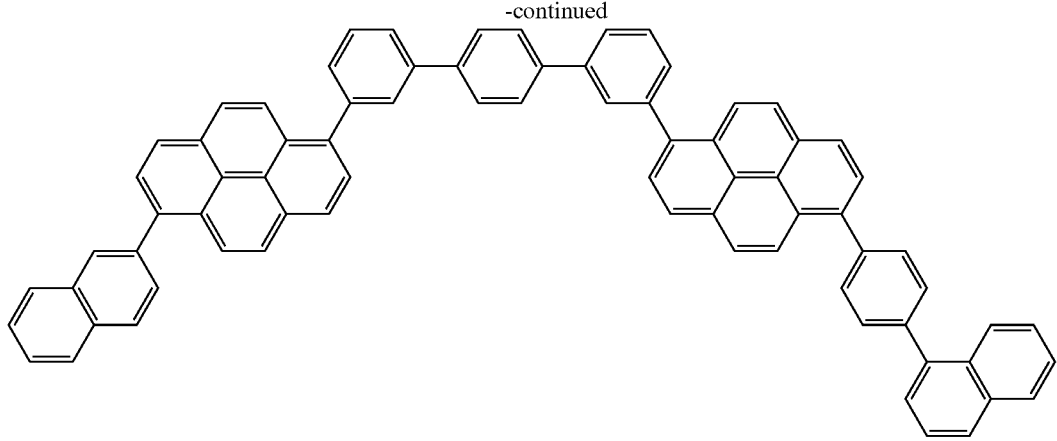
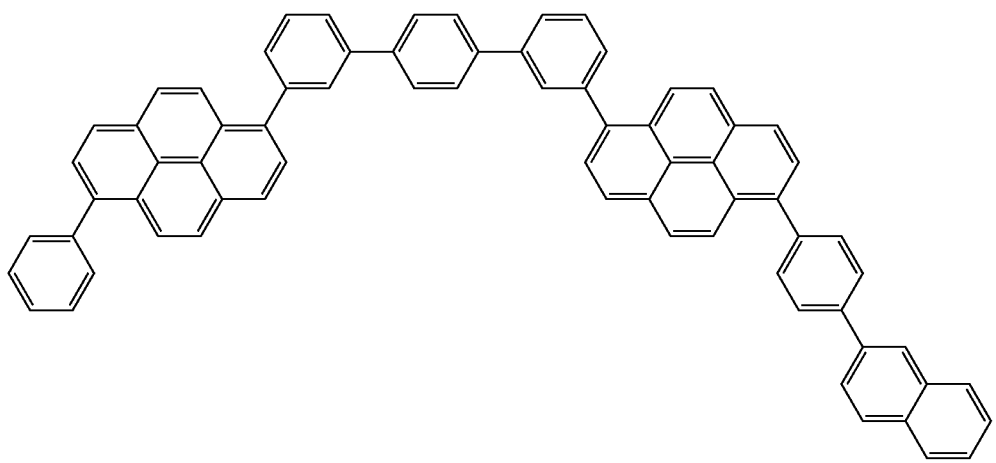
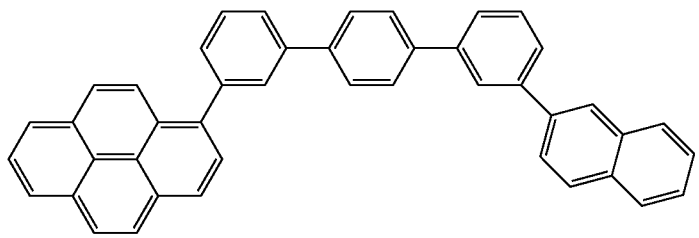
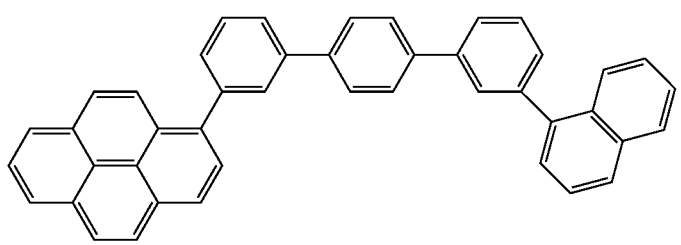

-continued
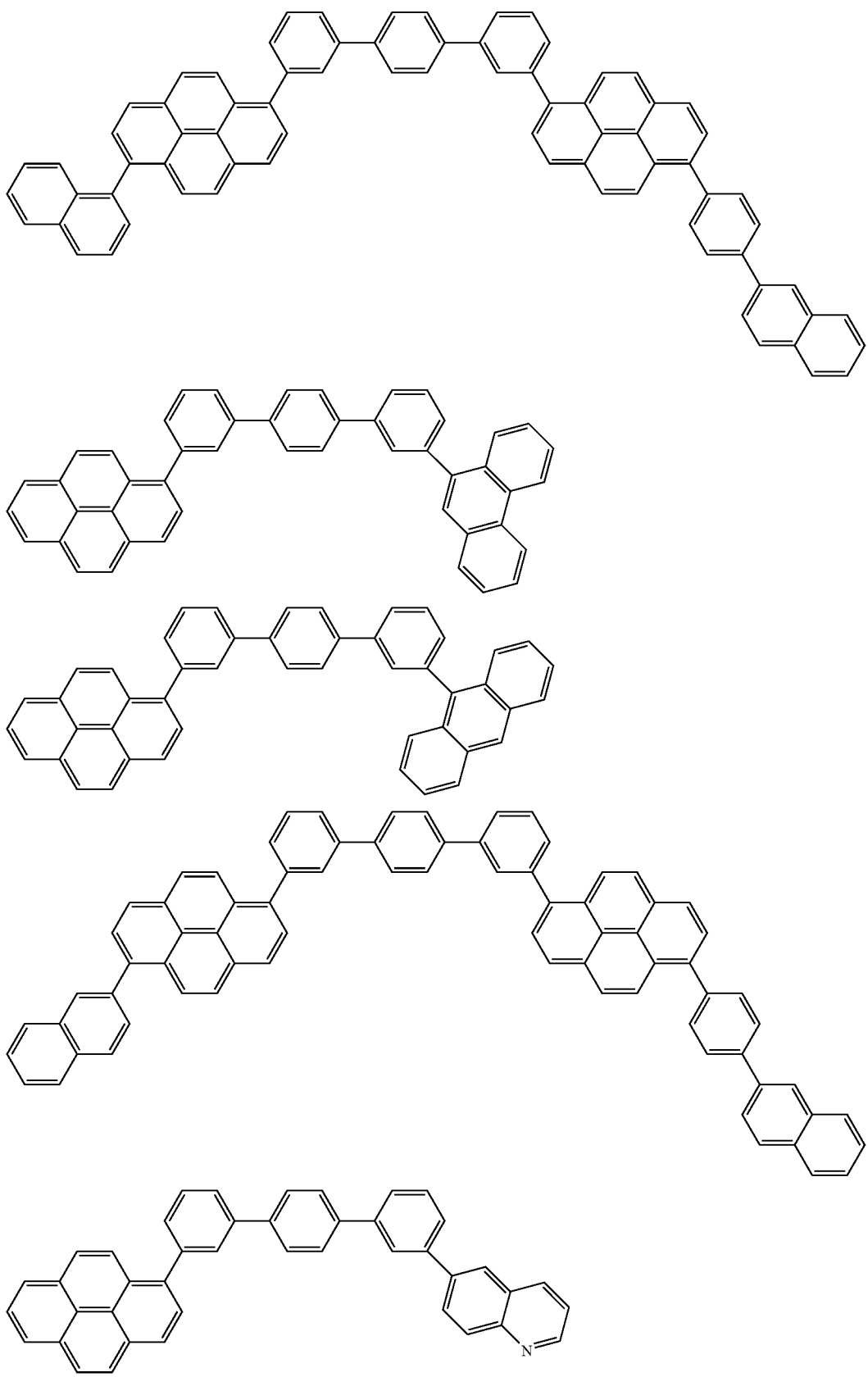

-continued
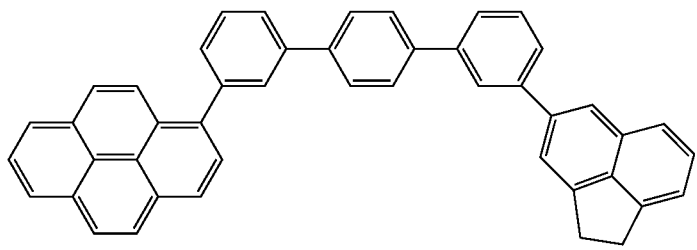
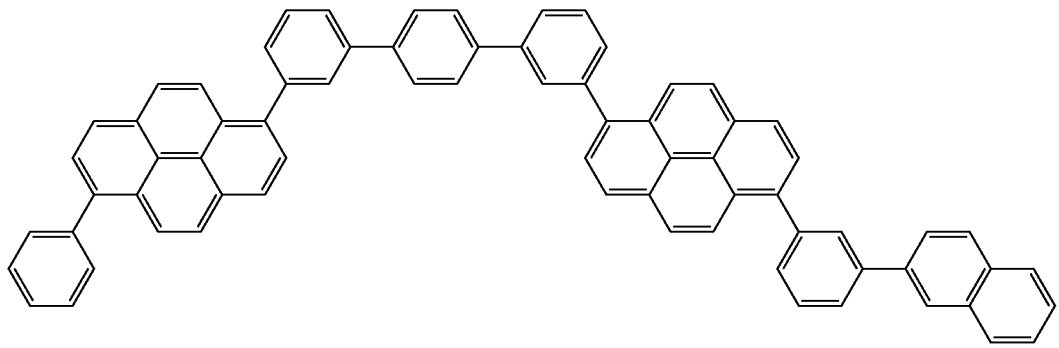
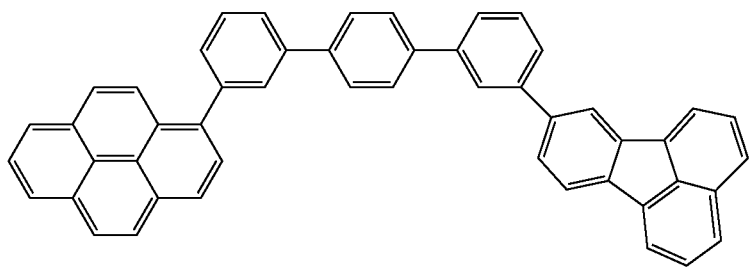
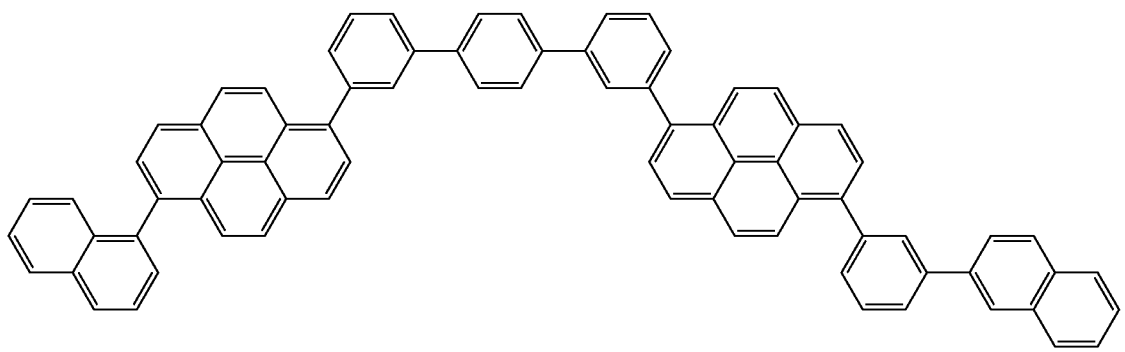
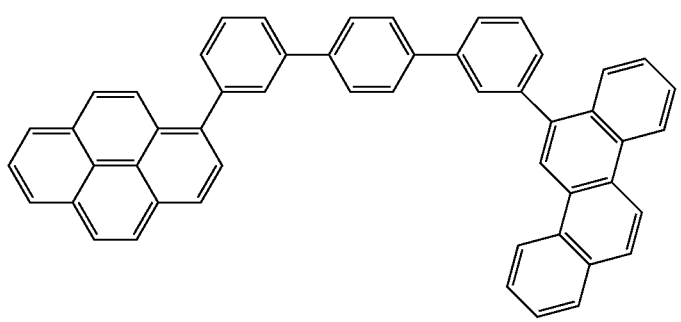

-continued
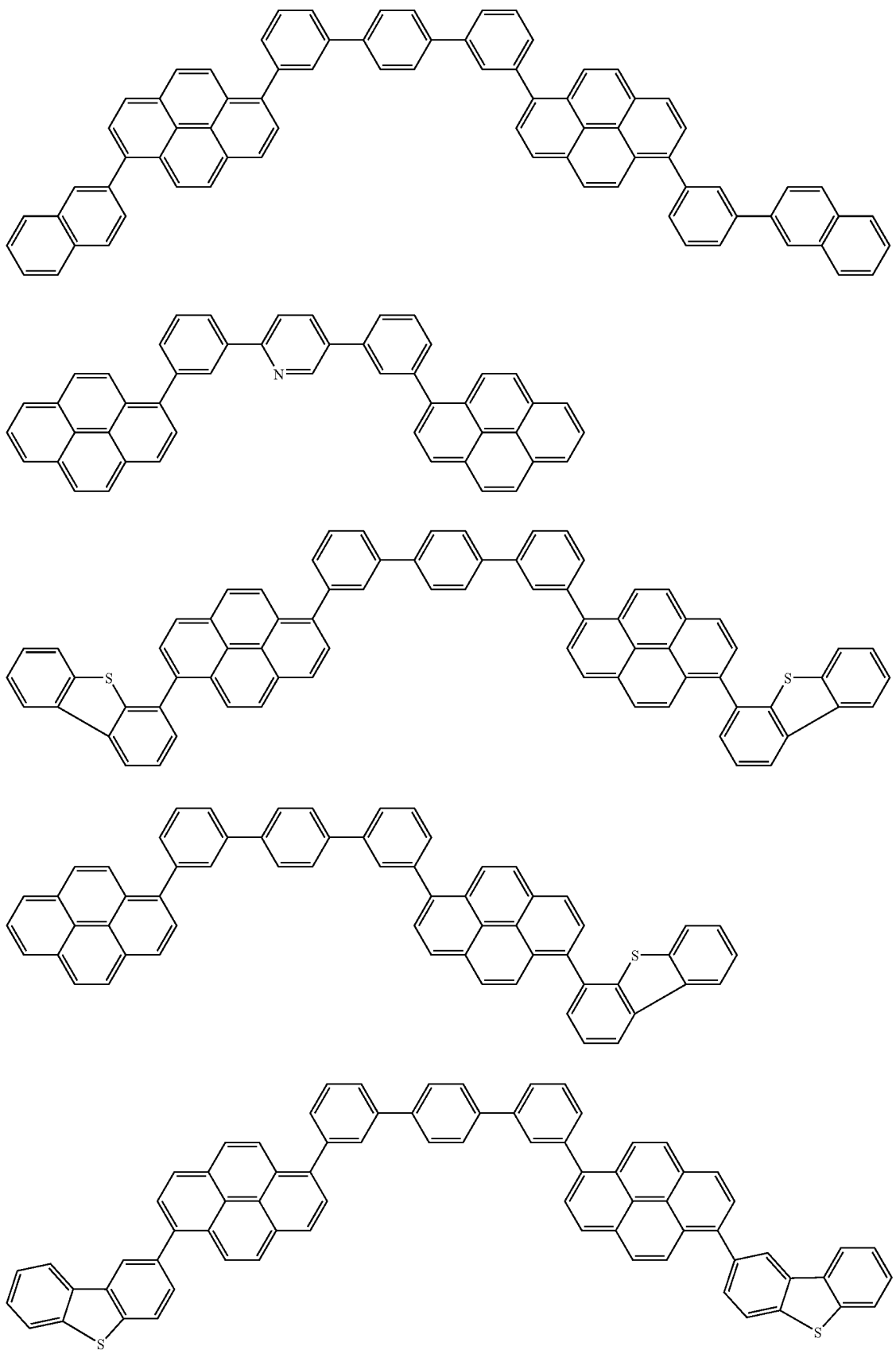

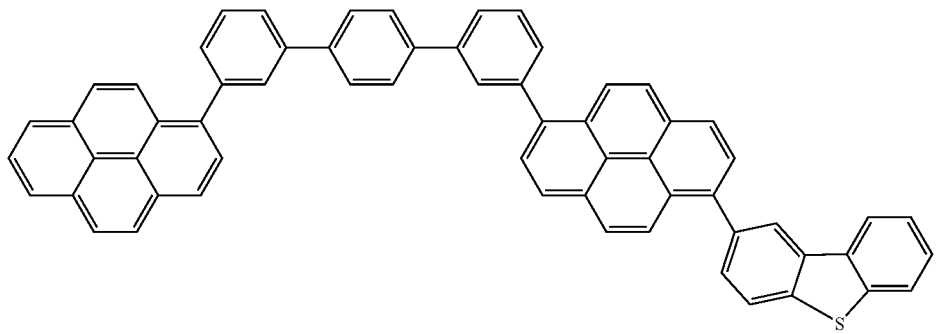
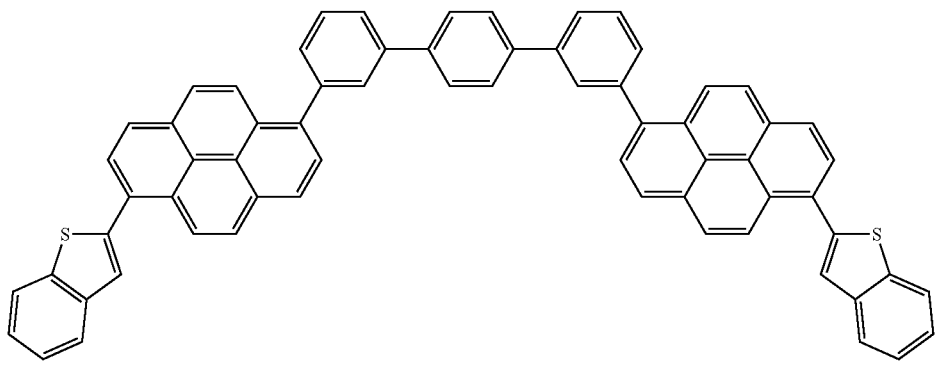
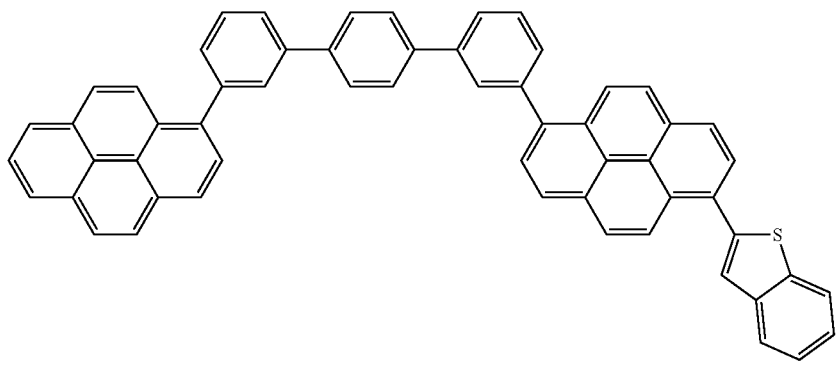
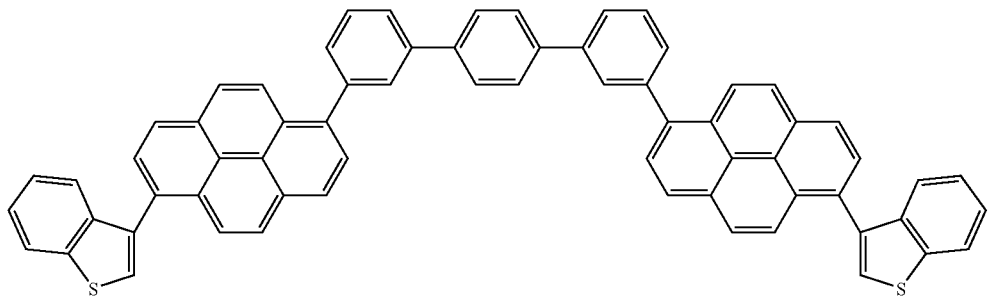
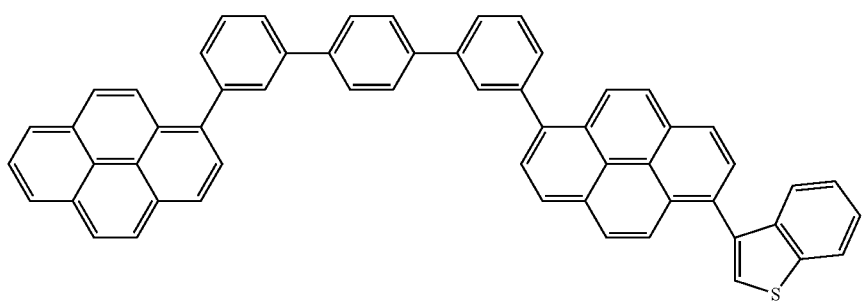

-continued
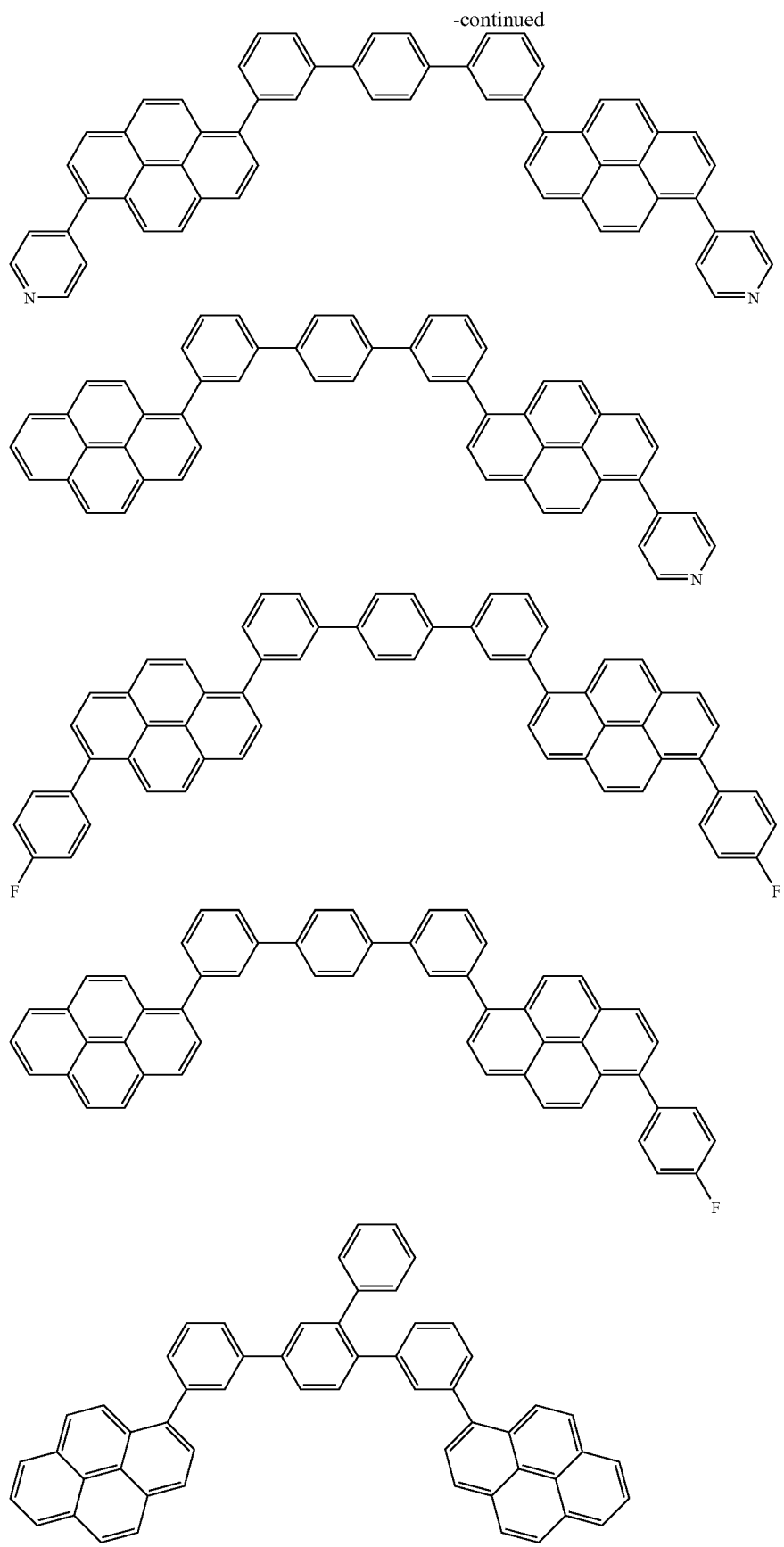

-continued
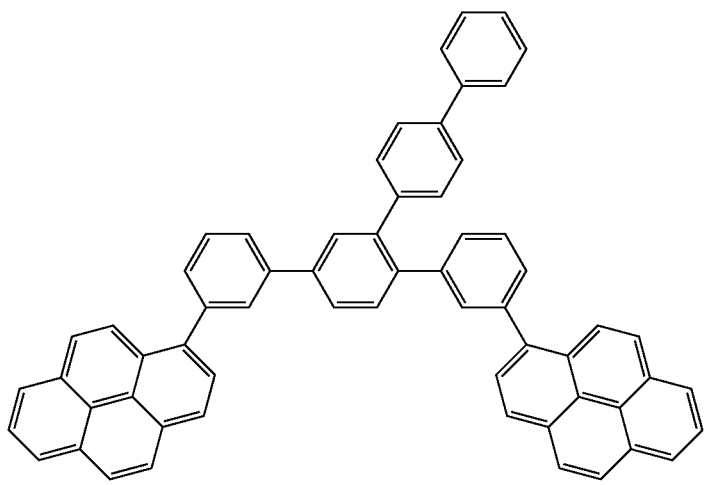
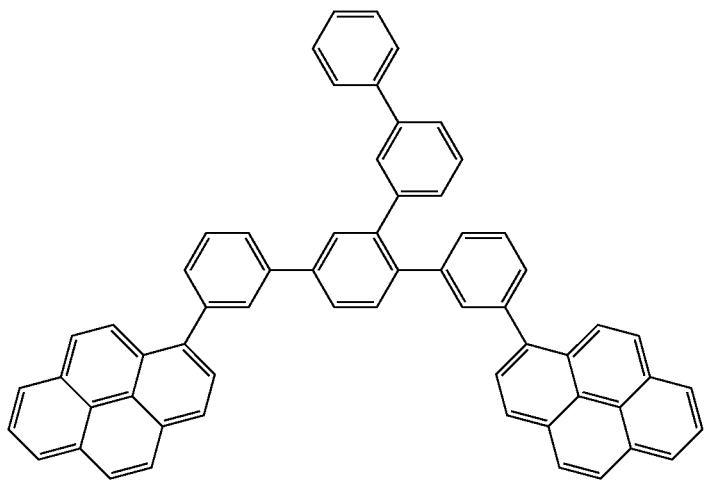
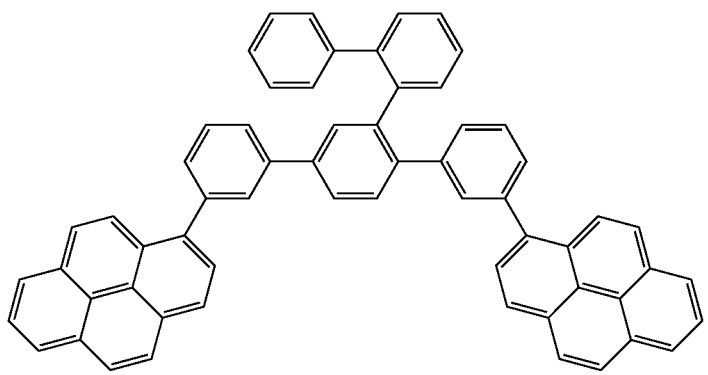

-continued
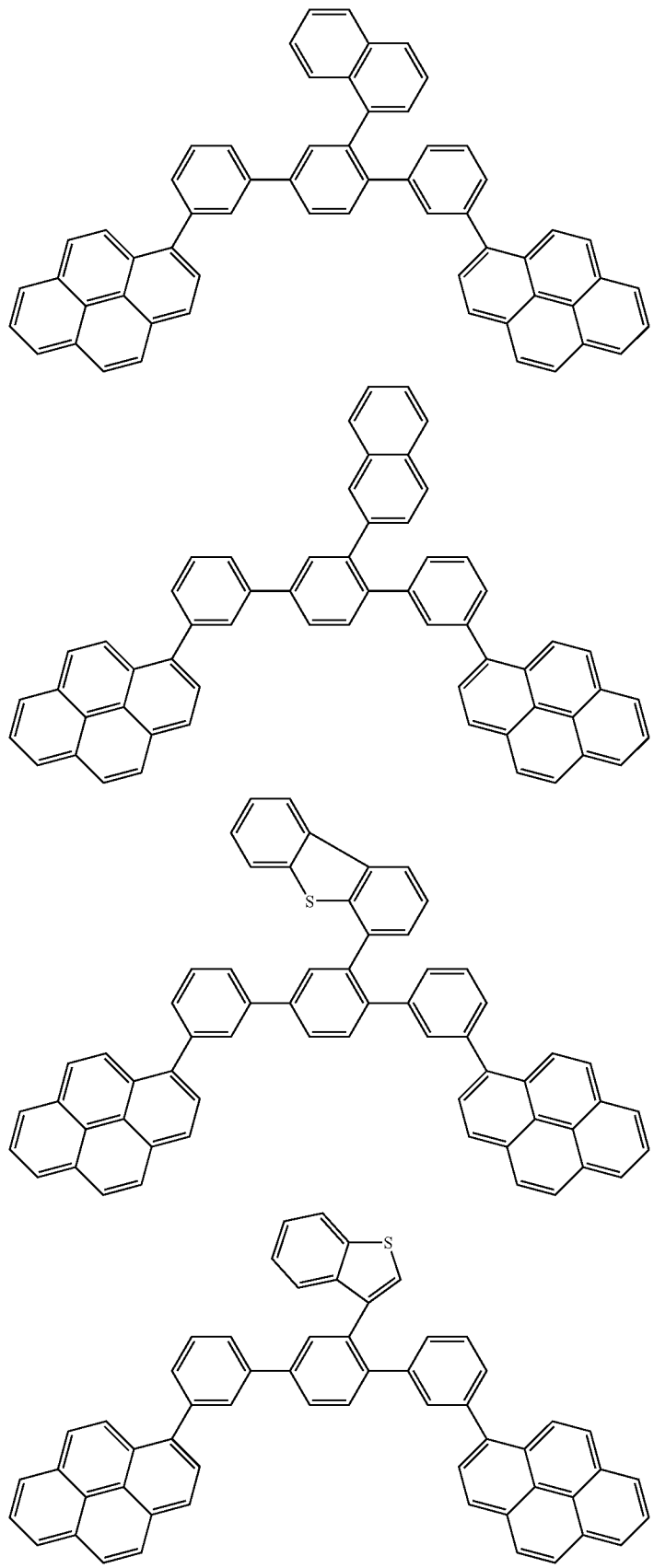

-continued
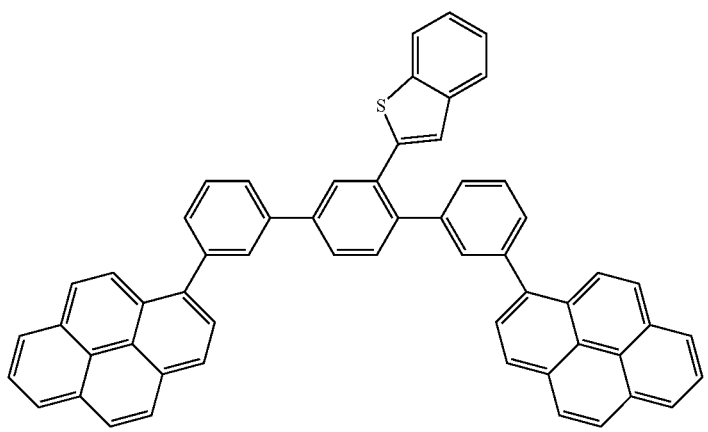
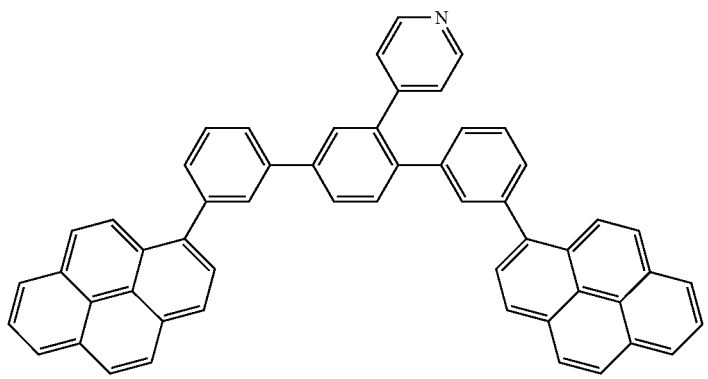
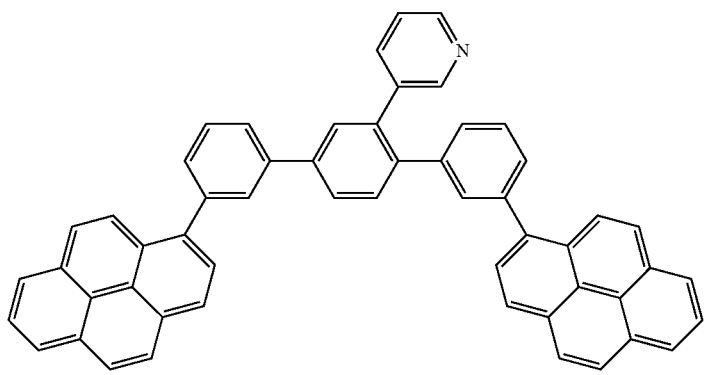
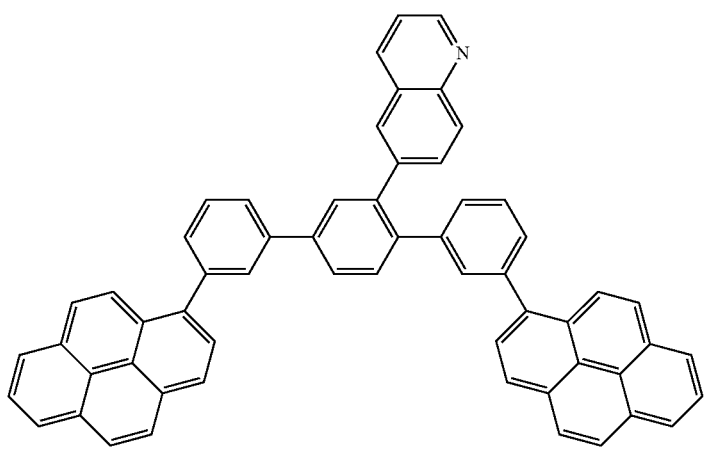

-continued
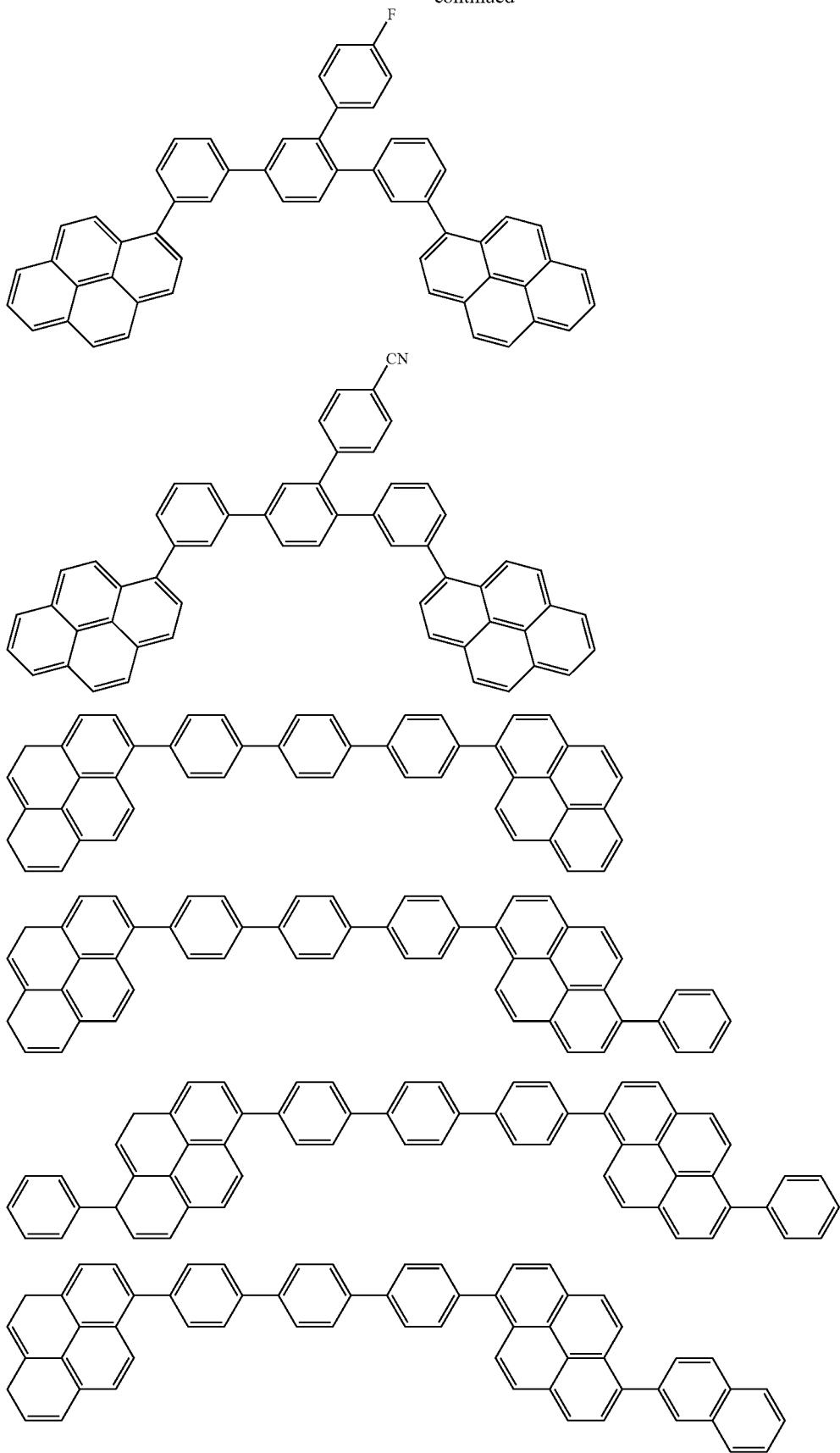

-continued
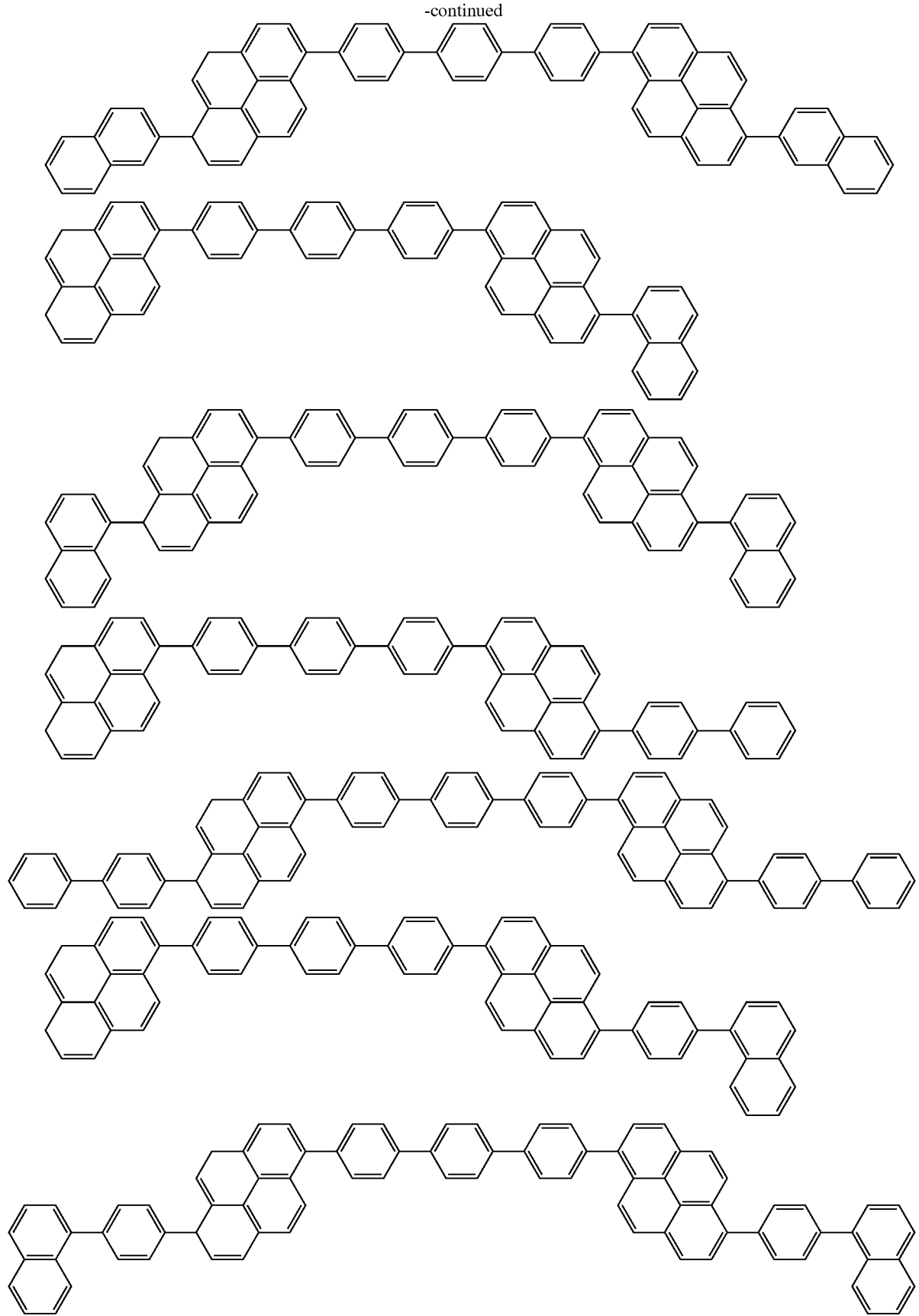

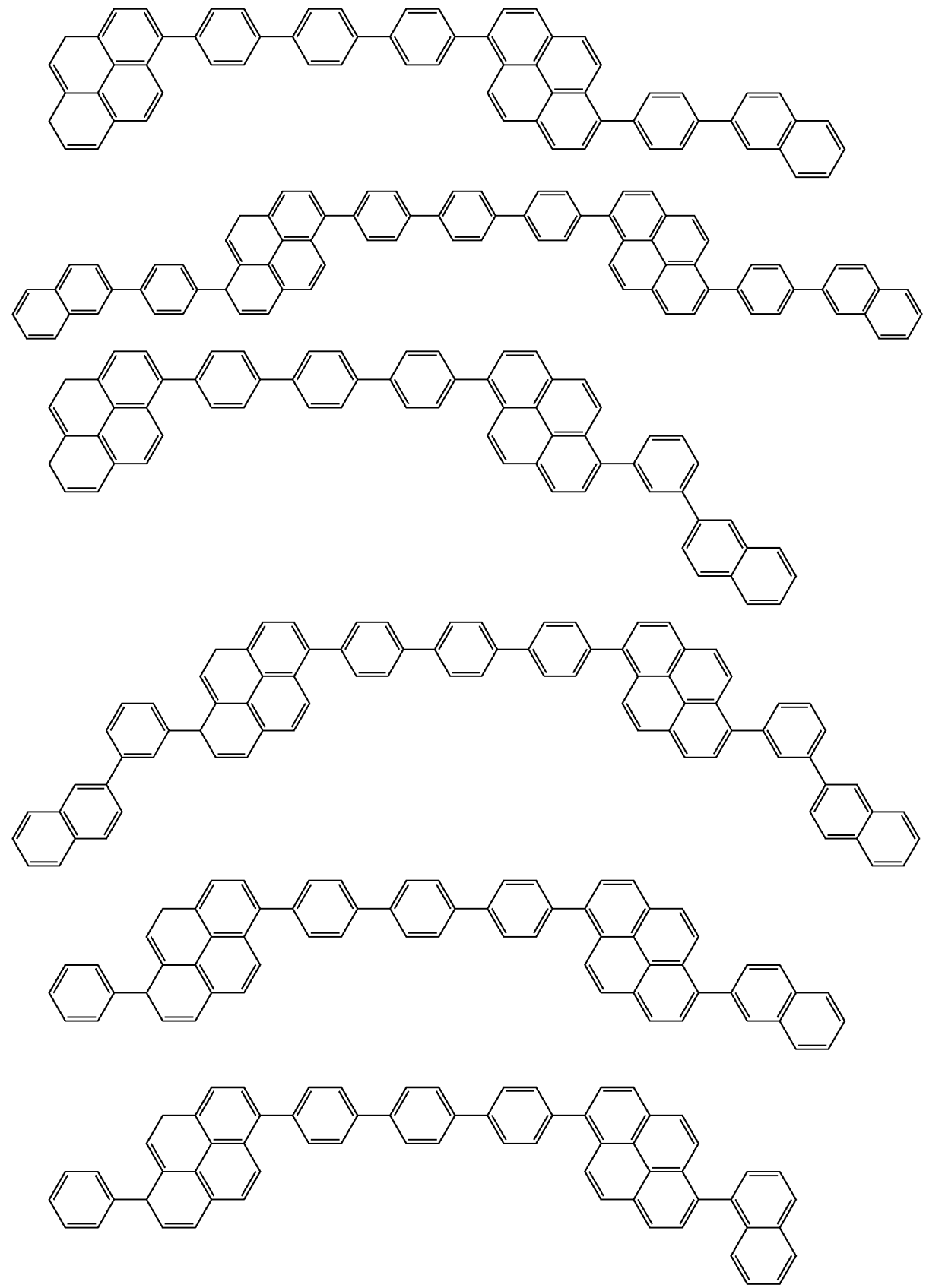

-continued
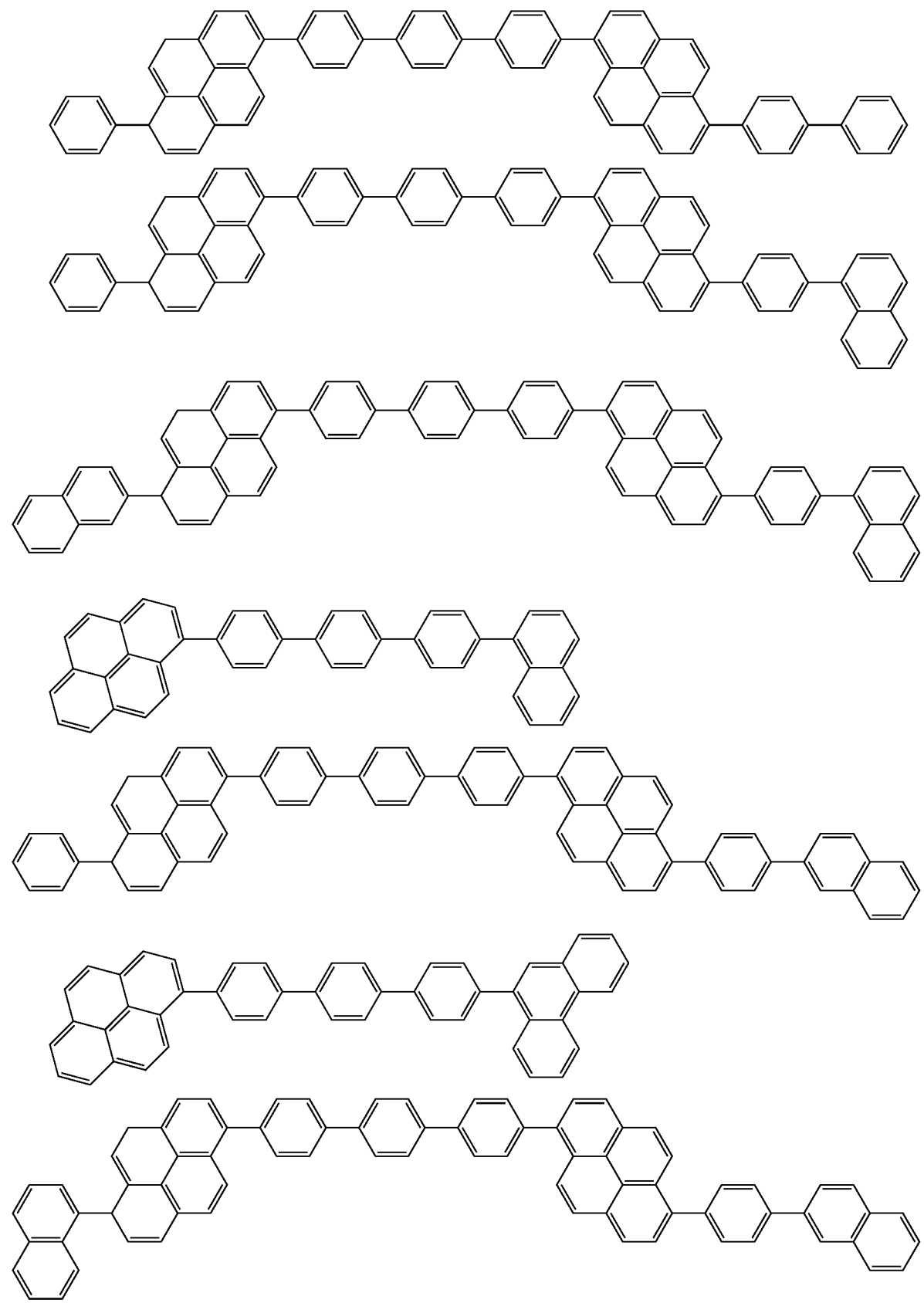

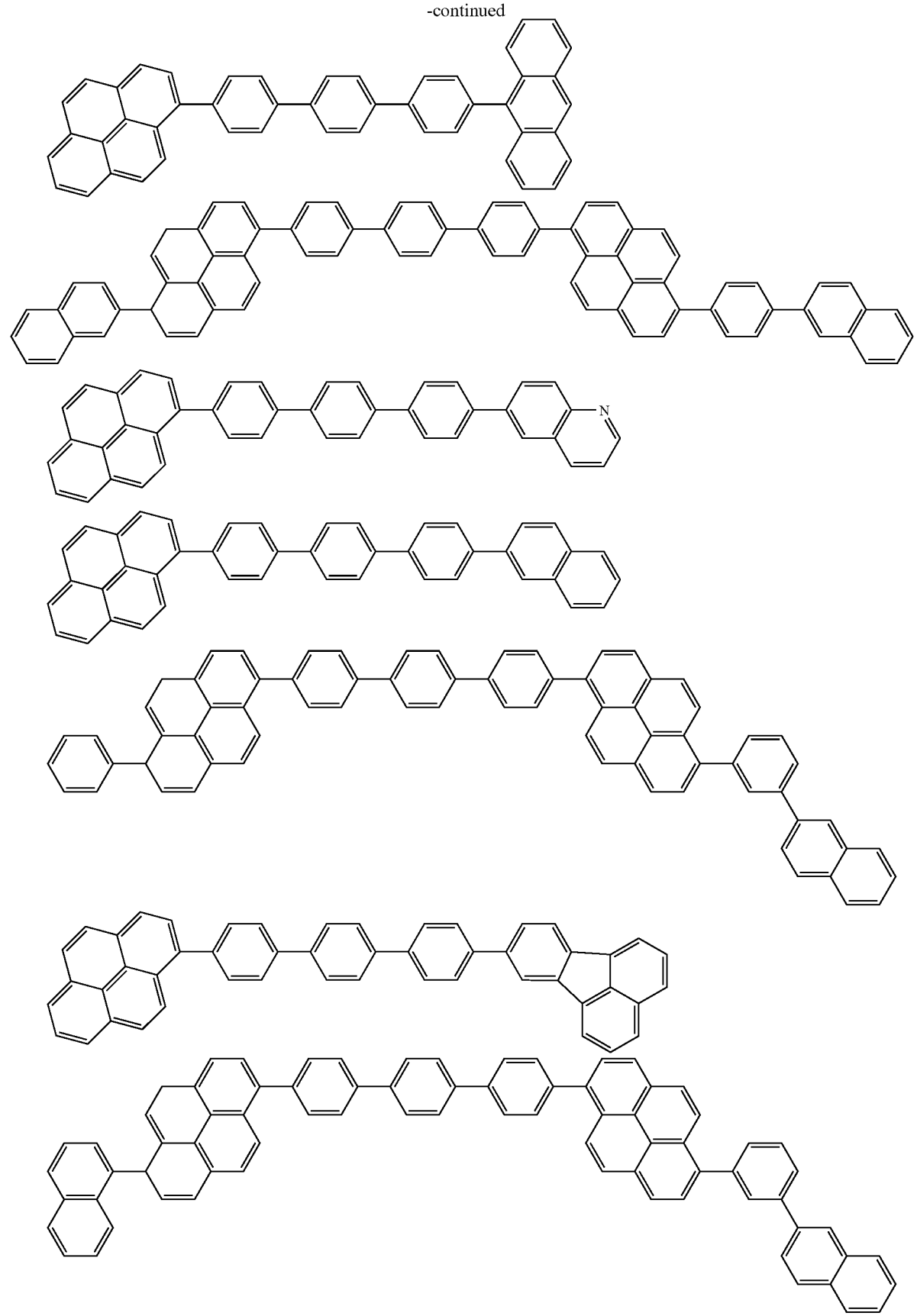

-continued
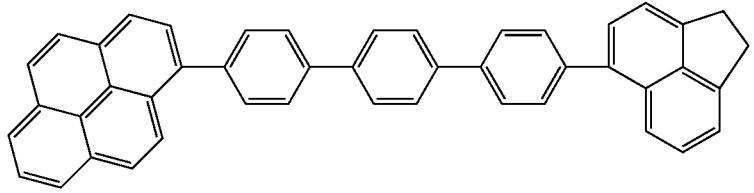
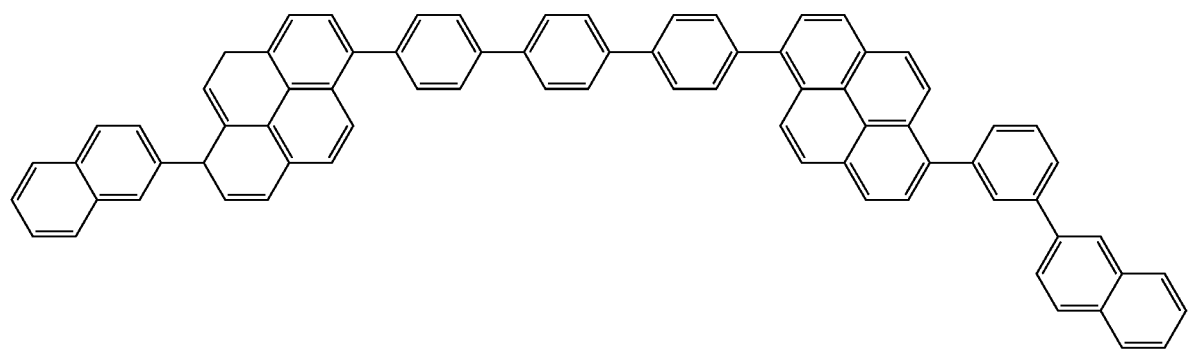
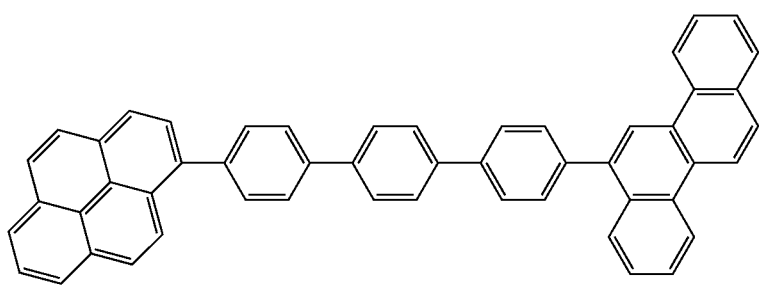
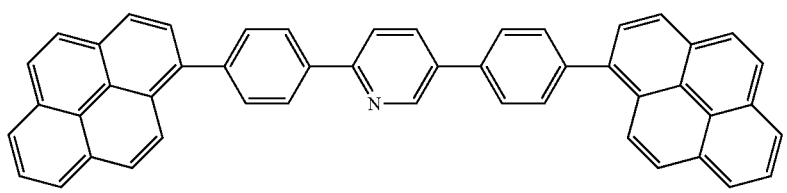
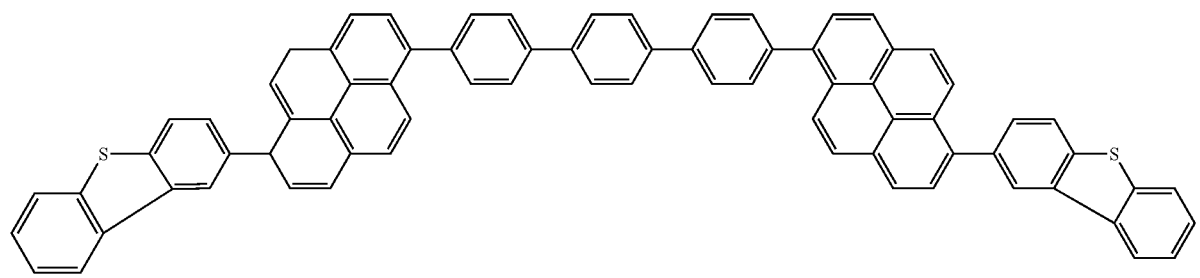
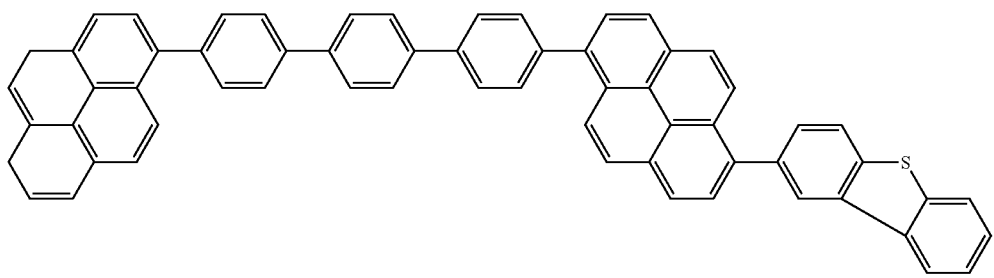

-continued
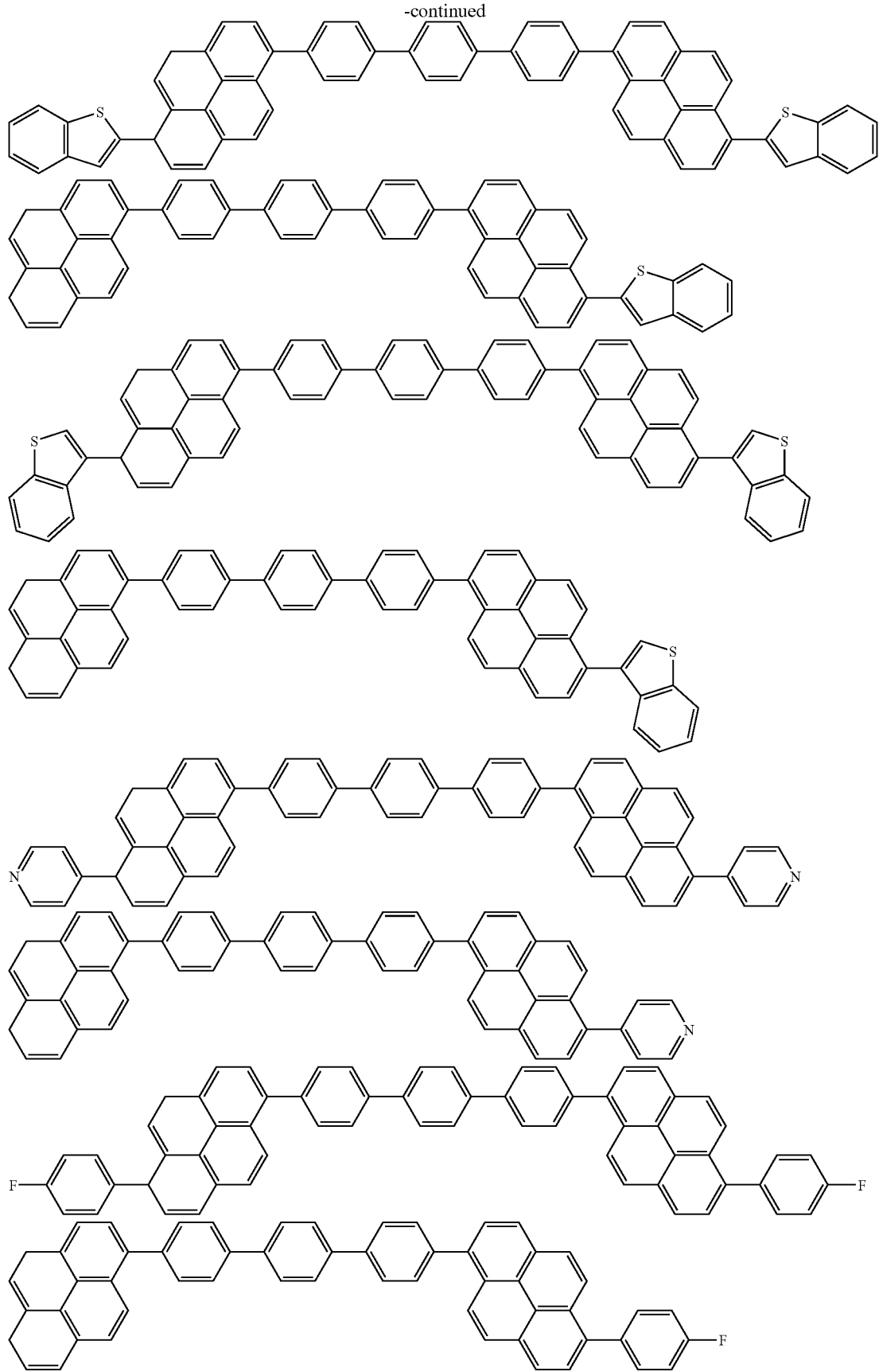

-continued
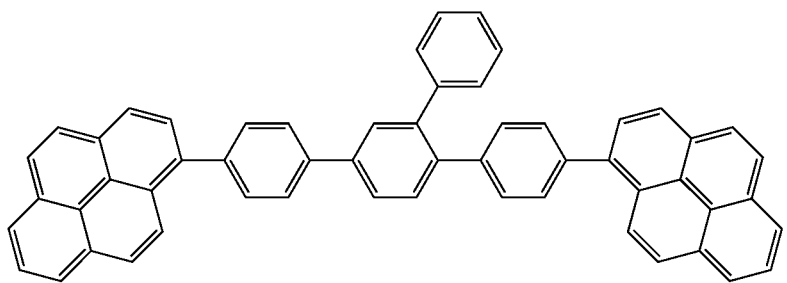
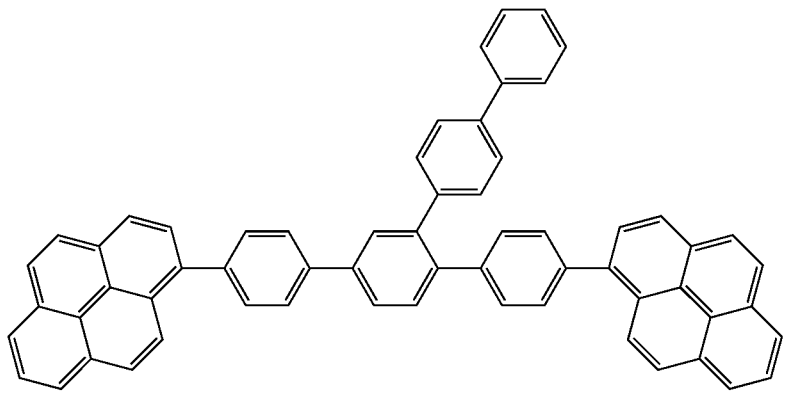
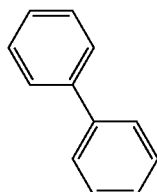
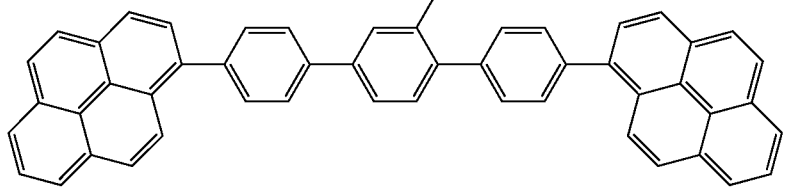
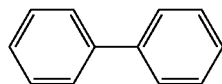
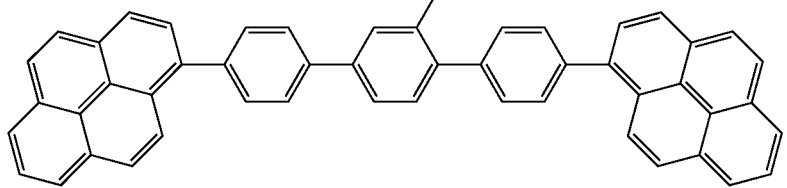
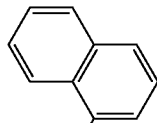
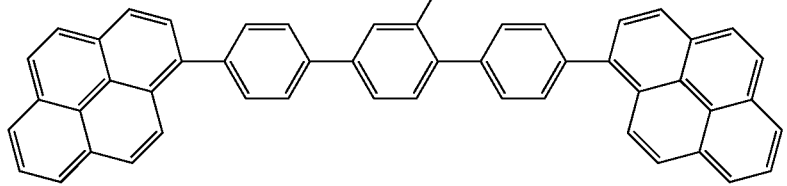

-continued
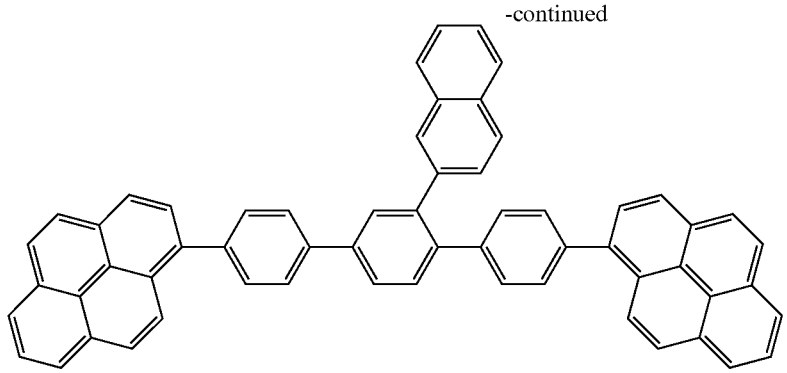
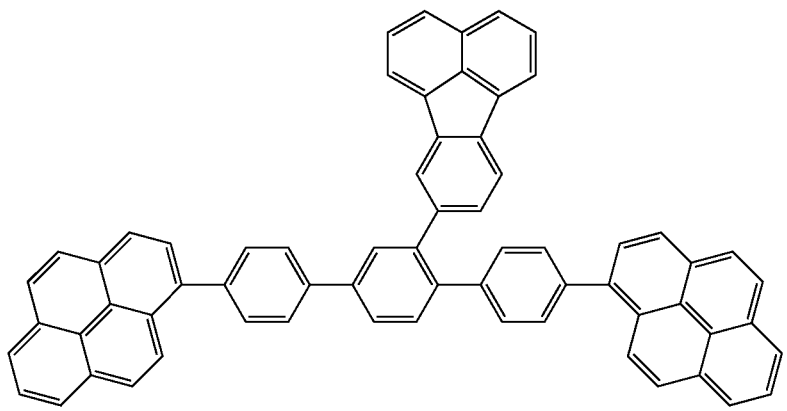
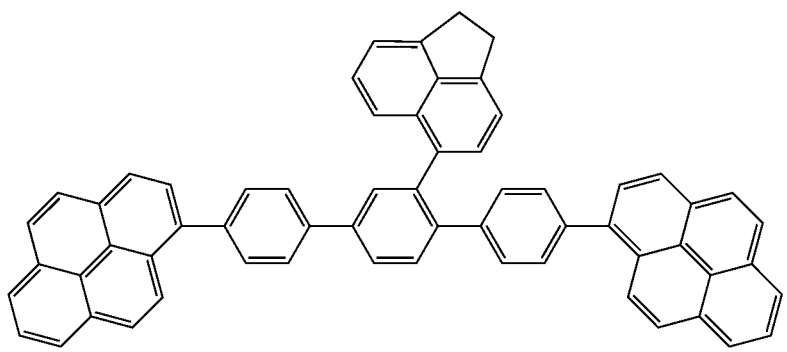
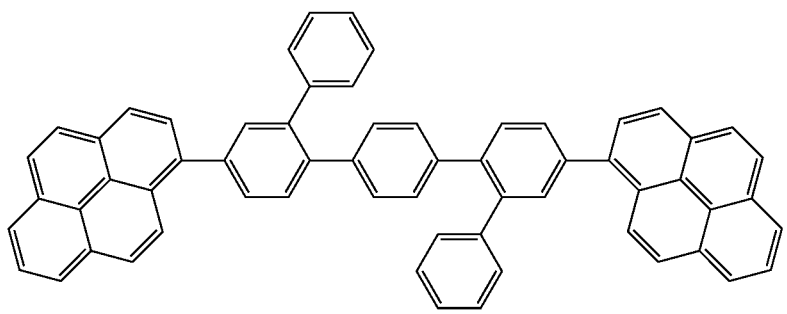
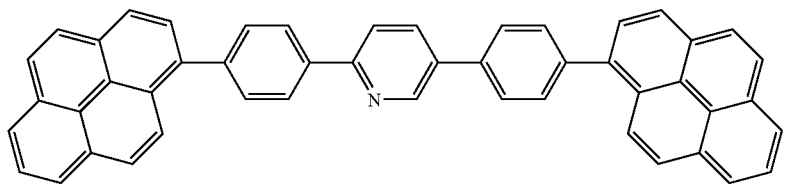

-continued
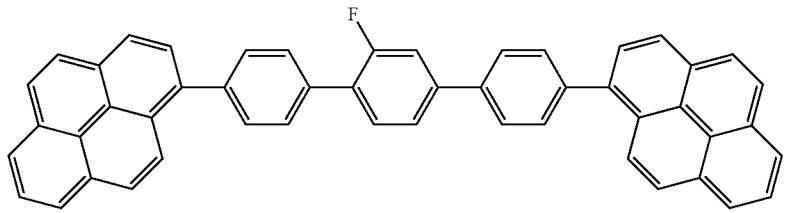
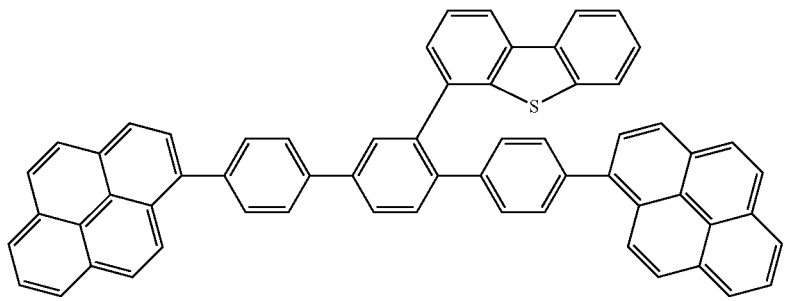
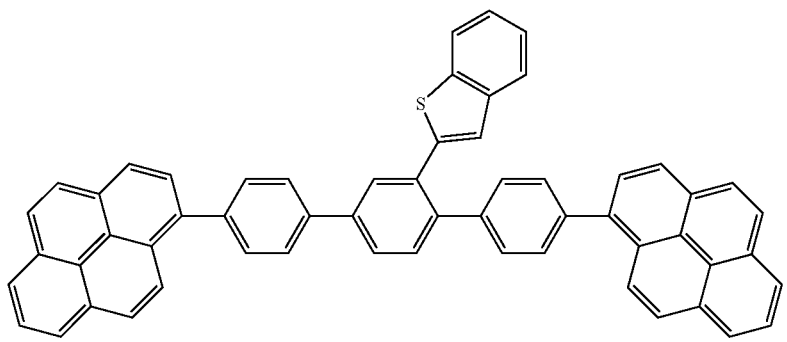
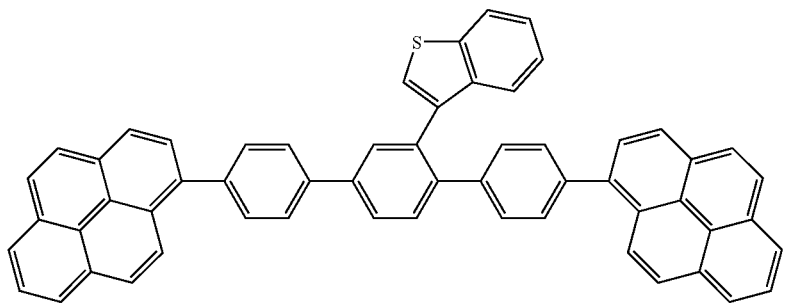
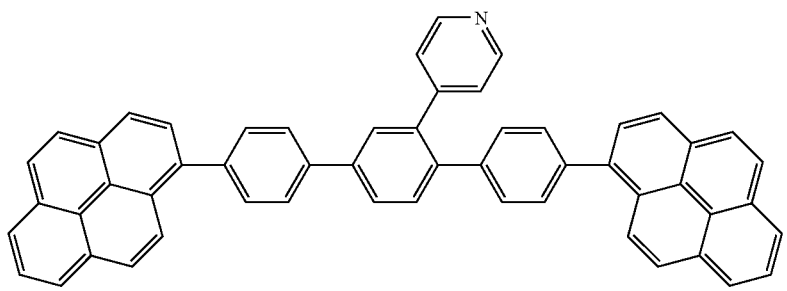

-continued
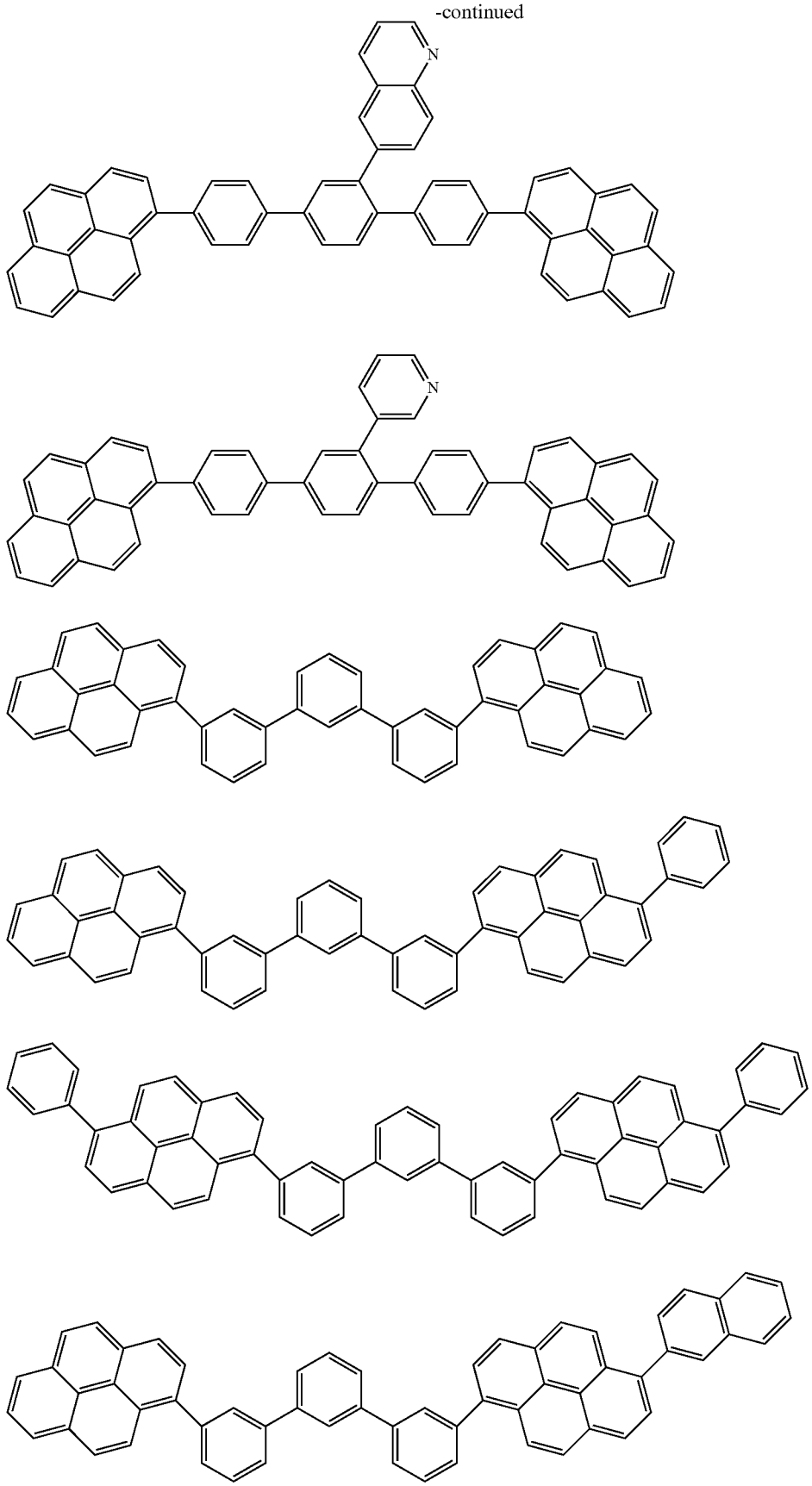

-continued
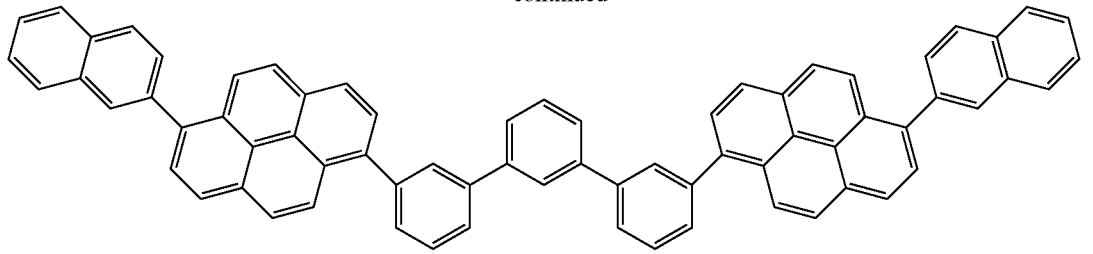
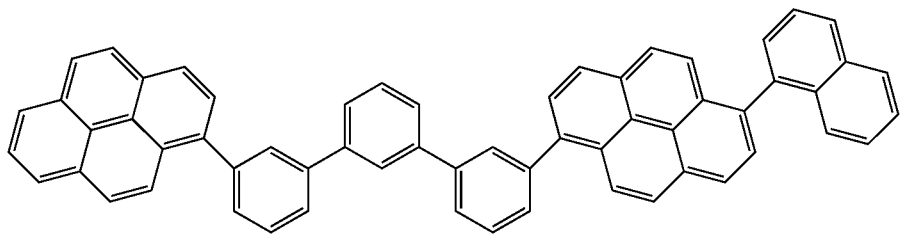
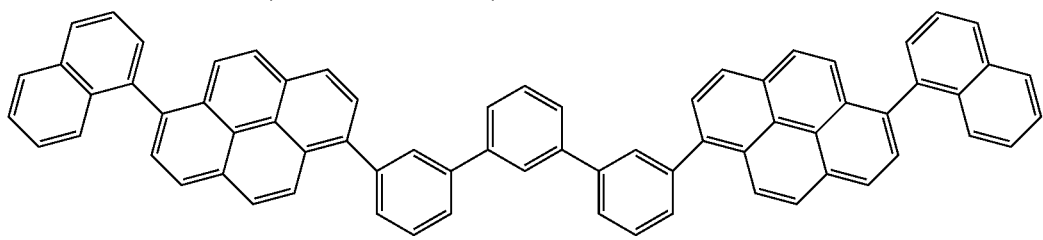
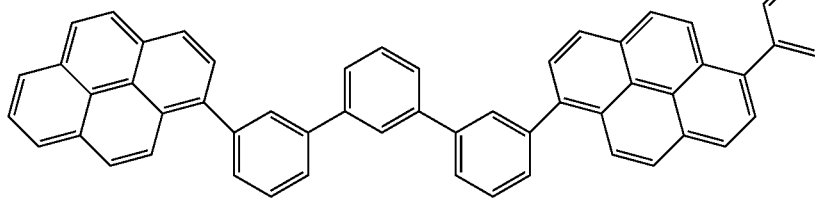
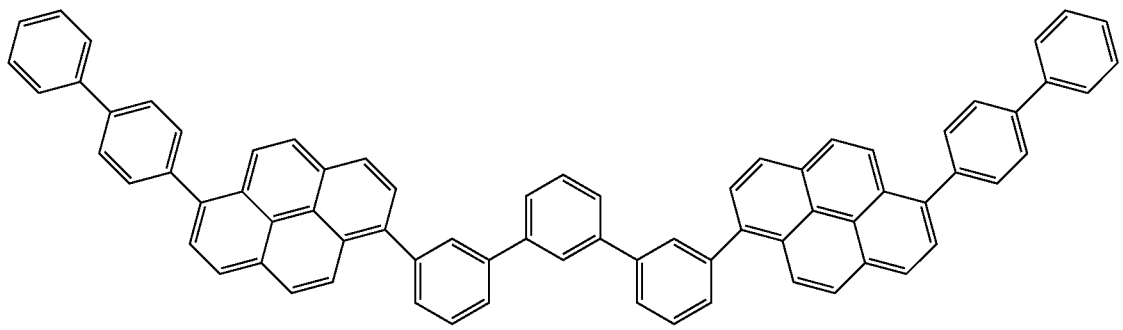
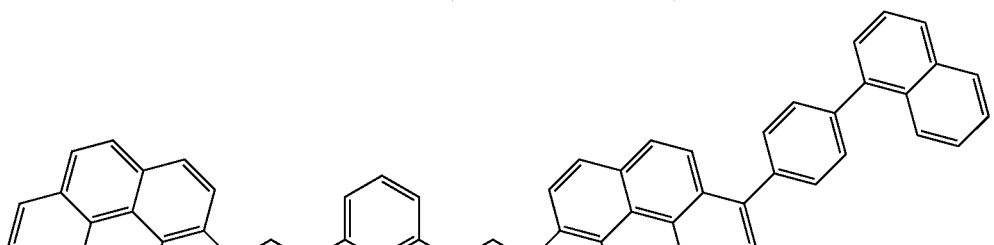

-continued
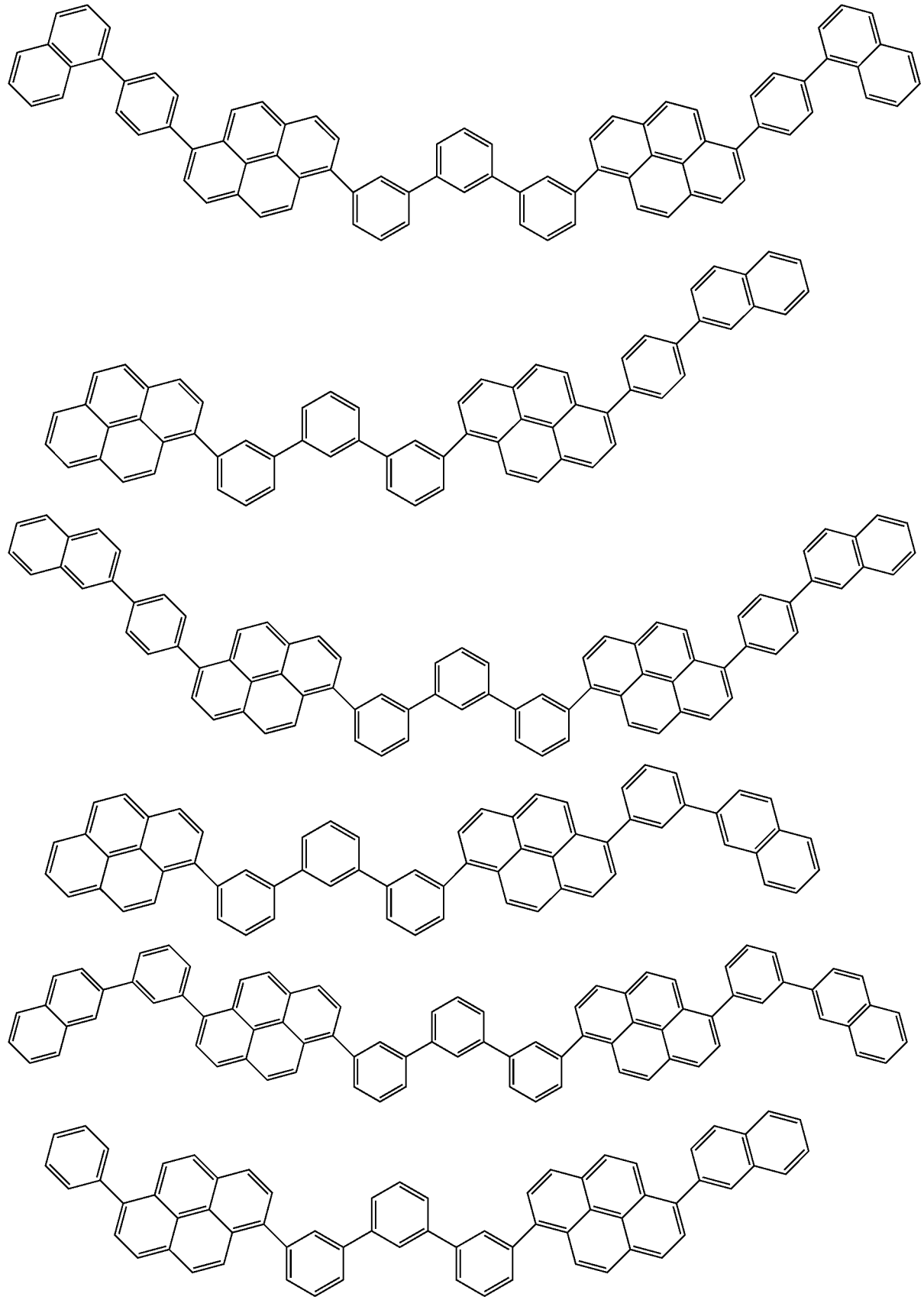

-continued
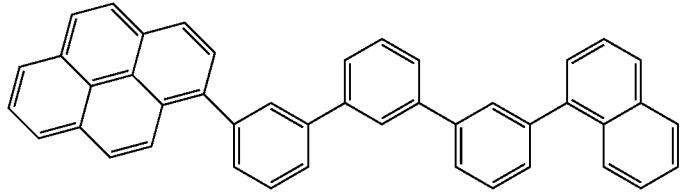
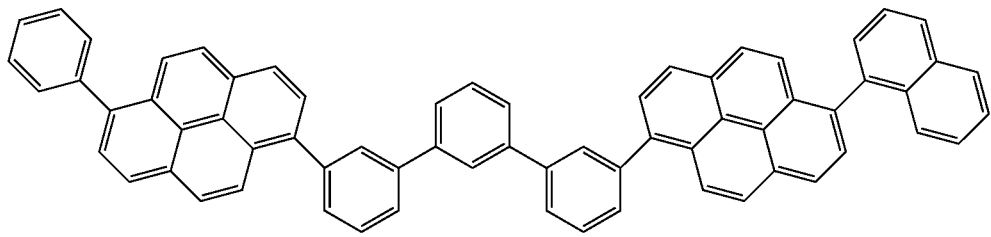
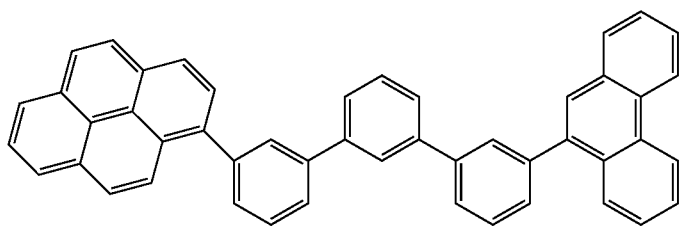
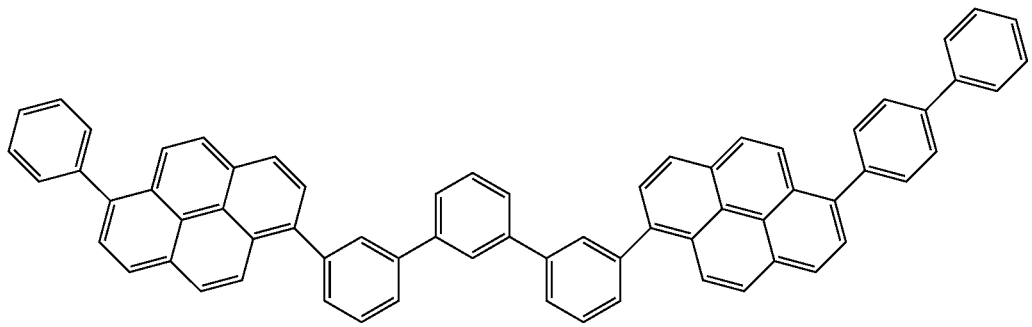
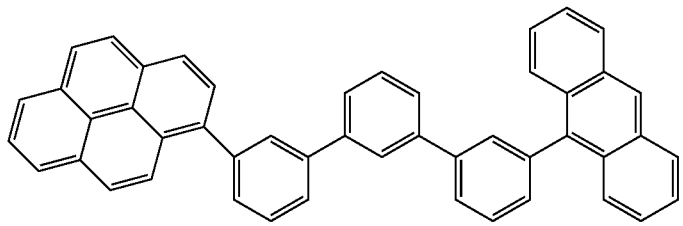
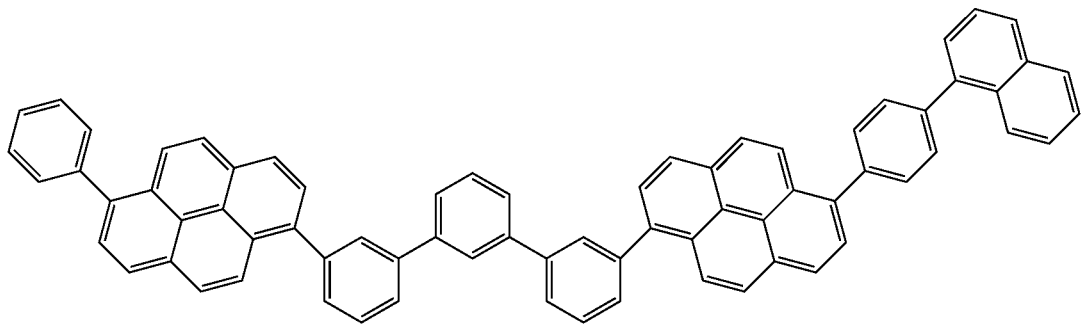

-continued
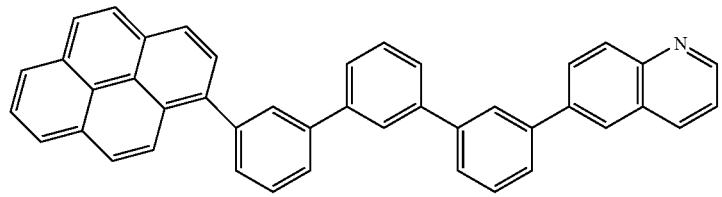
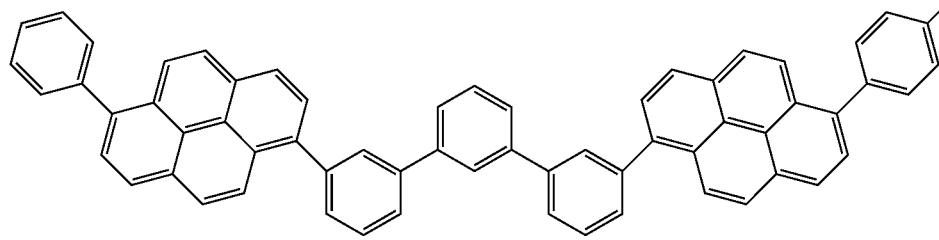
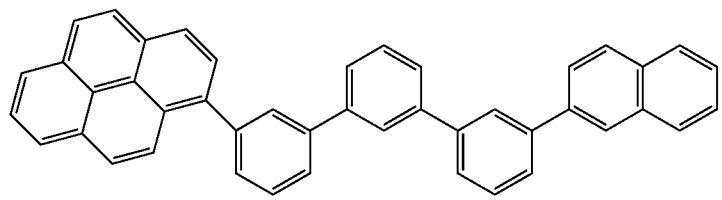
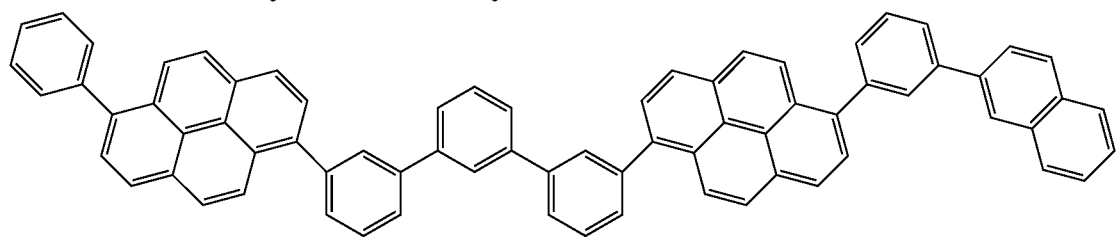
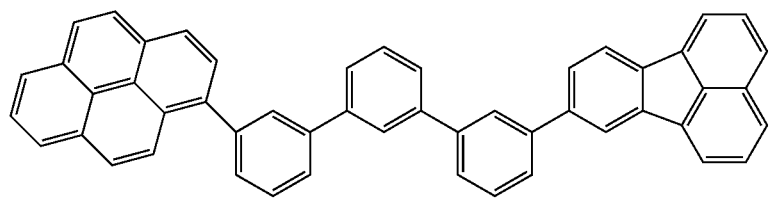
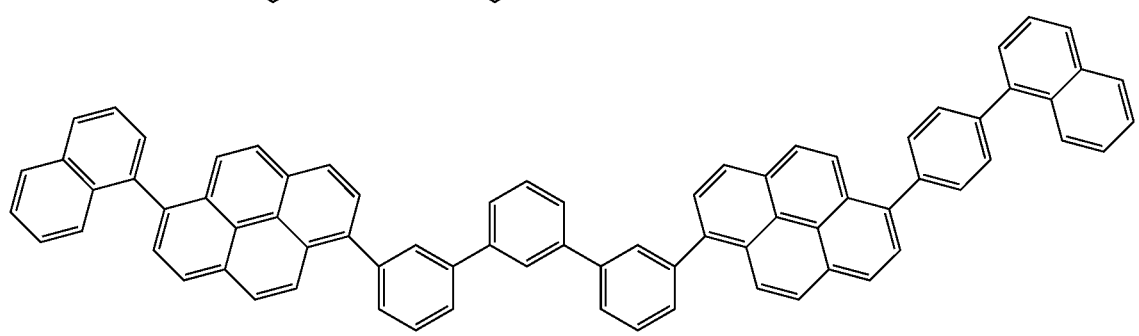
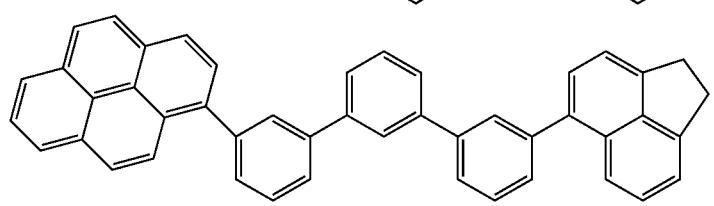

-continued
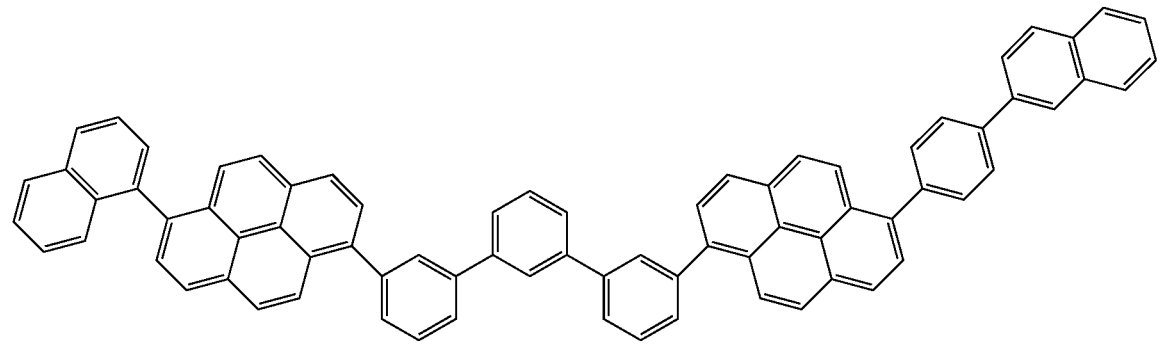
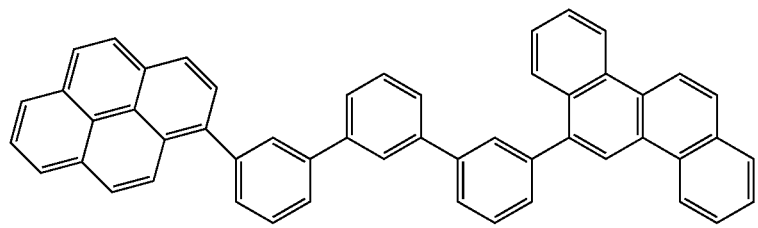
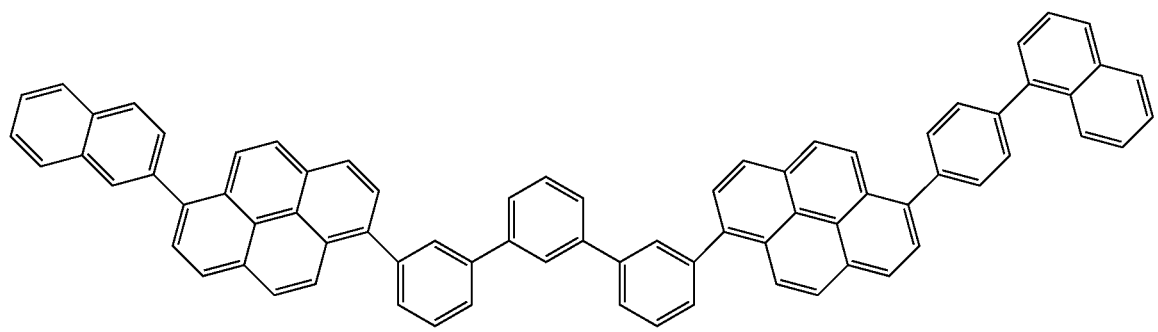
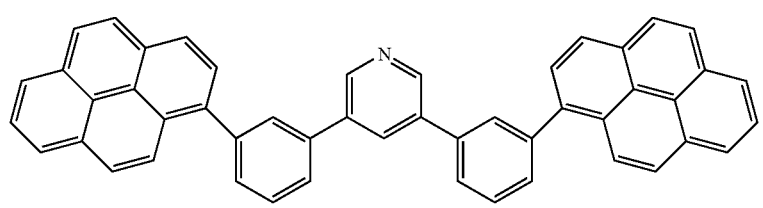
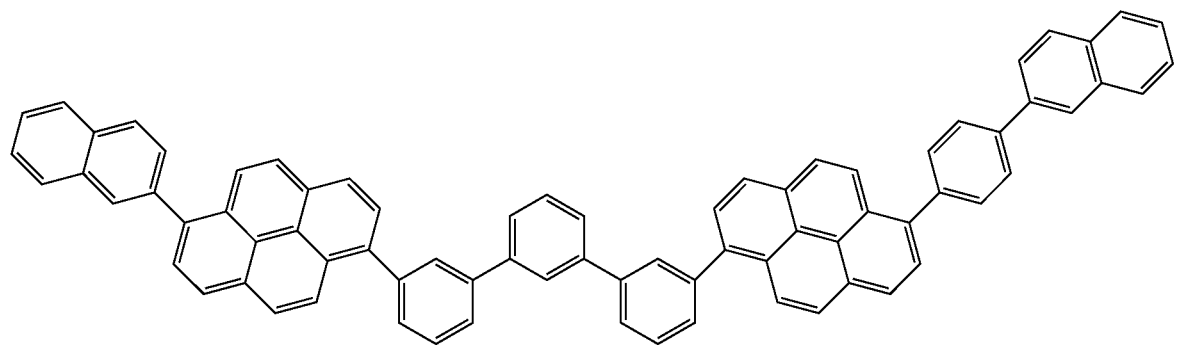
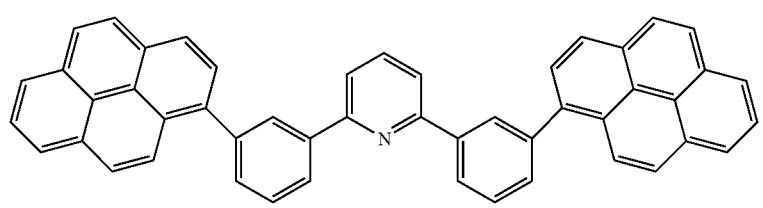

-continued
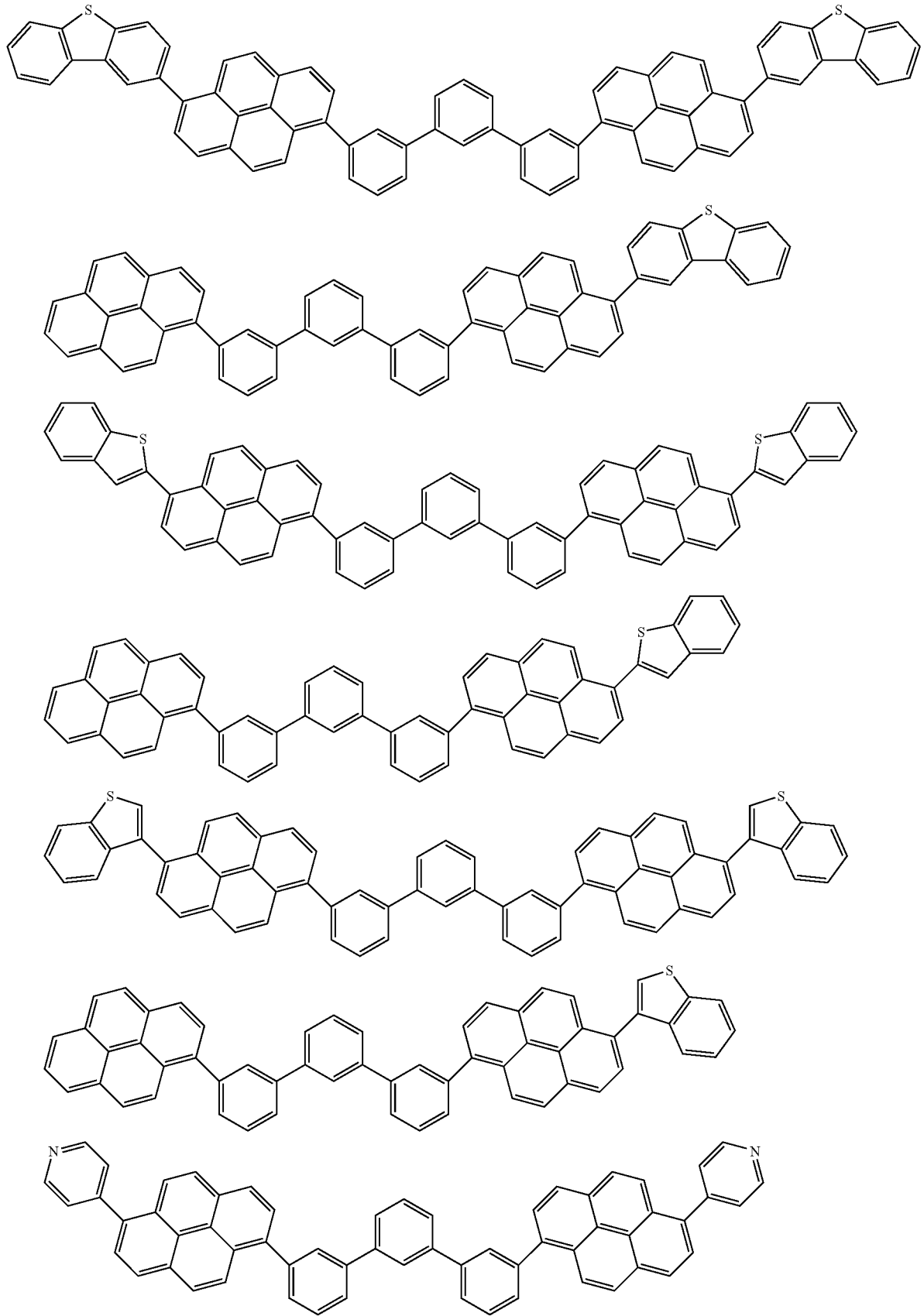

-continued
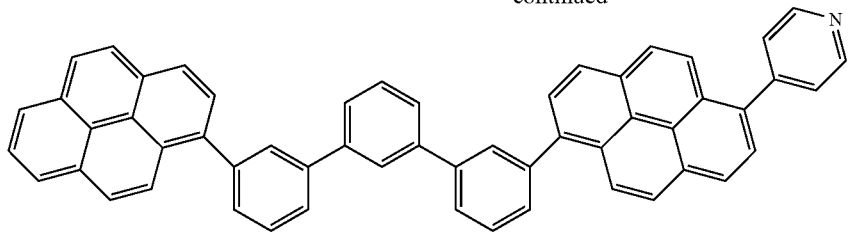
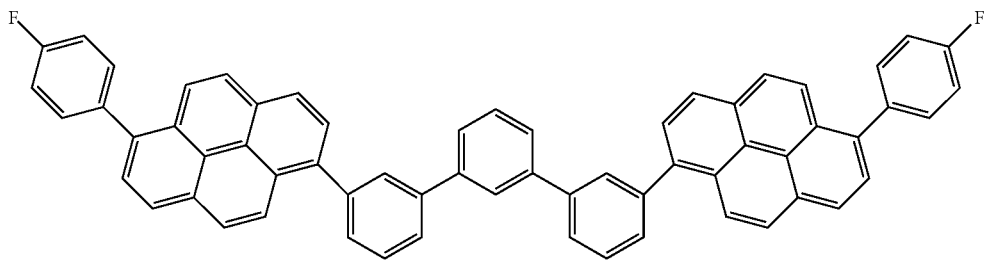
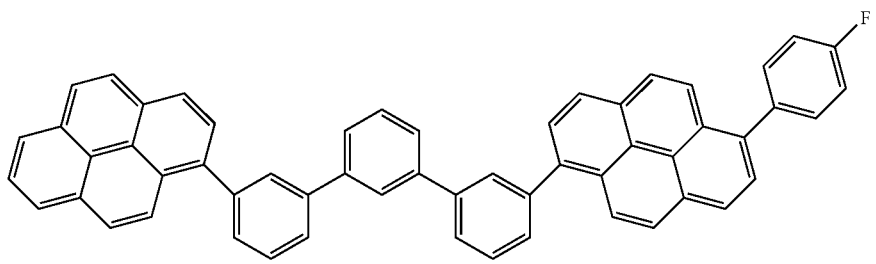
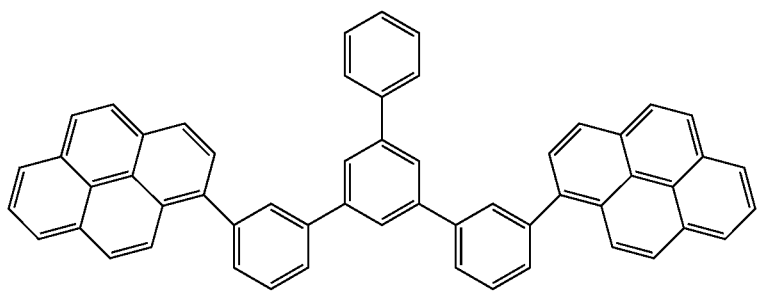
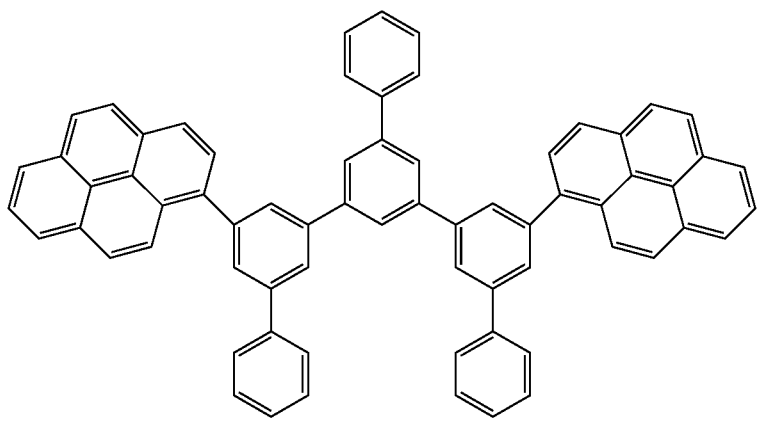

-continued
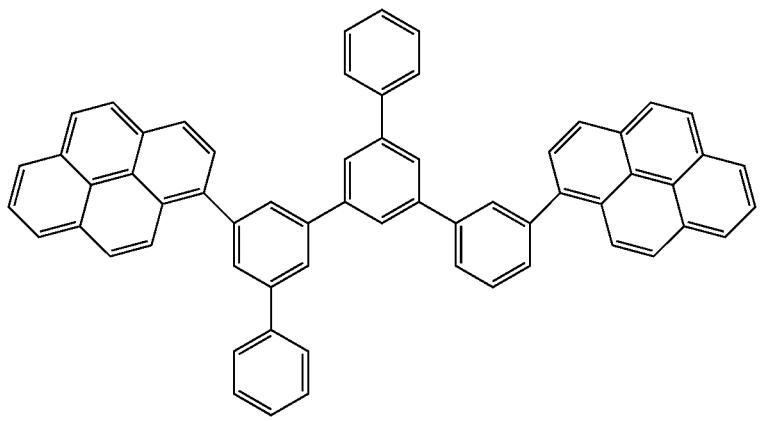
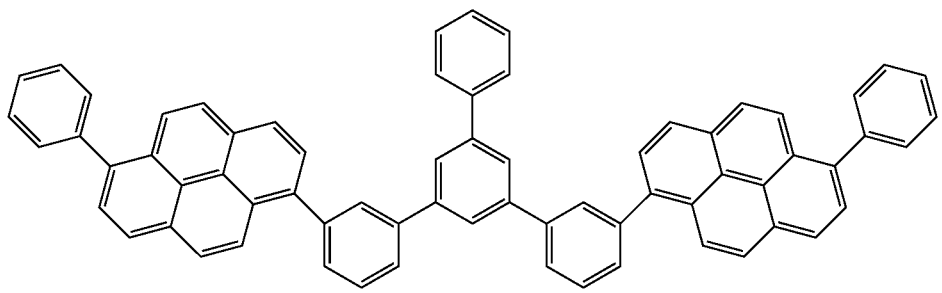
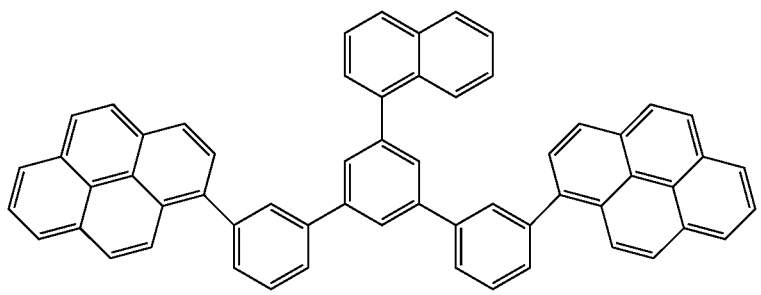
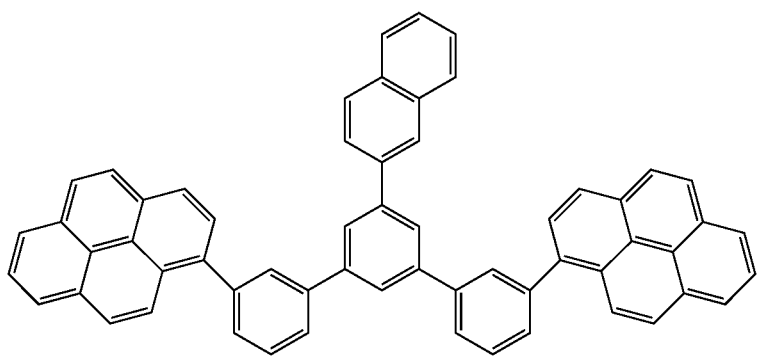
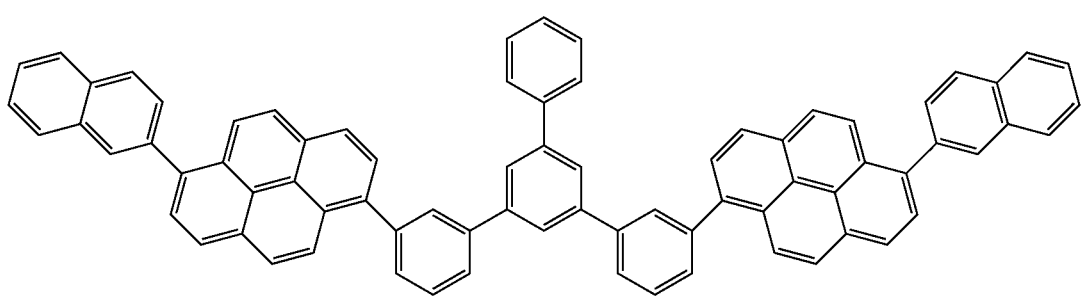

-continued
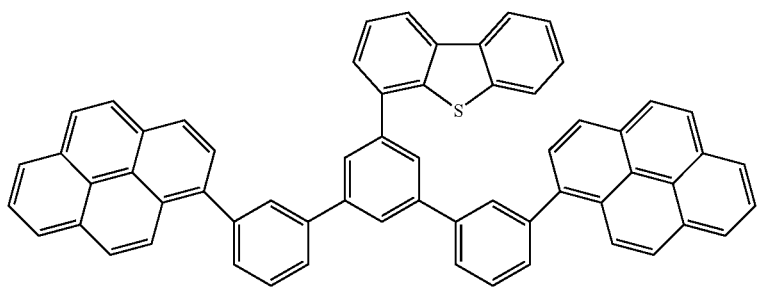
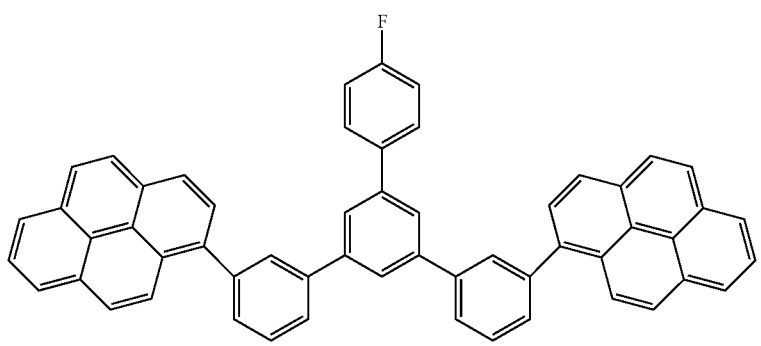
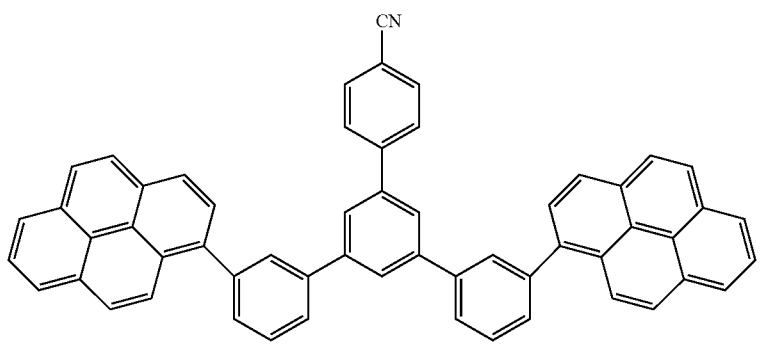
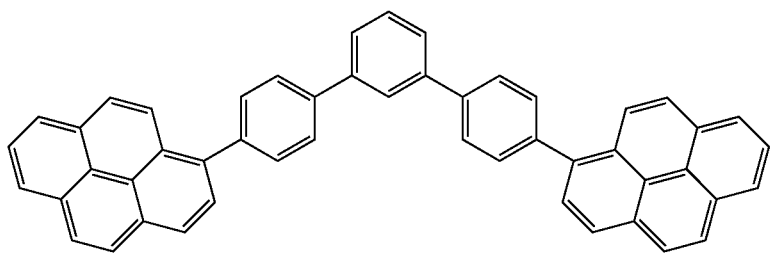
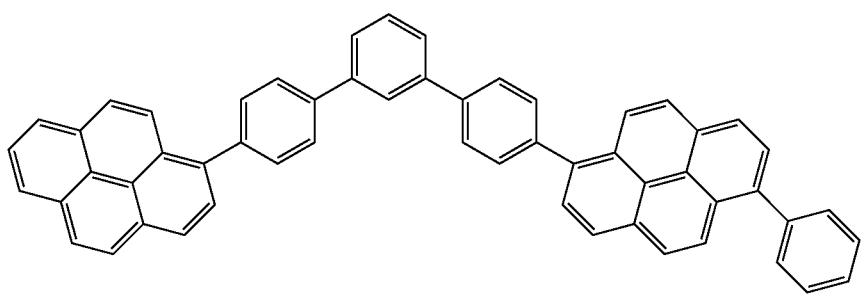

-continued
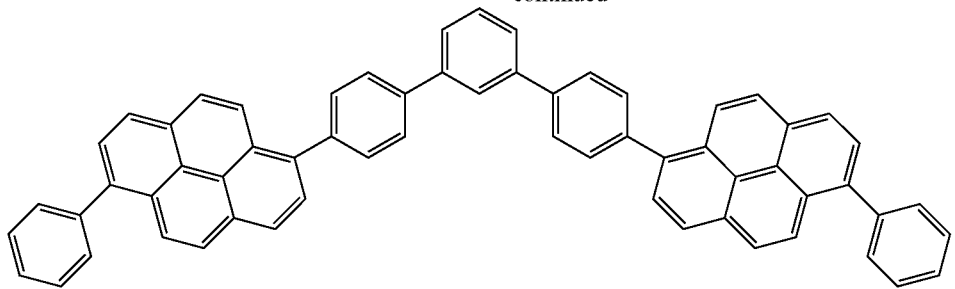
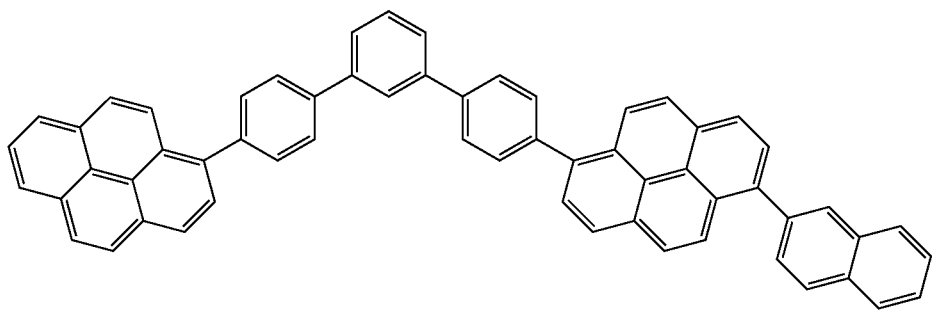
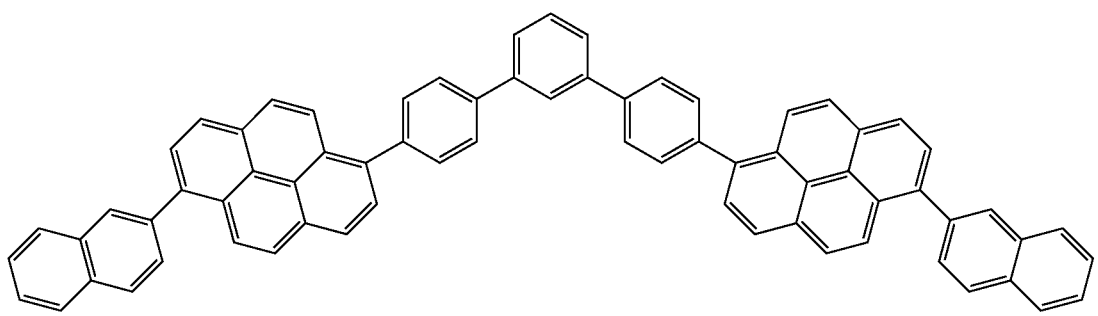
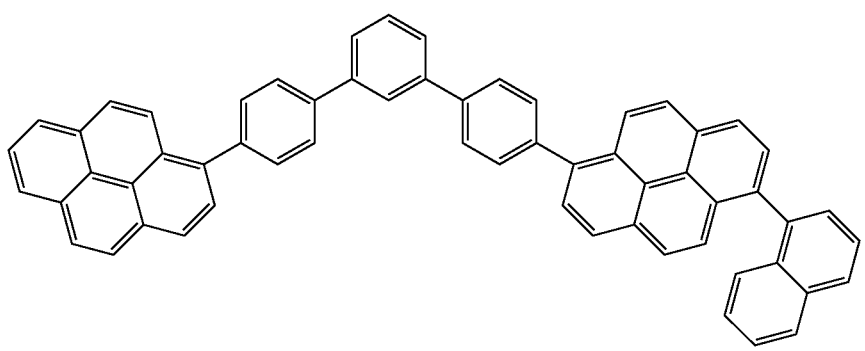
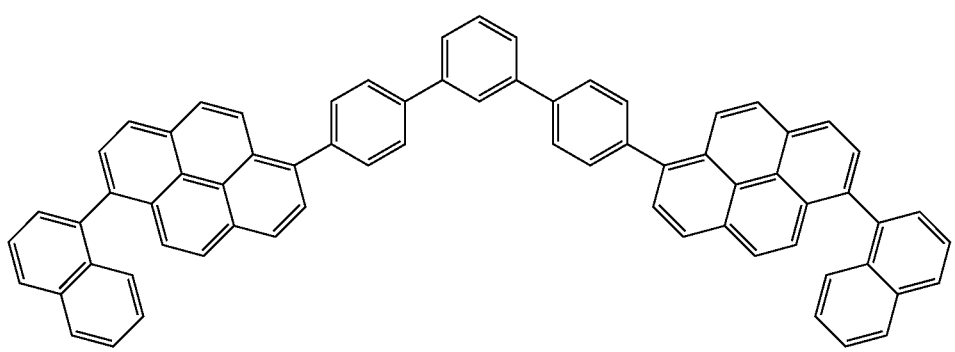

-continued
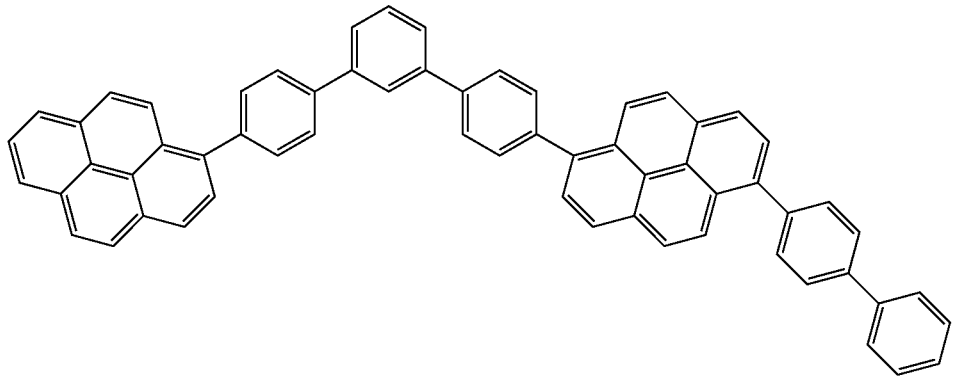
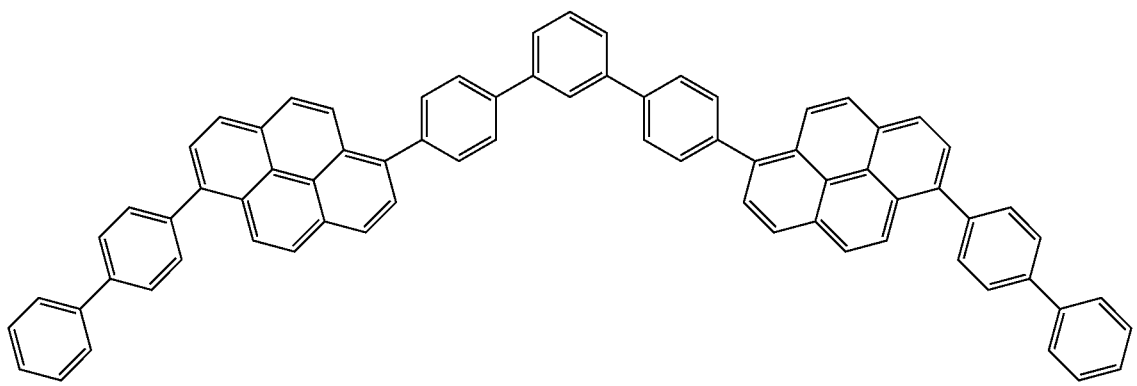
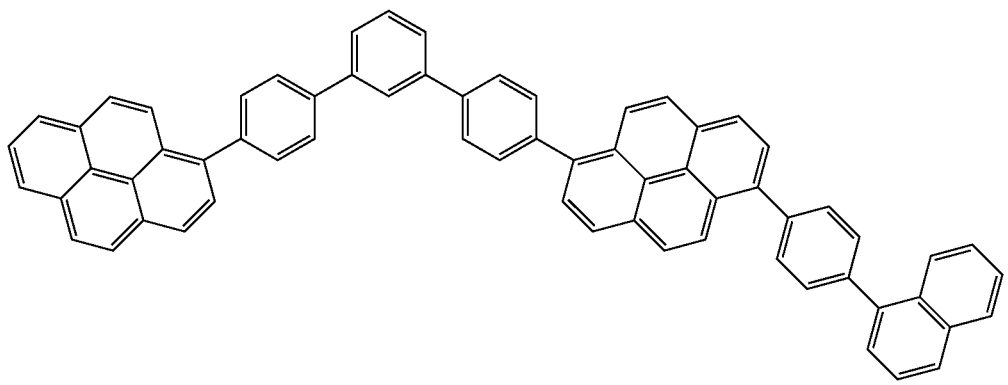
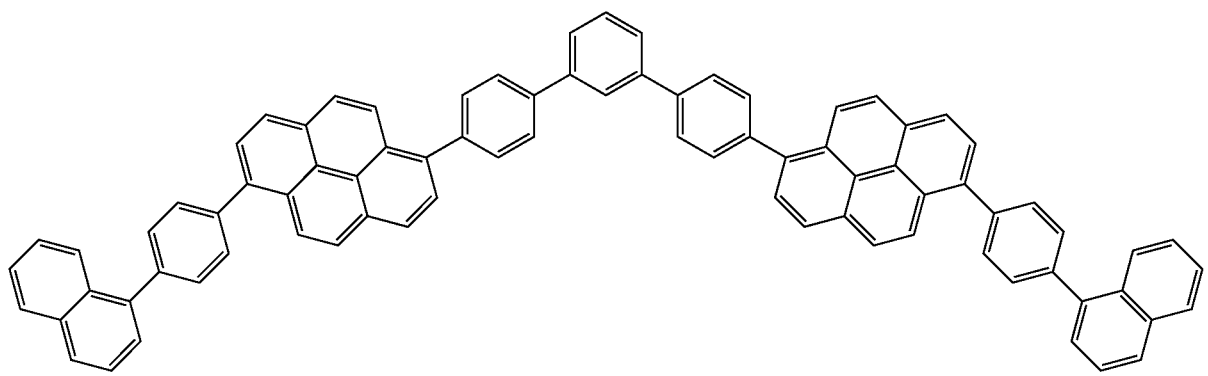

-continued
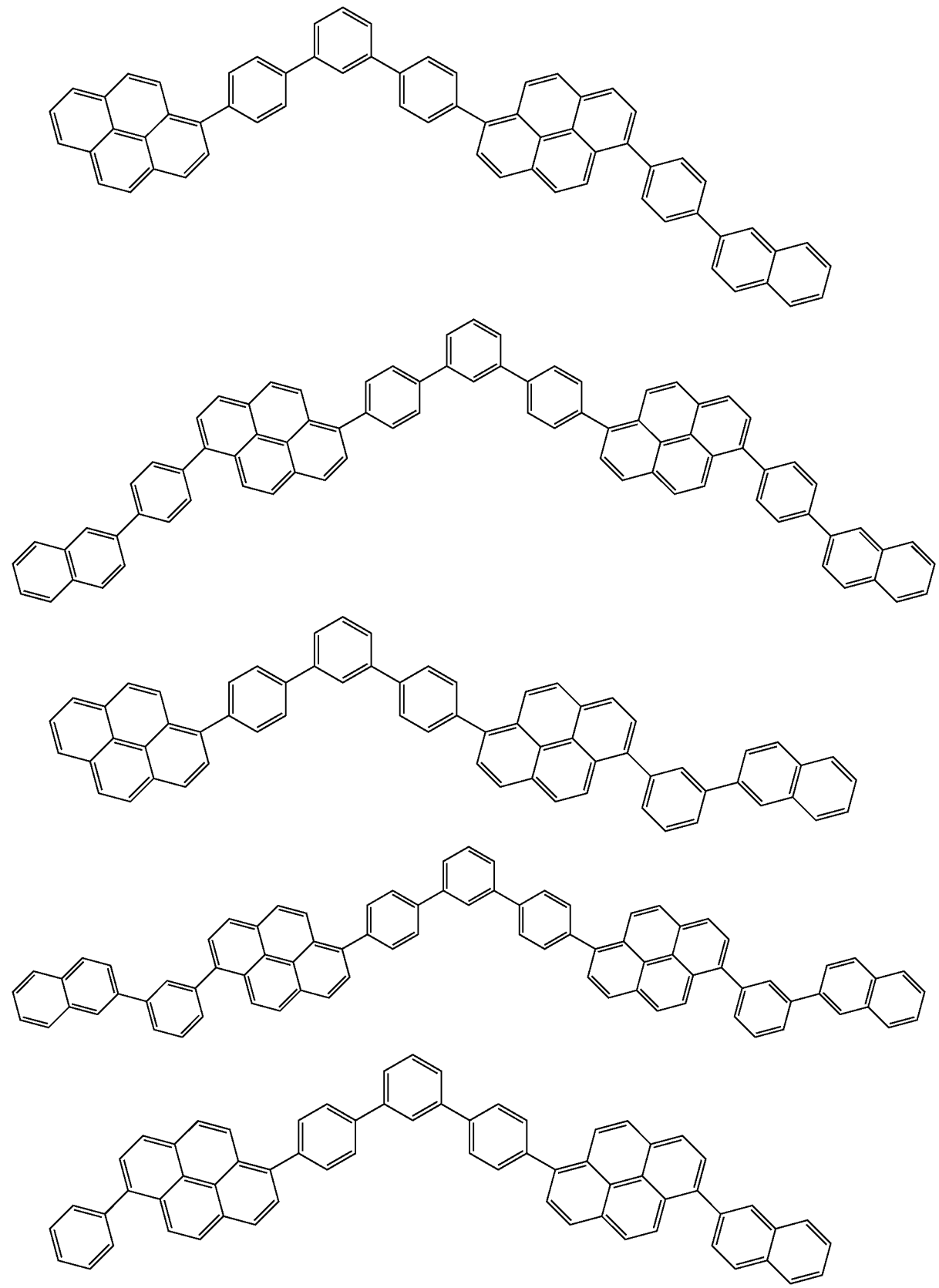

-continued
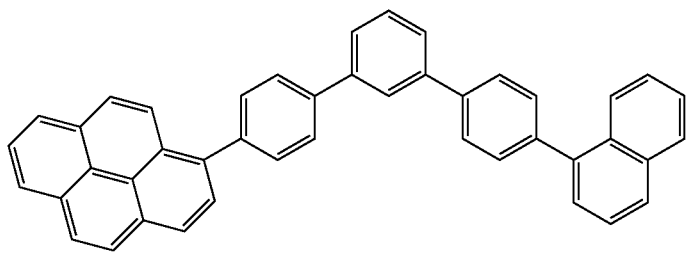
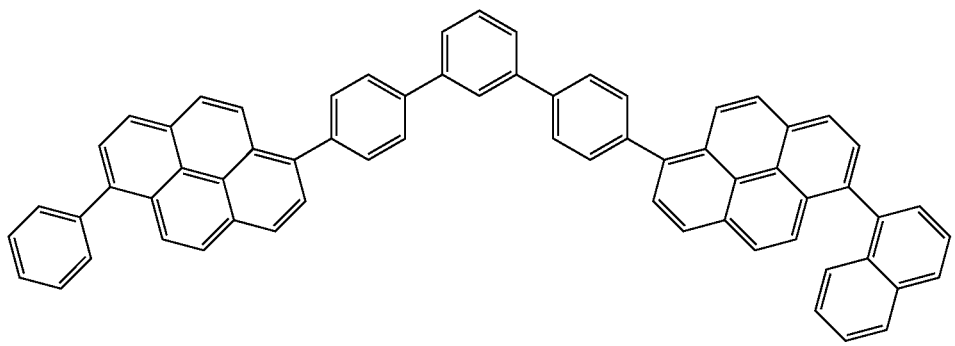
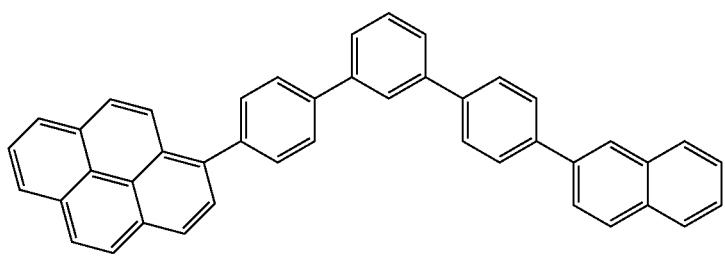
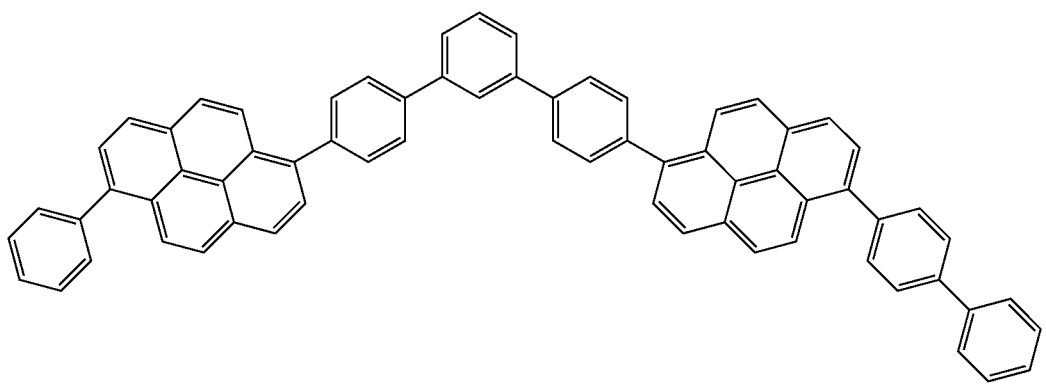
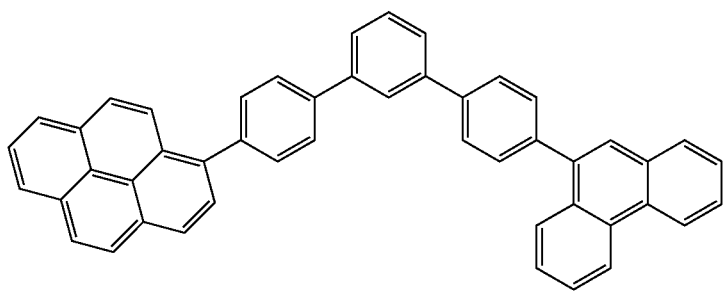

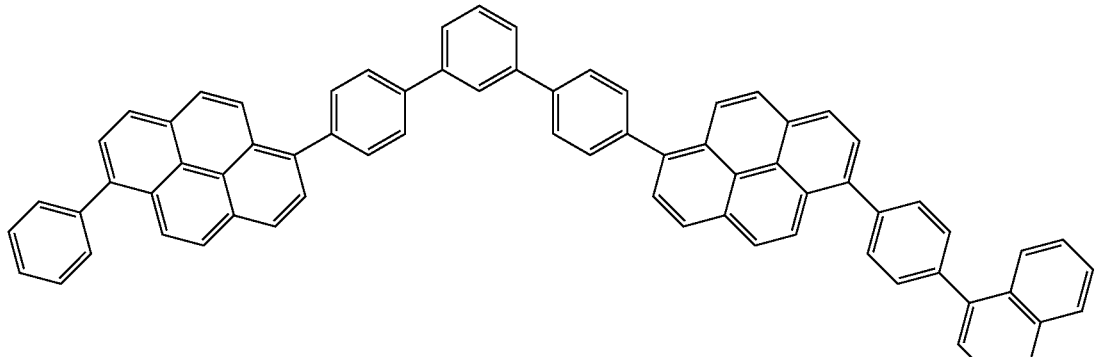

-continued
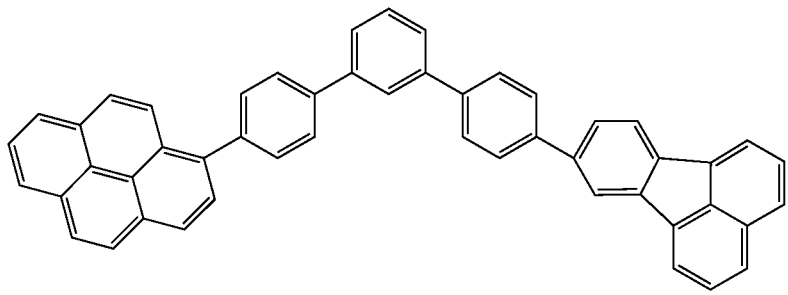
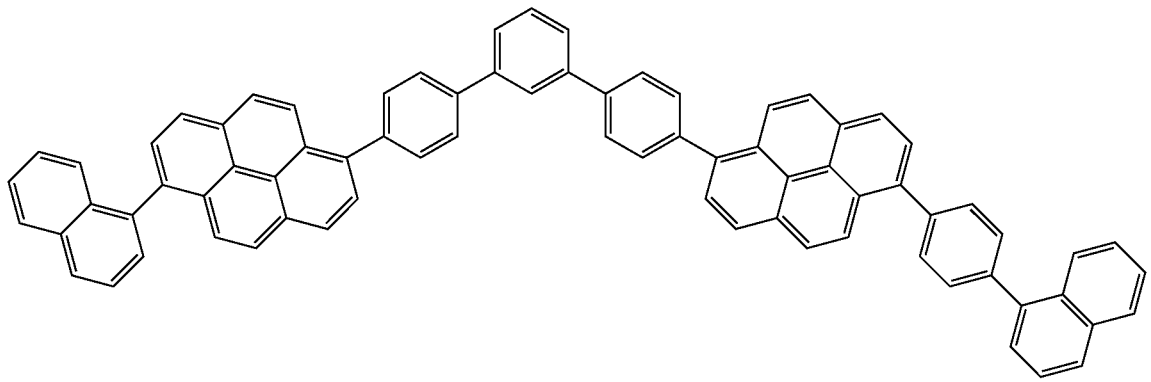
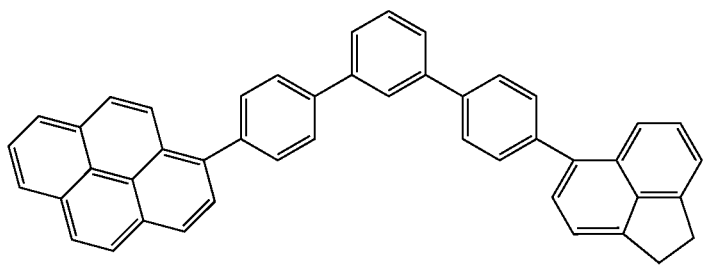
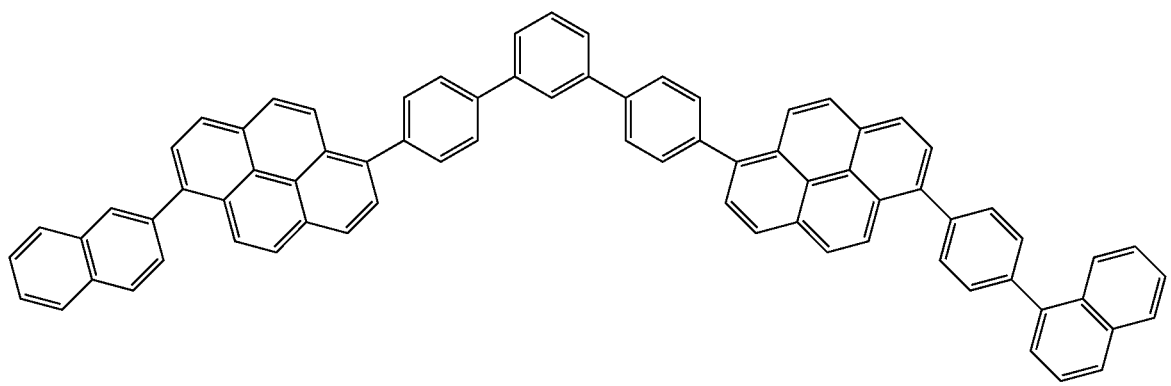
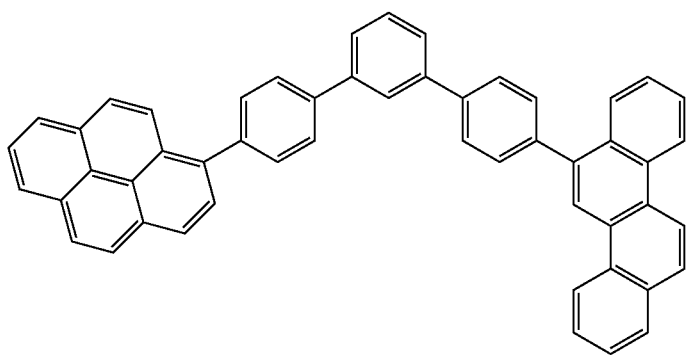

-continued
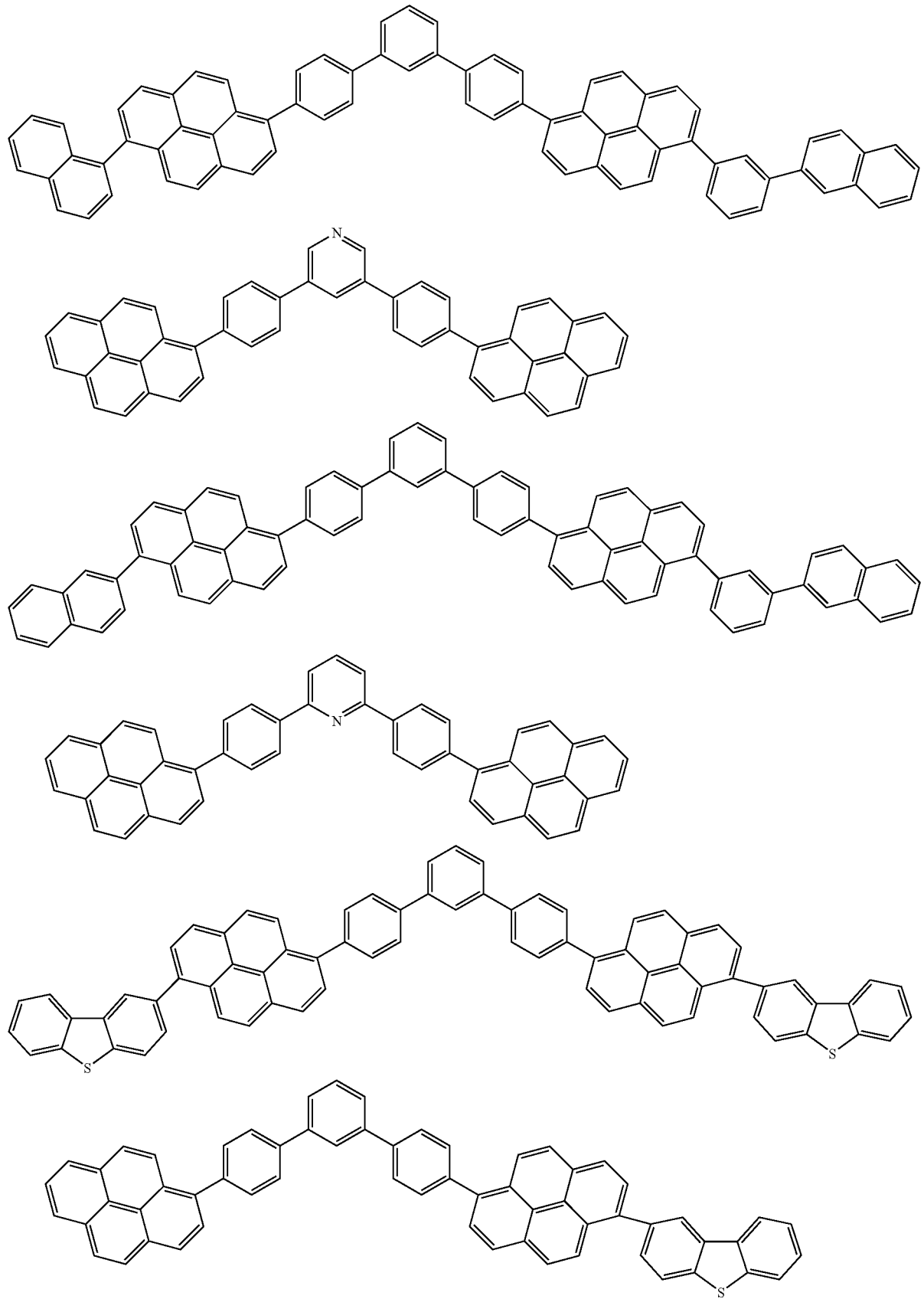

-continued
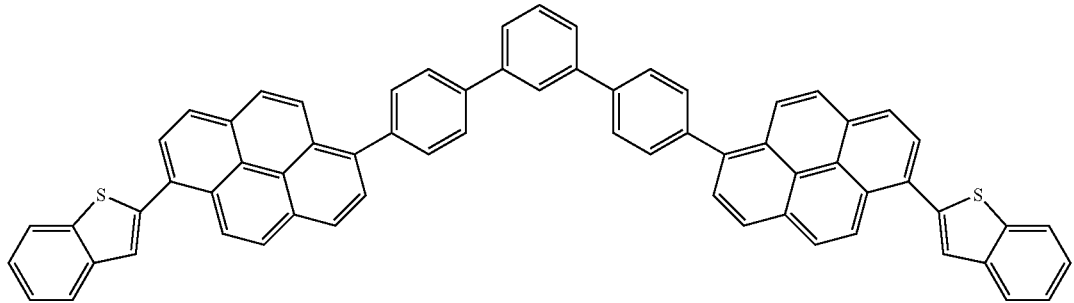
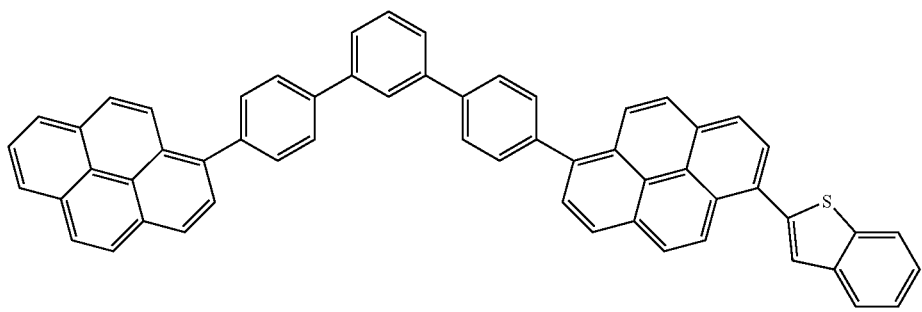
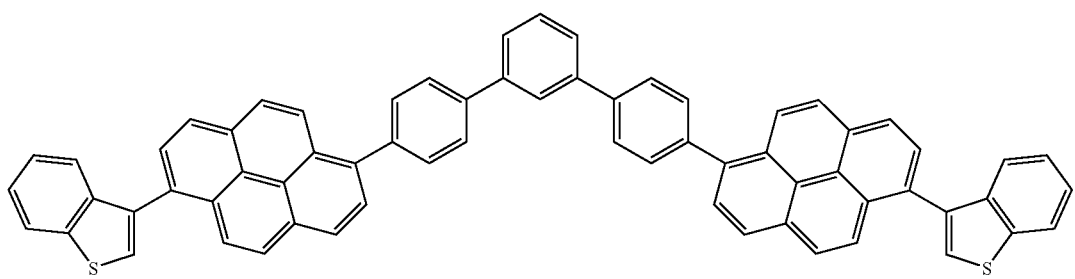
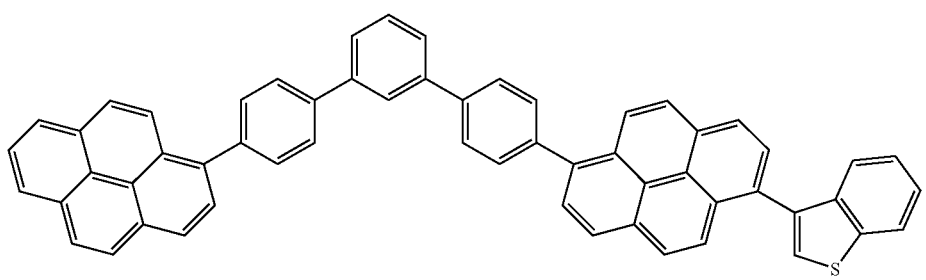
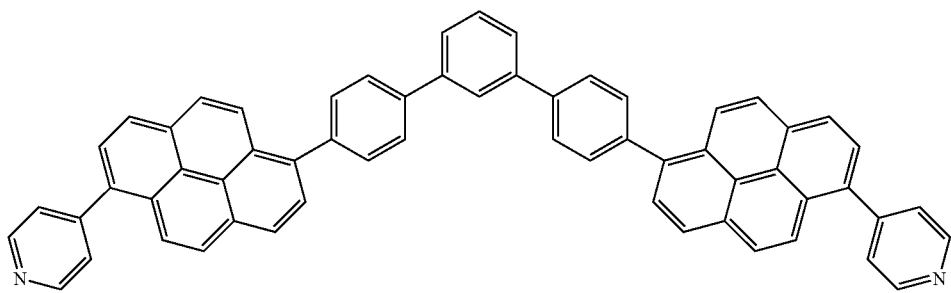

-continued
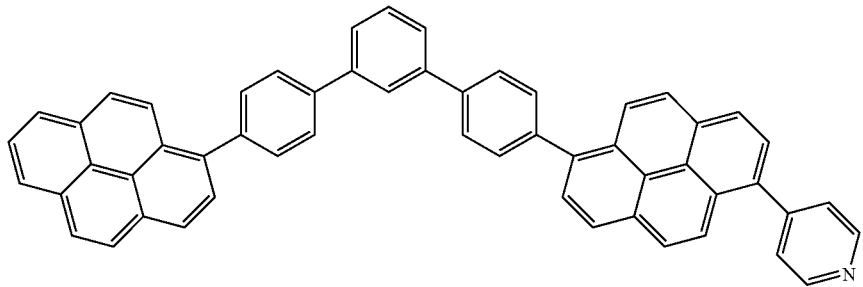
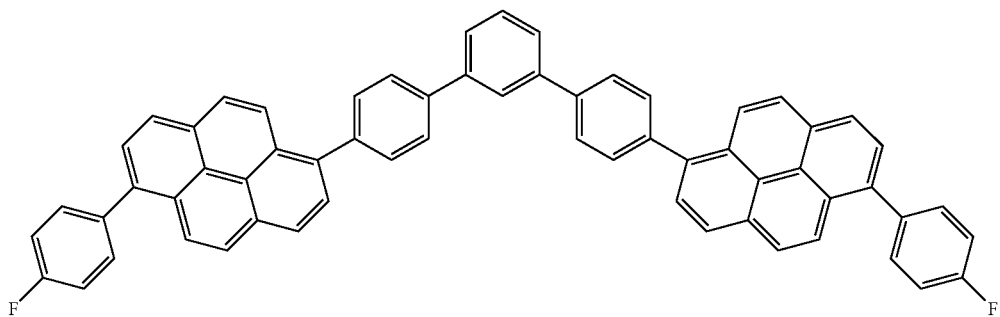
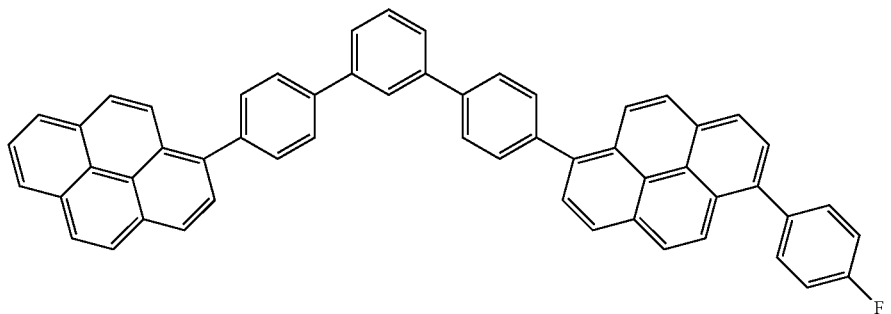
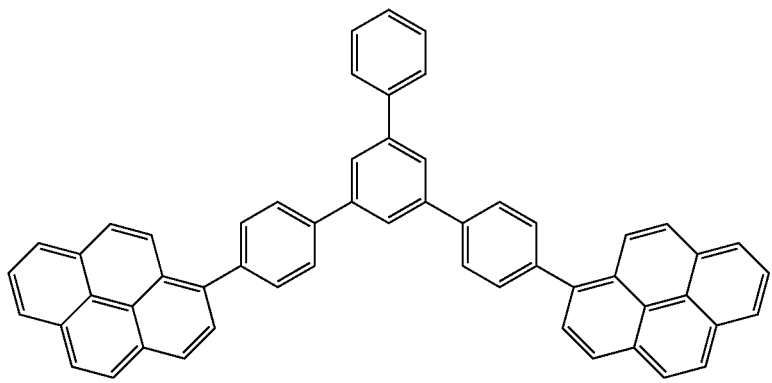
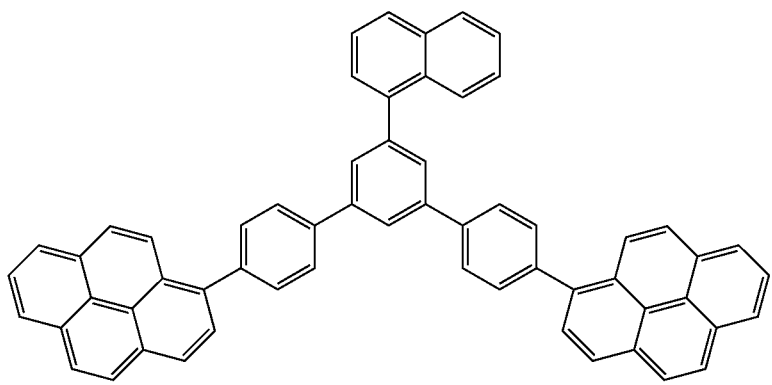

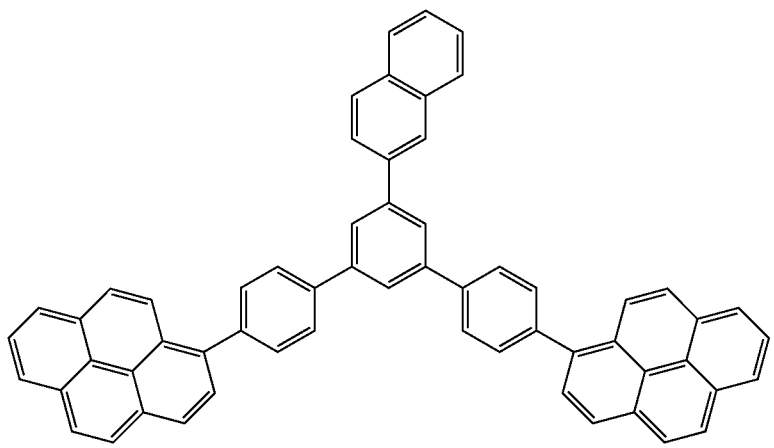
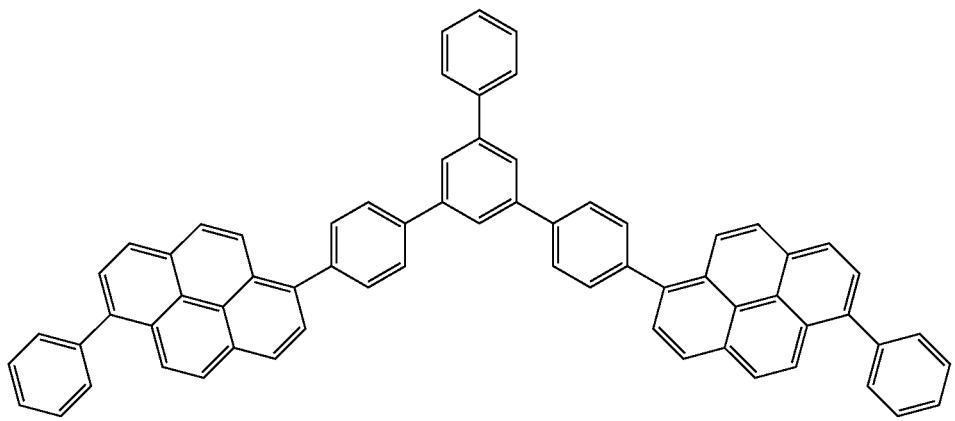
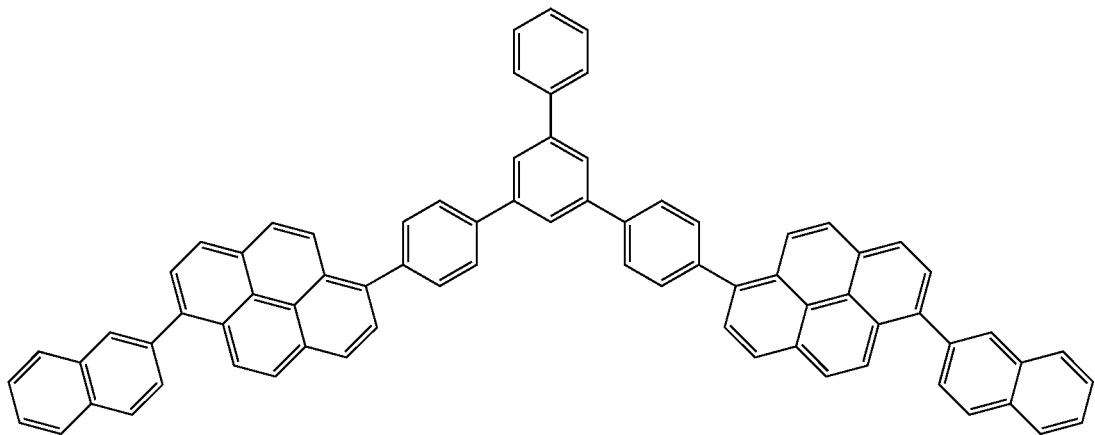

-continued
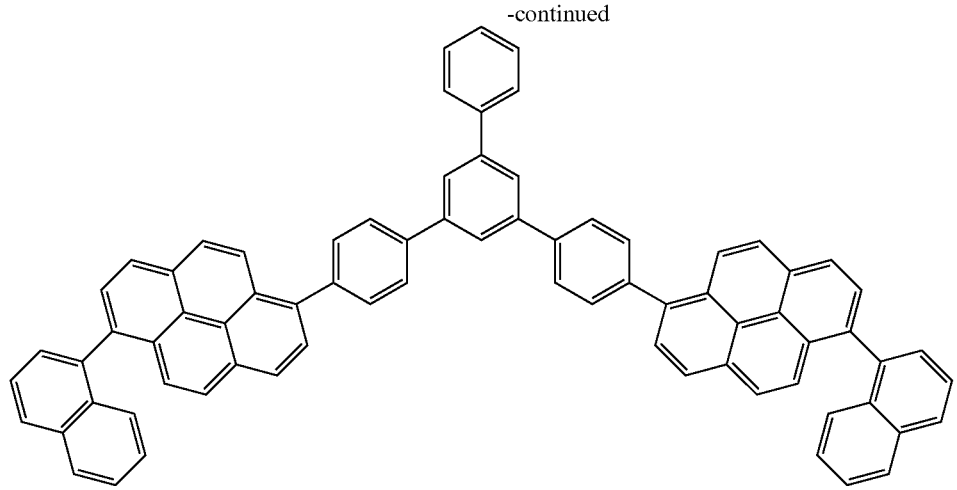
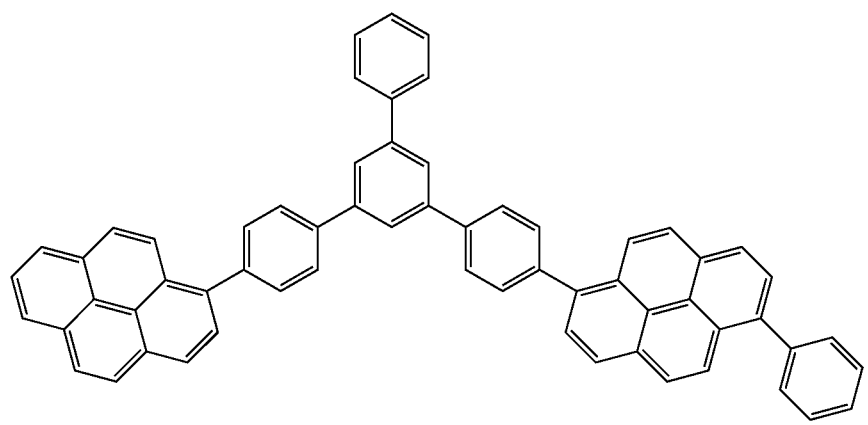
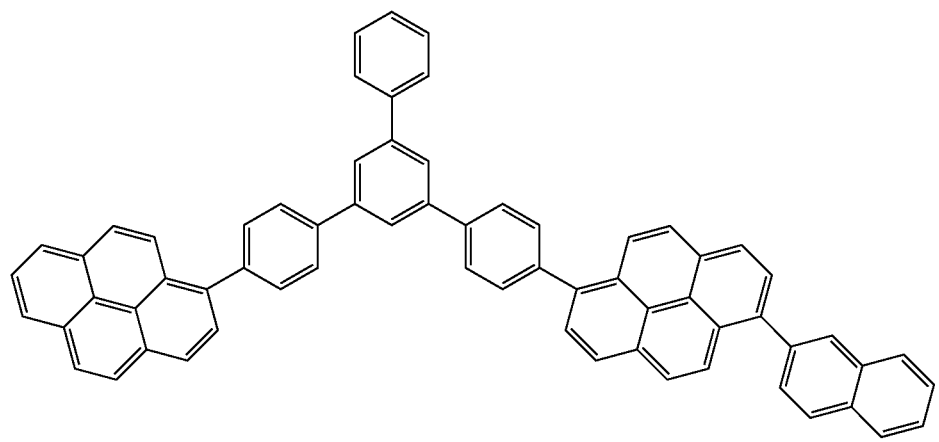

-continued
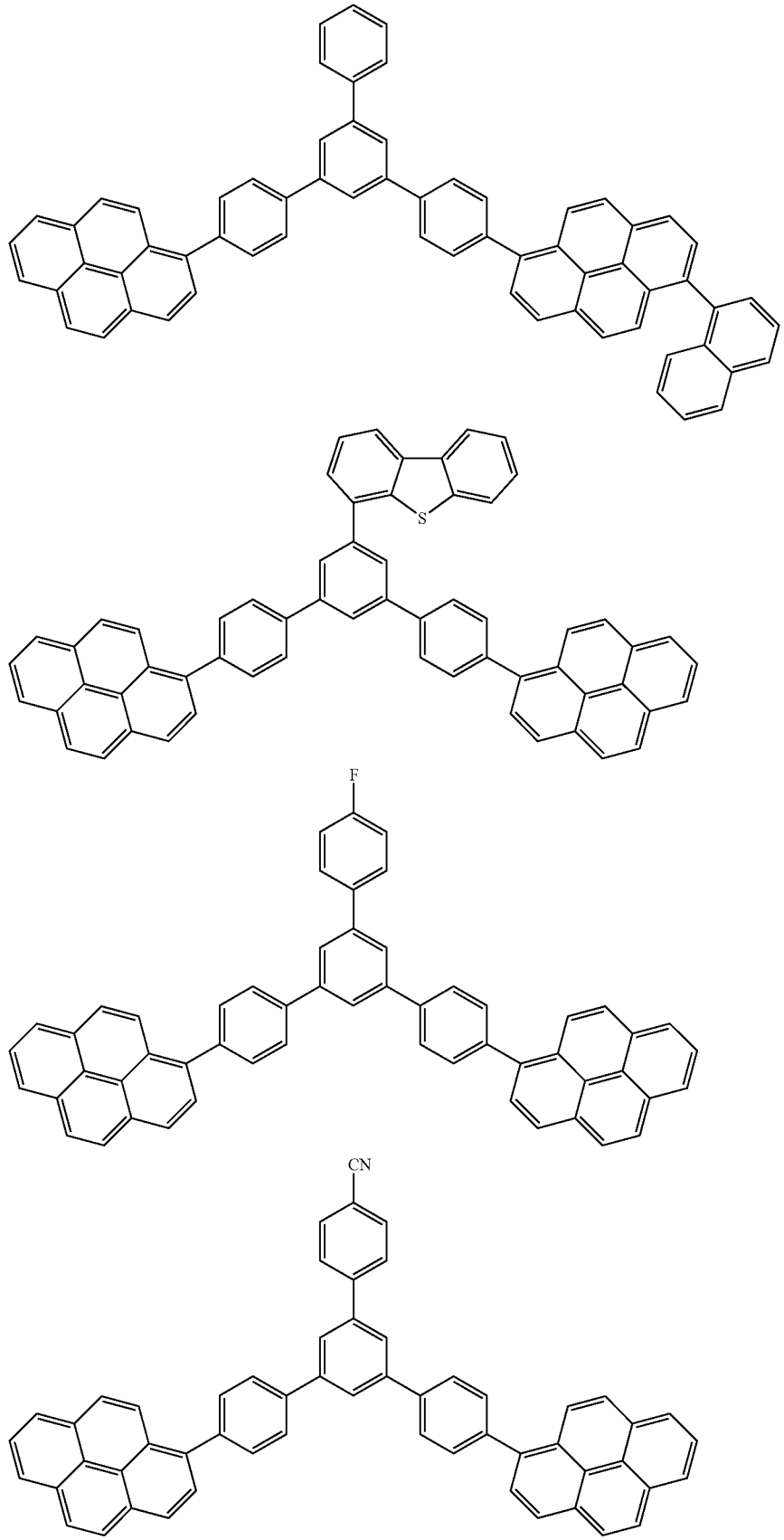

-continued
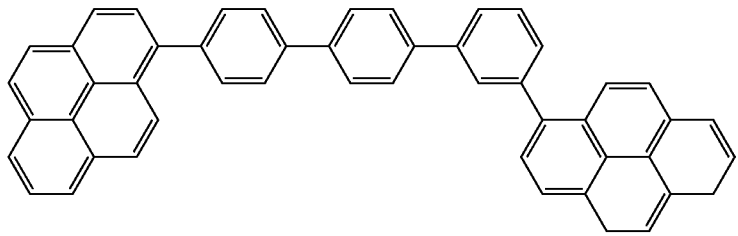
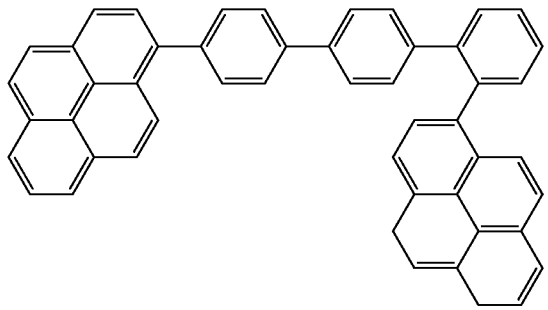
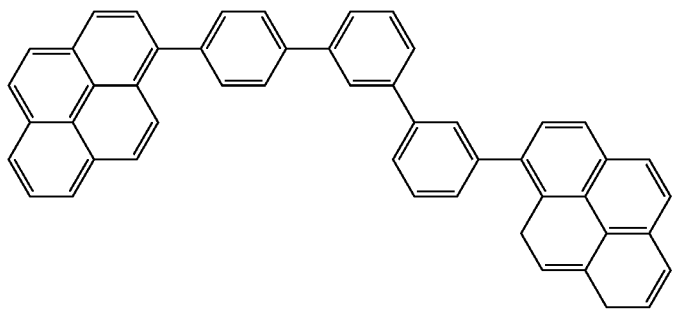
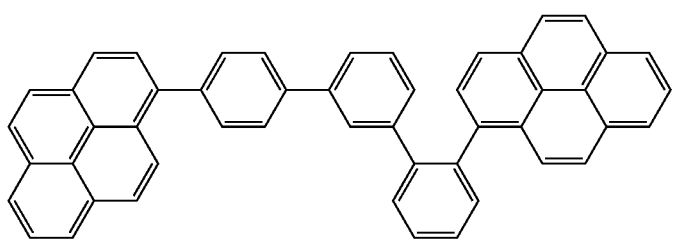
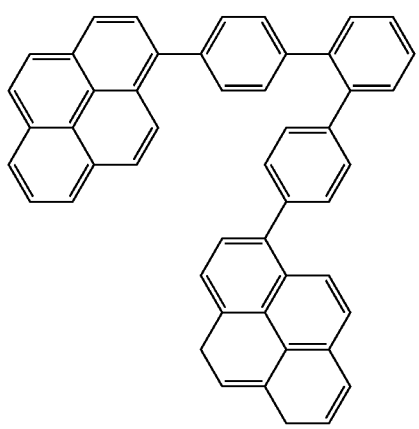

-continued
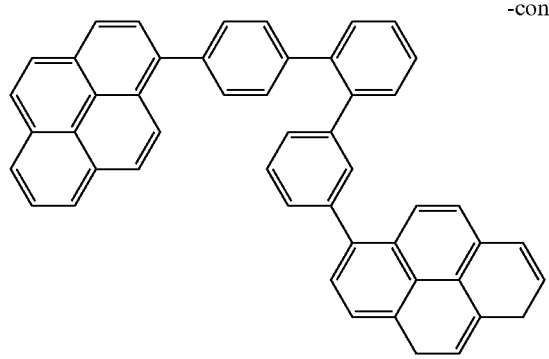
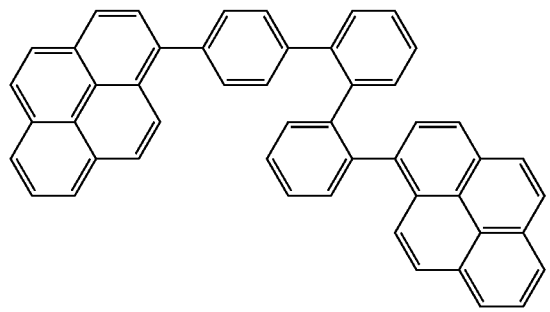
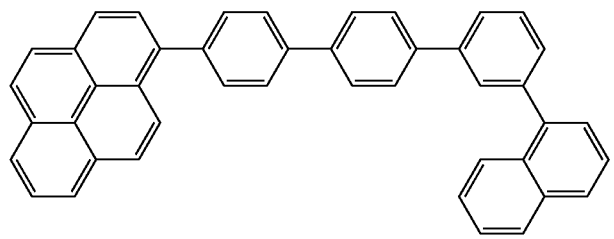
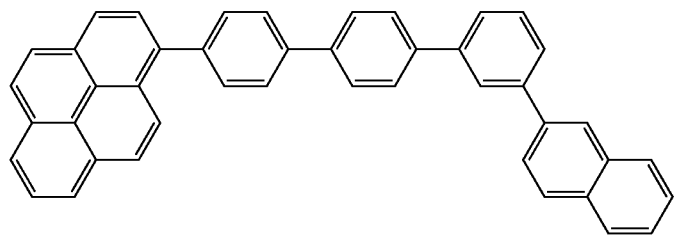
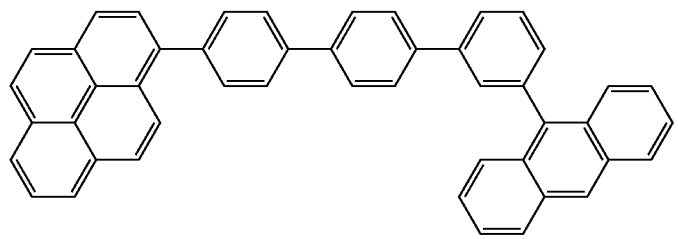
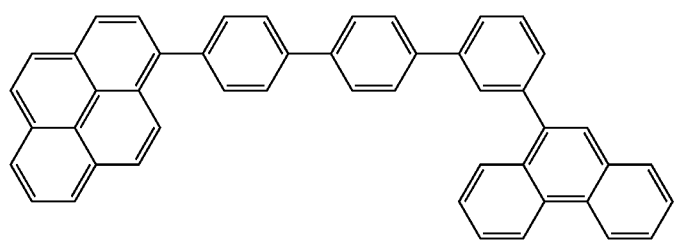

-continued
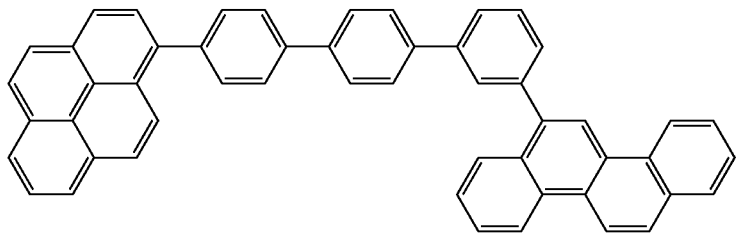
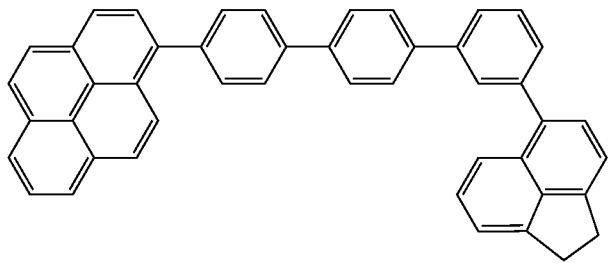
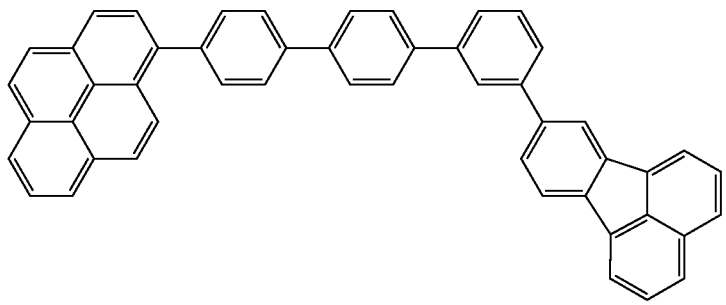
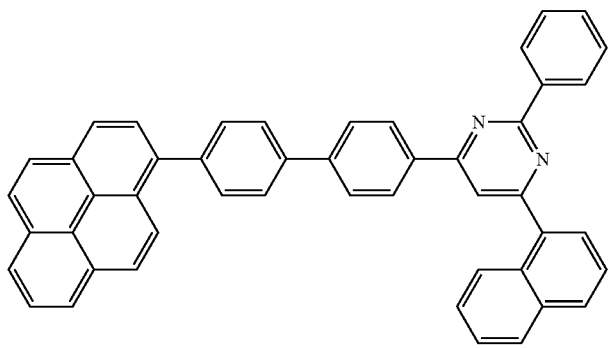
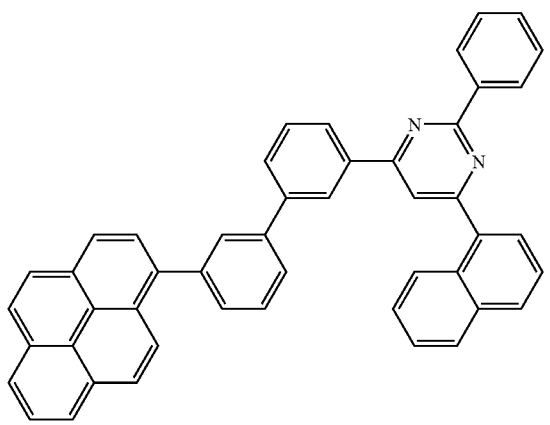

-continued
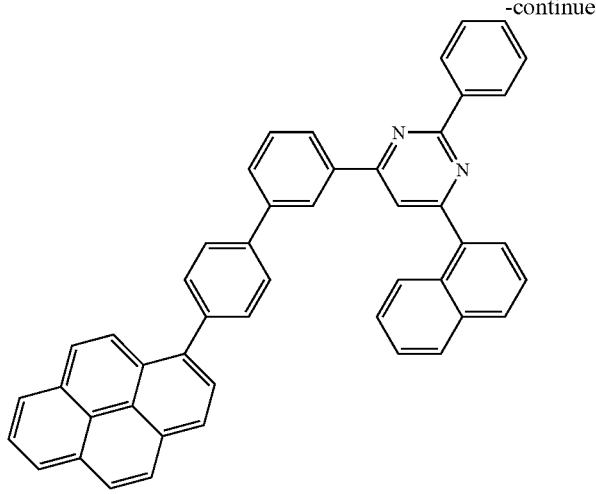
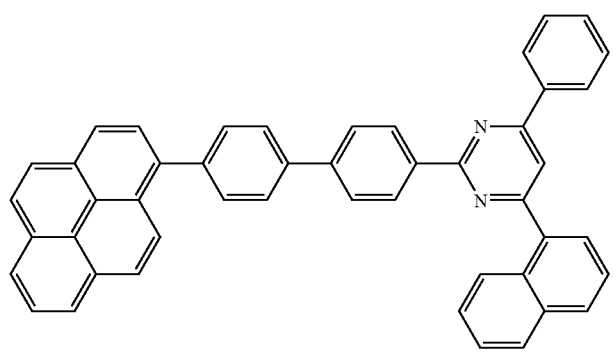
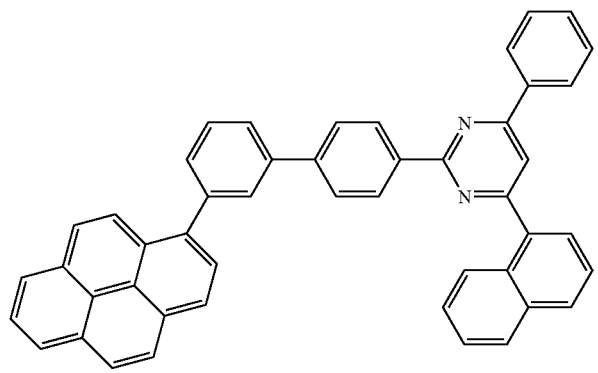
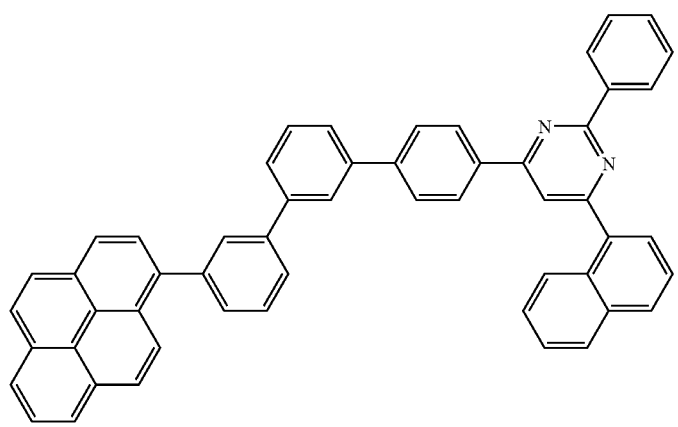

-continued
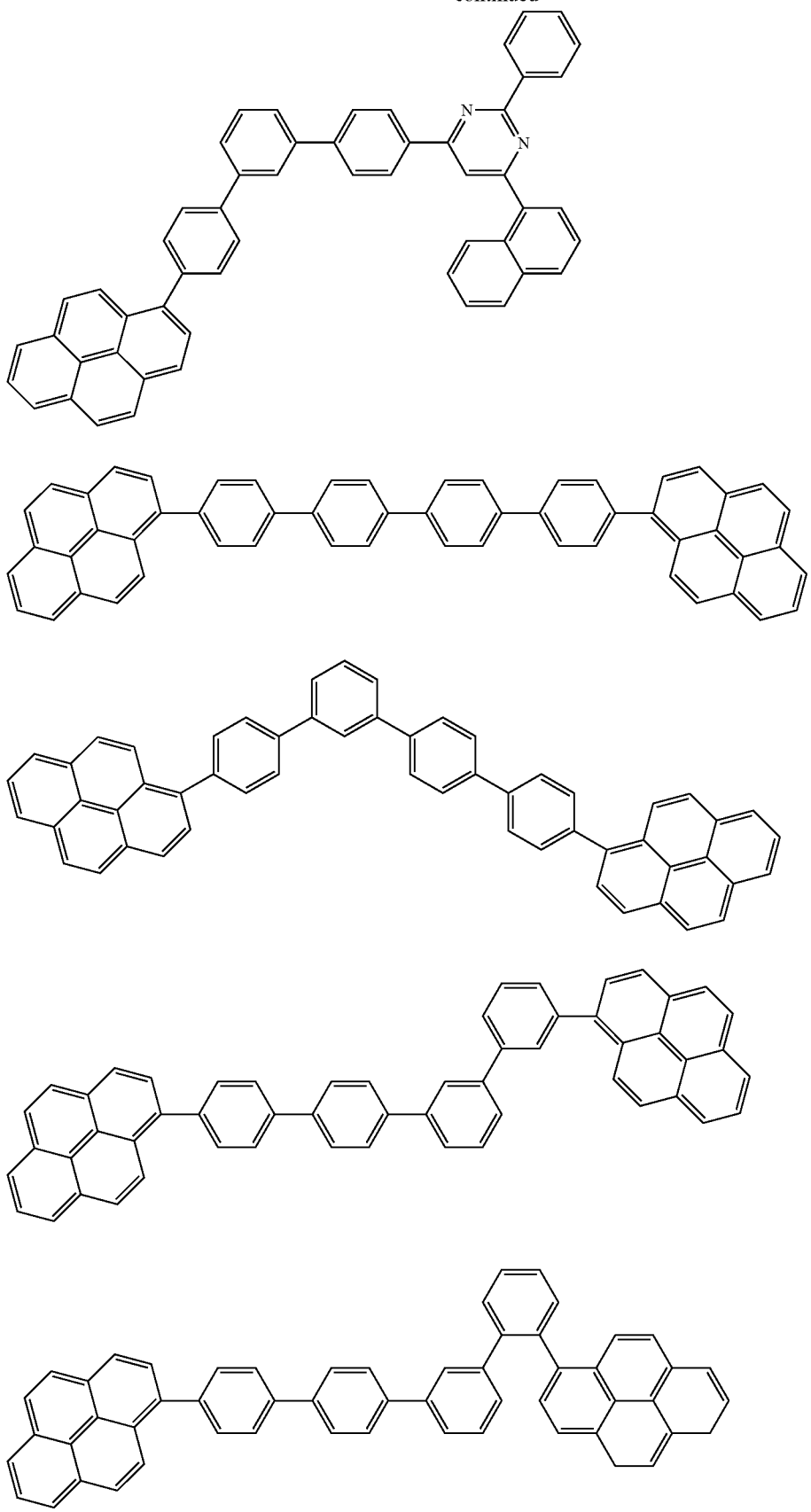

-continued
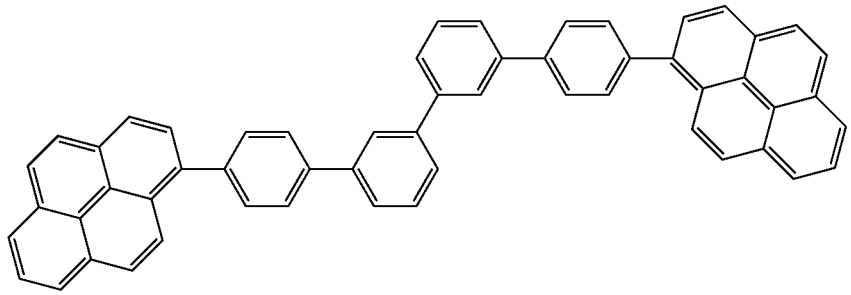
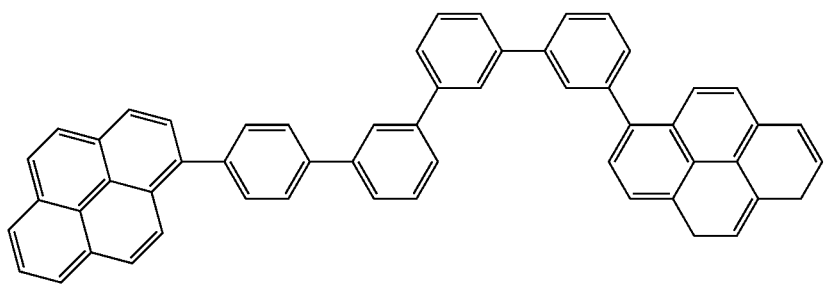
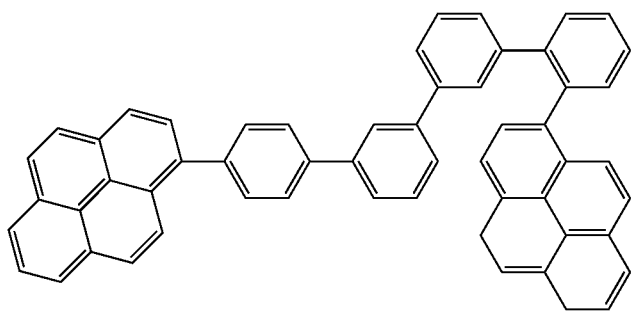
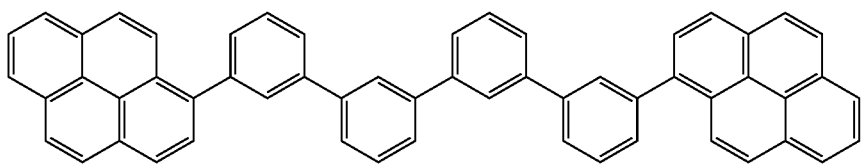
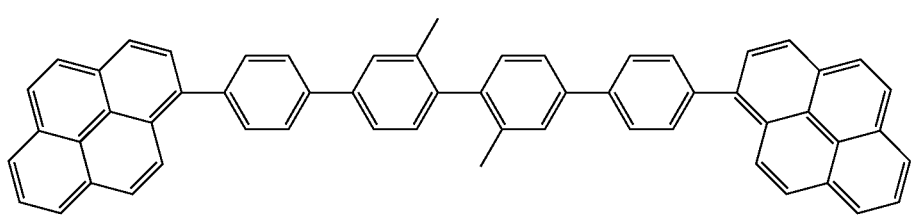
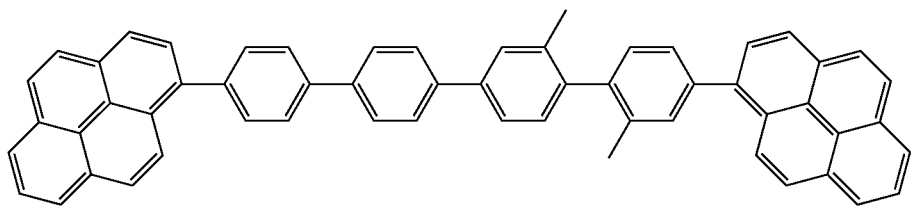

-continued
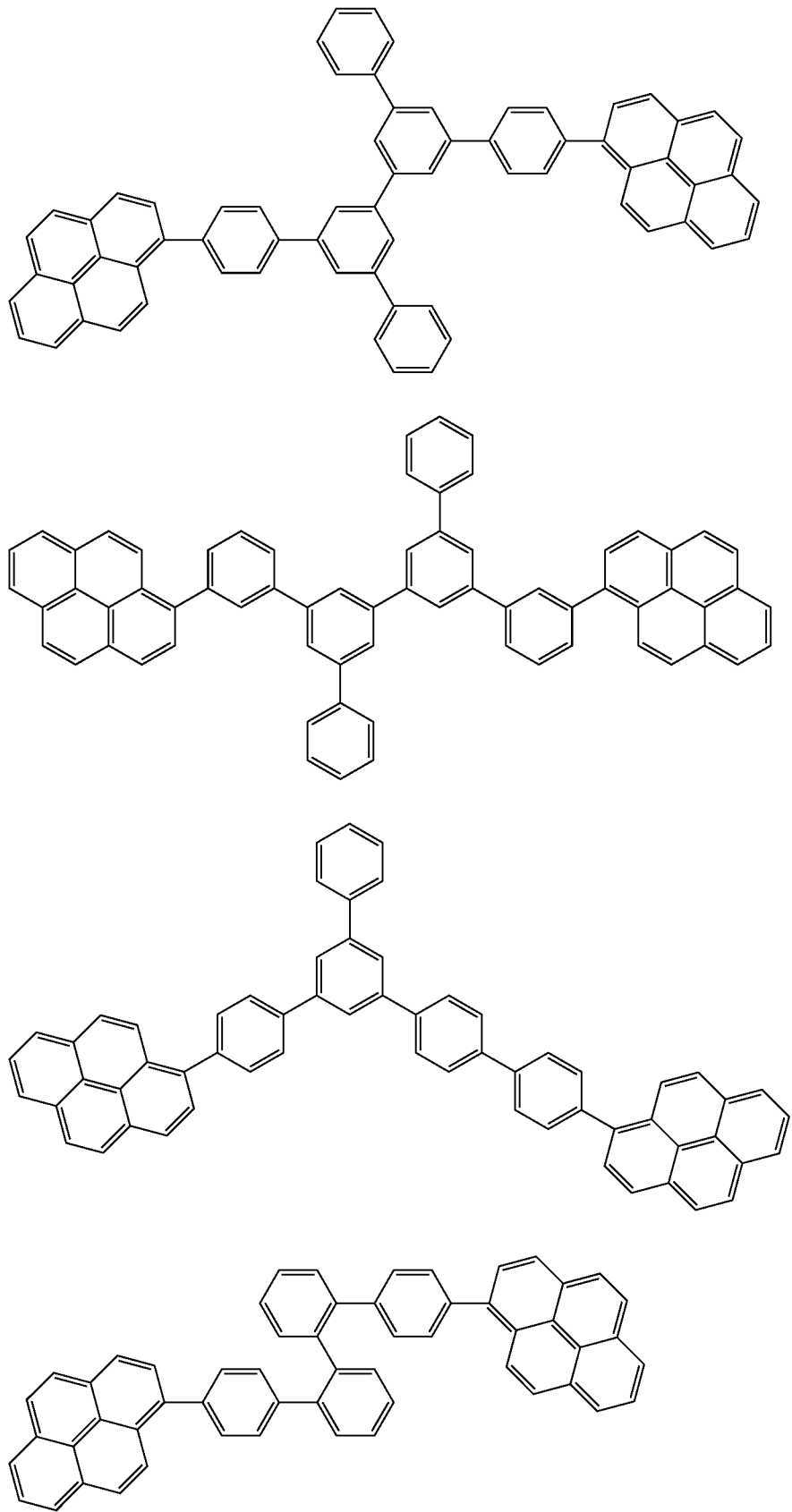

-continued
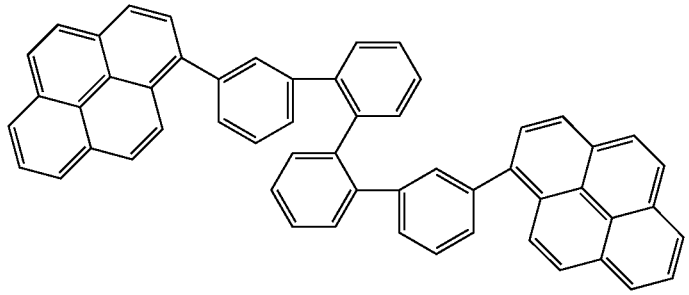

-continued
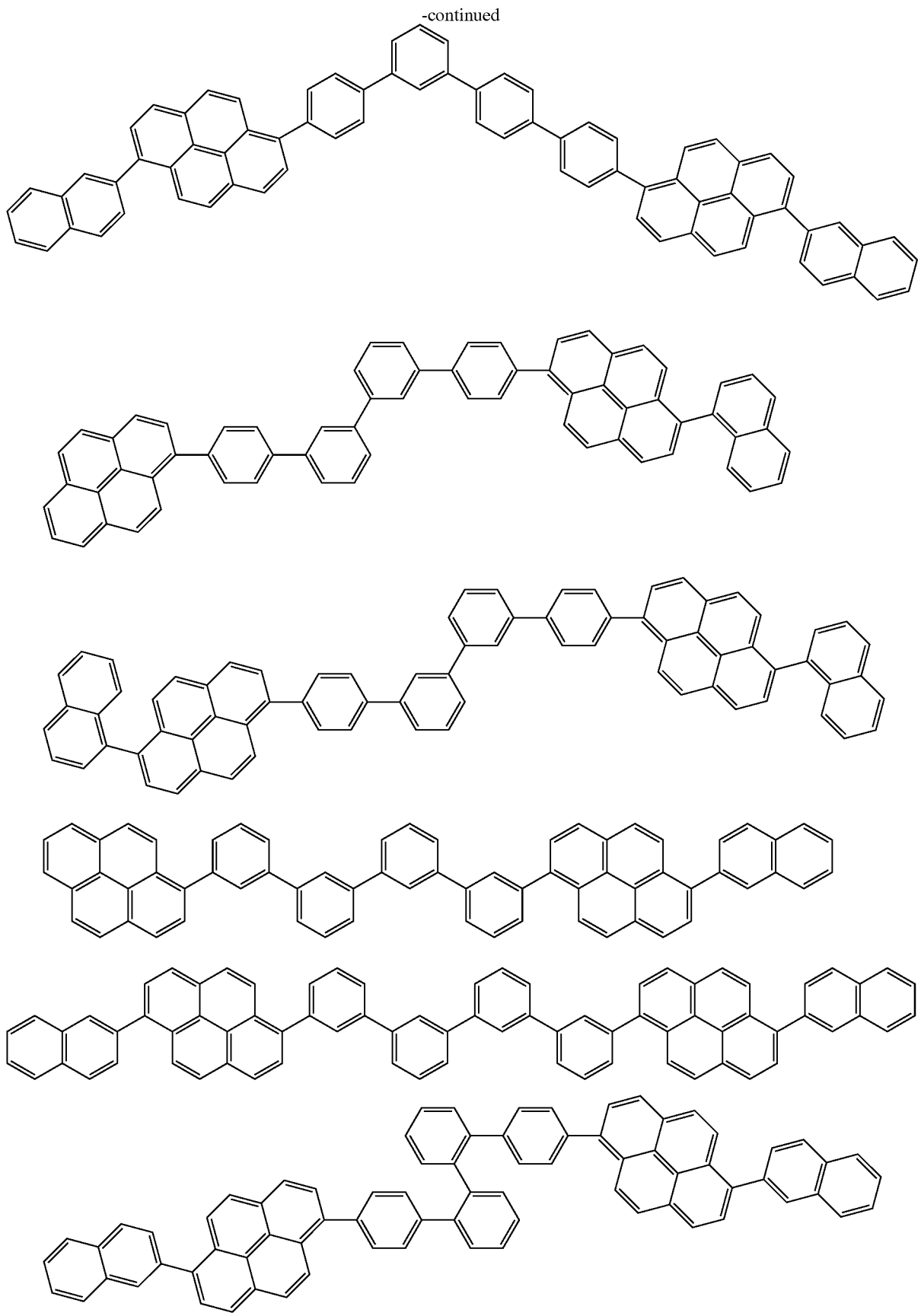

-continued
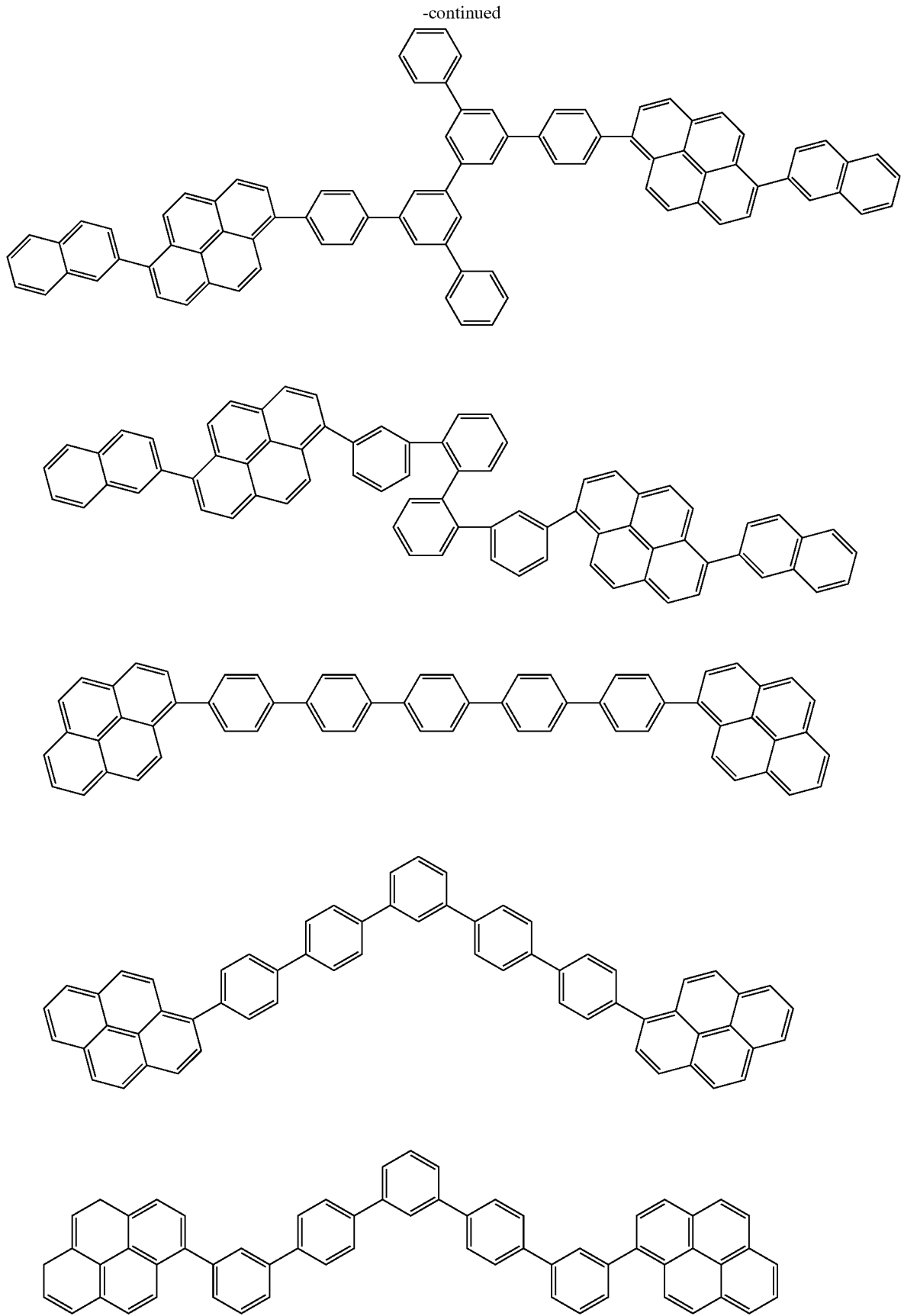

-continued
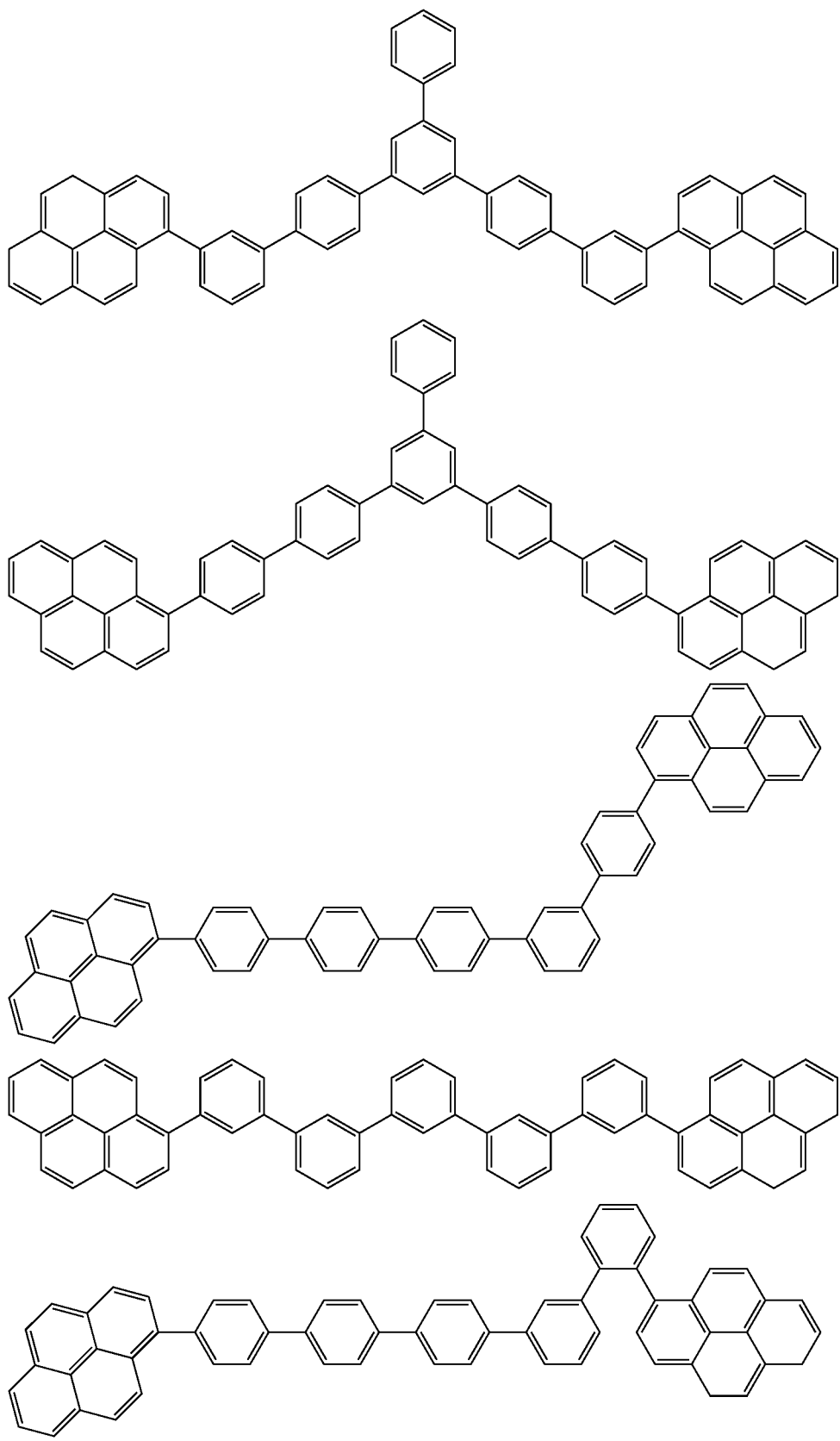

-continued
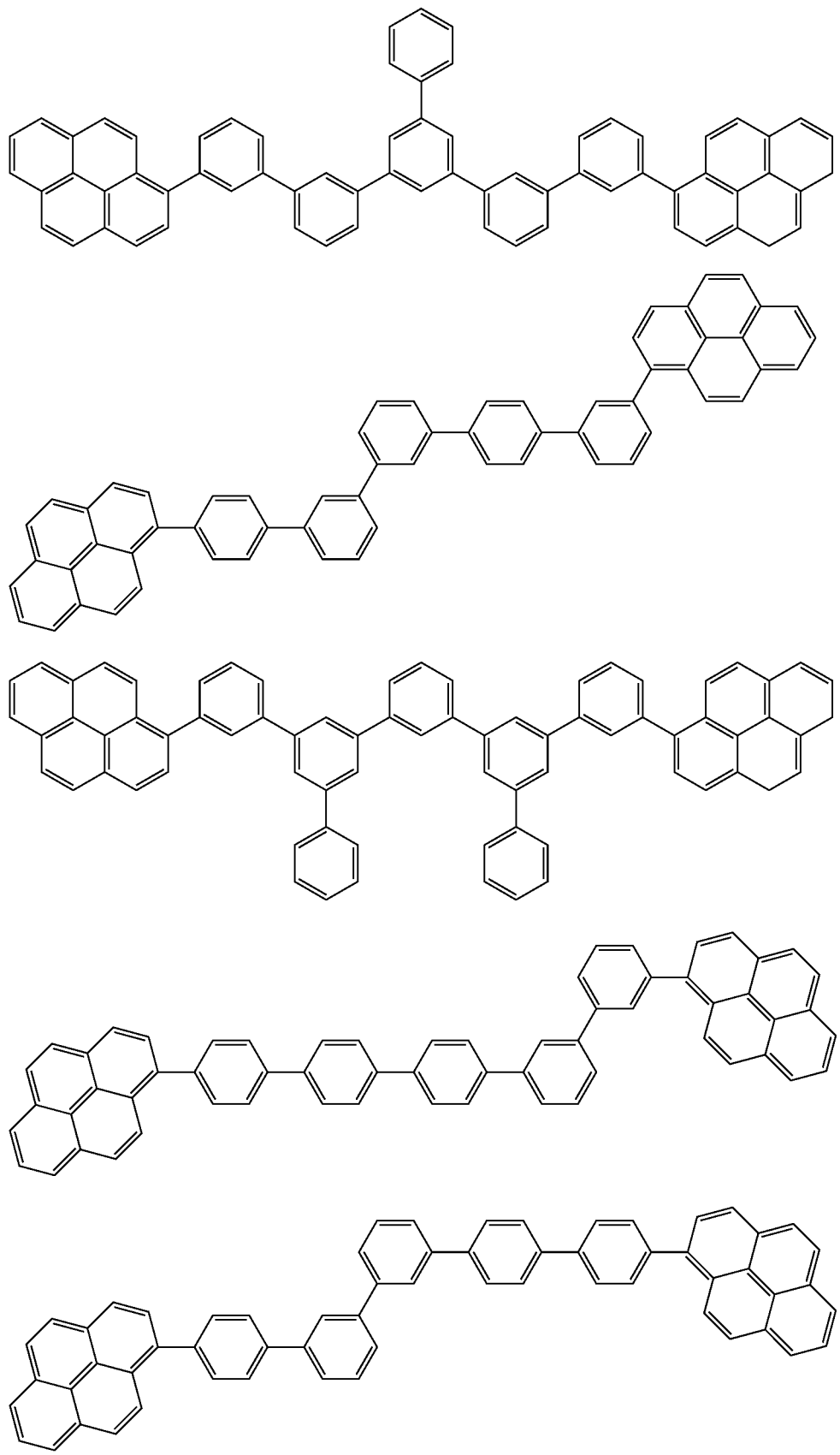

-continued
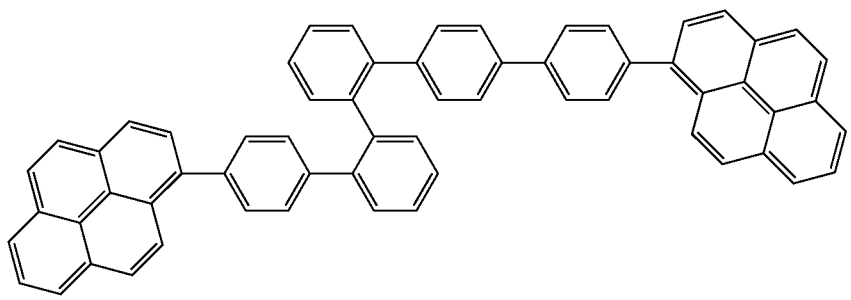
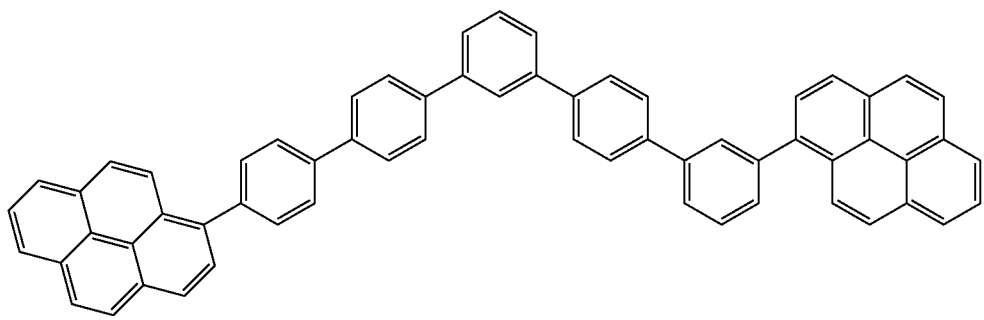
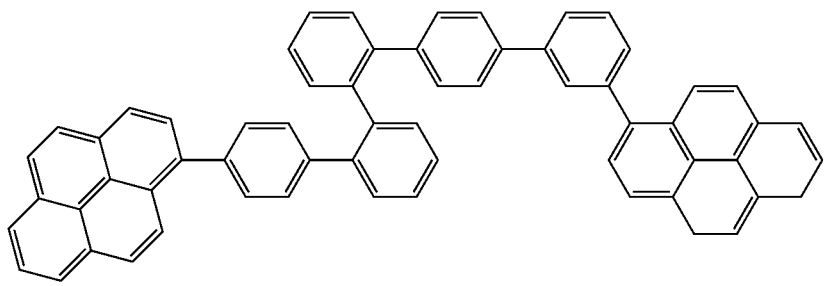
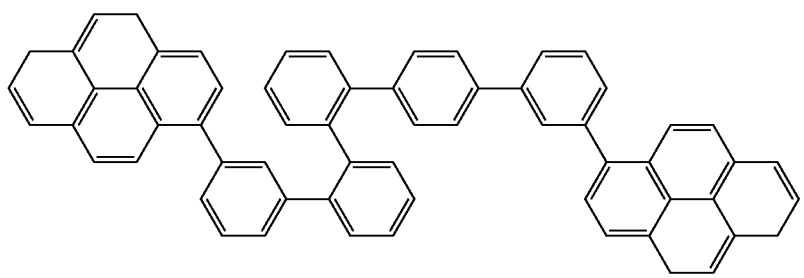
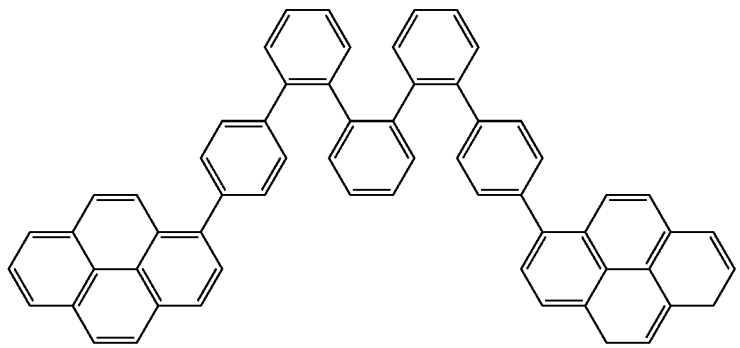

-continued
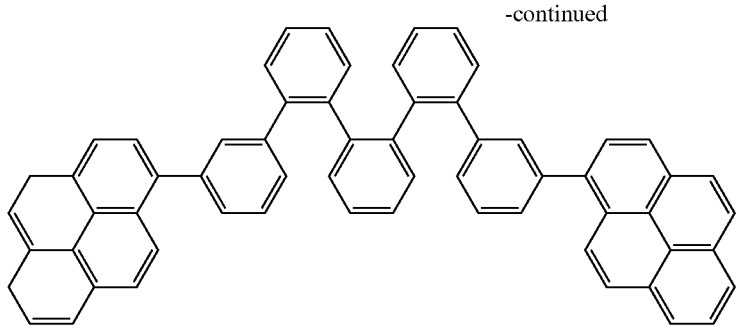
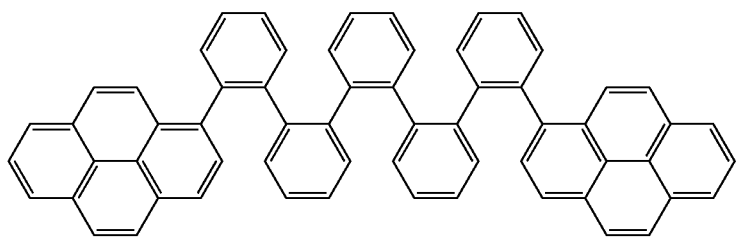
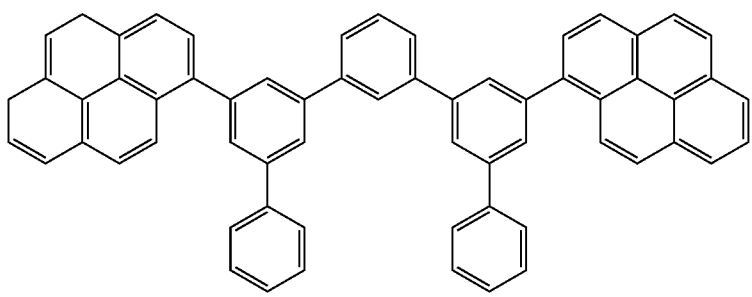
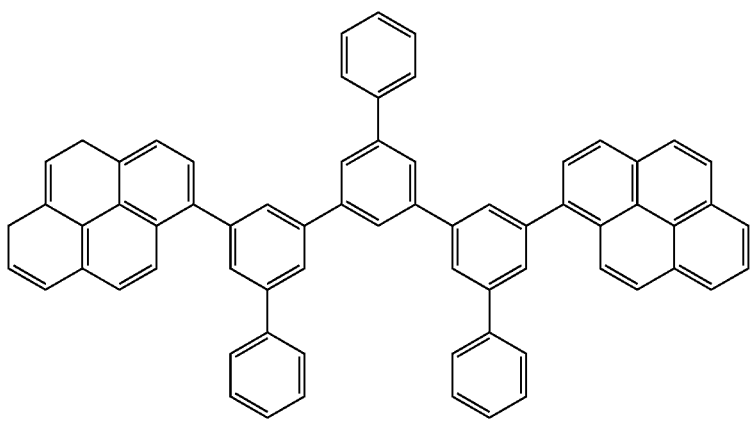
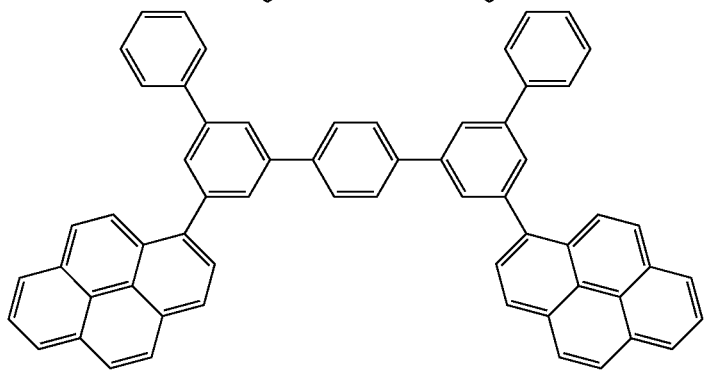

-continued

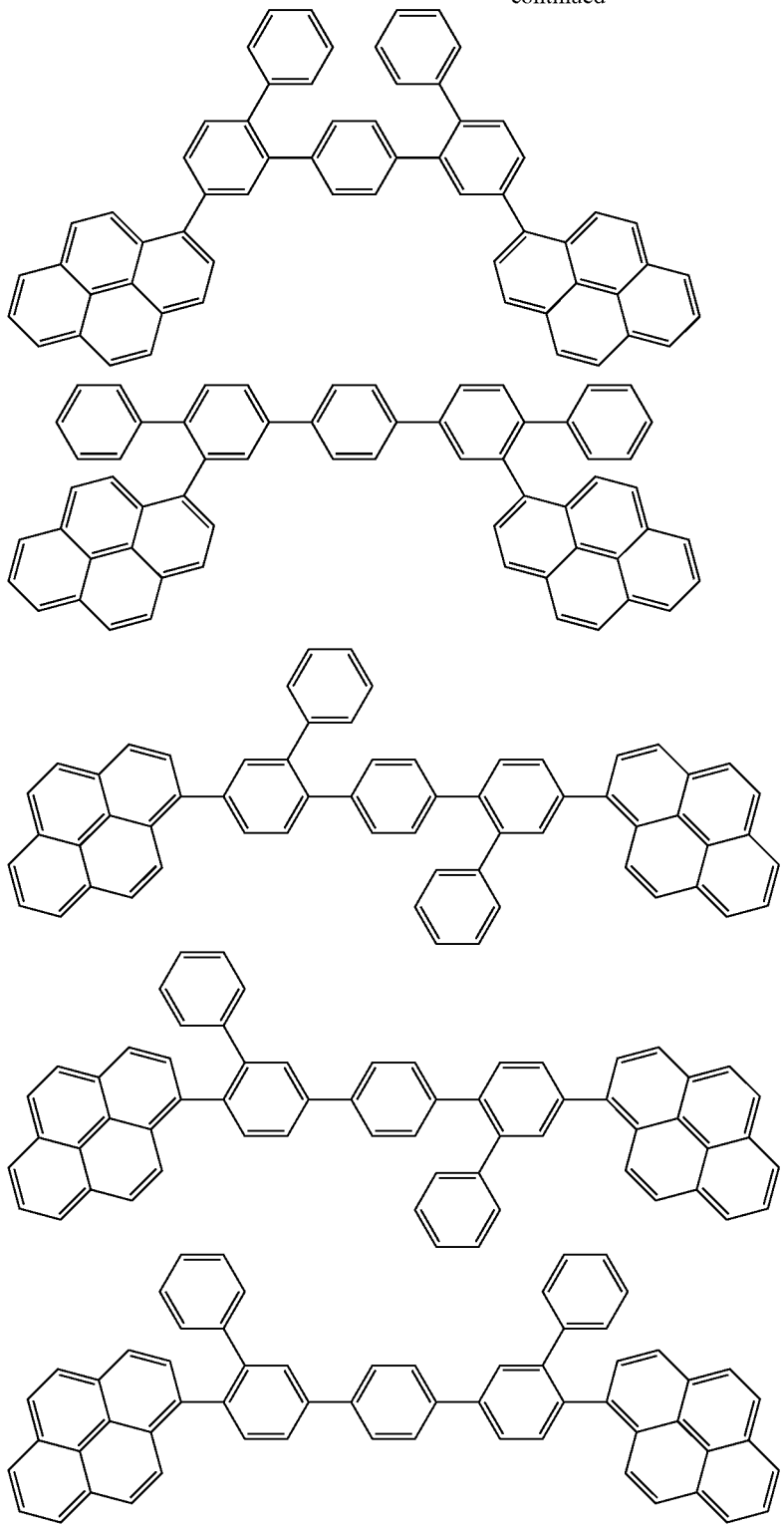

The pyrene derivative of the present invention is preferably a light emitting material for an organic EL device, and is preferably a host material for an organic EL device.

An EL device of the present invention is obtained by forming a light emitting layer or an organic compound thin film formed of multiple layers including a light emitting layer between a pair of electrodes, and at least one layer of the organic compound thin film contains the pyrene derivative represented by the general formula (1) or (2) as a light emitting material.

The light emitting layer contains the pyrene derivative represented by the general formula (1) or (2) at a content of preferably 10 to 100%, or more preferably 50 to 99%.

In the organic EL device of the present invention, the light emitting layer preferably further contains at least any one of an arylamine compound and a styrylamine compound.

Examples of the styrylamine compound preferably include compound represented by the following general formula (A).

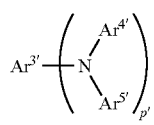

(A)

where: $Ar^{3'}$ represents a group selected from a phenyl group; a biphenyl group, a terphenyl group, a stilbene group, and distyrylaryl group; $Ar^{4'}$ and $Ar^{5'}$ each represent a hydrogen atom or an aromatic hydrocarbon group having 6 to 20 carbon atoms; each of $Ar^{3'}$, $Ar^{4'}$, and $Ar^{5'}$ may be substituted; p' represents an integer of 1 to 4; and at least one of $Ar^{4'}$ and $Ar^{5'}$ is more preferably substituted by the styryl groups.

Examples of the arylamine compound include compounds each represented by the following general formula (B).

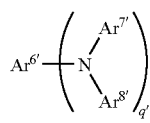

(B)

where $Ar^{6'}$ to $Ar^{8'}$ each represent a substituted or unsubstituted aryl group having 5 to 40 ring carbon atoms, and q' represents an integer of 1 to 4.

Here, preferable examples of the aryl group having 5 to 40 ring carbon atoms include a phenyl group, a naphthyl group, an anthranyl group, a phenanthryl group, a pyrenyl group, a coronyl group, a biphenyl group, a terphenyl group, a pyrrolyl group, a furanyl group, a thiophenyl group, a benzothiophenyl group, an oxadiazolyl group, a diphenylanthranyl group, an indolyl group, a carbazolyl group, a pyridyl group, a benzoquinolyl group, a fluoranthenyl group, an acenaphthofluoranthenyl group, a stilbene group, a perylenyl group, a chrysenyl group, a pycenyl group, a triphenylenyl group, a rubicenyl group, a benzoanthracenyl group, a phenylanthracenyl group, a bisanthracenyl group, and aryl groups represented by the following general formulae (C) and (D), where a napthyl group, an anthranyl group, a chrysenyl group, a pyrenyl group, and an aryl group represented by the following general formula (D) are preferable.

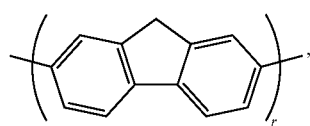

(C)

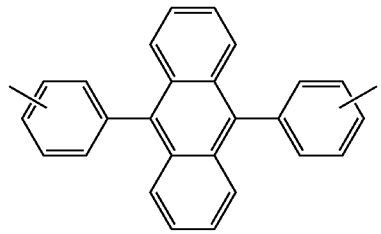

(D)

In the general formula (C), r represents an integer of 1 to 3.

It should be noted that a preferable substituent for the aryl group is, for example, an alkyl group having 1 to 6 carbon atoms (such as an ethyl group, a methyl group, an isopropyl group, an n-propyl group, an s-butyl group, a t-butyl group, a pentyl group, a hexyl group, a cyclopentyl group, or a cyclohexyl group), an alkoxy group having 1 to 6 carbon atoms (such as an ethoxy group, a methoxy group, an isopropoxy group, an n-propoxy group, an s-butoxy group, a t-butoxy group, a pentoxy group, a hexyloxy group, a cyclopentoxy group, or a cyclohexyloxy group), an aryl group having 5 to 40 ring carbon atoms, an amino group substituted by an aryl group having 5 to 40 ring carbon atoms, an ester group having an aryl group having 5 to 40 ring carbon atoms, an ester group having an alkyl group having 1 to 6 carbon atoms, a cyano group, a nitro group, or a halogen atom.

The light emitting layer may contain the pyrene derivative represented by the general formula (1) or (2) and a fluorescent or phosphorescent dopant as a mixture.

The fluorescent dopant is preferably a compound selected from, for example, an amine-based compound, a chelate complex such as a tris(8-quinolinolato)aluminum complex, a coumarin derivative, a tetraphenylbutadiene derivative, a bis-styrylarylene derivative, and an oxadiazole derivative in accordance with a requested luminescent color.

The phosphorescent dopant is preferably a metal complex containing at least one metal selected from the group consisting of Ir, Ru, Pd, Pt, Os, and Re. The ligand of the metal complex preferably includes at least one skeleton selected from the group consisting of phenylpyridine skeleton, bipyridyl skeleton, and phenanthroline skeleton. Specific examples of the metal complex include tris(2-phenylpyridine)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, octaethyl platinum porphyrin, octaphenyl platinum porphyrin, octaethyl palladium porphyrin, and octaphenyl palladium porphyrin. However, the metal complex is not limited thereto, and the appropriate complex is preferably selected in terms of a desired luminescent color, a device performance, and a relationship with a host compound.

Hereinafter, the device constitution of an organic EL device of the present invention will be described.

The organic EL device of the present invention is a device obtained by forming an organic thin film layer formed of one or more layers between an anode and a cathode. In the case where the organic thin film layer is formed of one layer, a light emitting layer is provided between the anode and the cathode. The light emitting layer contains a light emitting material, and may contain a hole injecting material or an electron injecting material in addition to the light emitting material for transporting, to the light emitting material, a hole injected from the anode or an electron injected from the cathode. The light emitting material preferably forms a uniform thin film bringing together extremely high fluorescent quantum efficiency, a high hole transporting ability, and a high electron transporting ability.

In the device constitution, the multiple layer type organic EL device is a laminate having, for example, an (anode/hole injecting layer/light emitting layer/cathode), (anode/light emitting layer/electron injecting layer/cathode), (anode/hole injecting layer/light emitting layer/electron injecting layer/cathode), or (anode/hole injecting layer/hole transporting layer/light emitting layer/electron injecting layer/cathode) multiple layer constitution.

In addition to the pyrene derivative shown in the general formula (1) or (2) of the present invention, an additional known light emitting material, doping material, hole injecting material, or electron-injecting material can be used as required in the light emitting layer.

As the doping material, in addition to conventional fluorescent light emitting materials, any one of a heavy metal complex such as phosphorescent emission iridium may be used. When the organic EL device is formed with multiple layers, a reduction in luminance or lifetime due to quenching can be prevented. If needed, a light emitting material, another doping material, a hole injecting material, and an electron-injecting material can be used in combination. In addition, the other doping material can provide improvements in emission luminance and luminous efficiency, and red or white light emission.

In addition, each of the hole injecting layer, the light emitting layer, and the electron-injecting layer may be formed of a layer constitution having two or more layers. At that time, in the case of the hole injecting layer, a layer for injecting a hole from the electrode is referred to as a hole injecting layer, and a layer for receiving the hole from the hole injecting layer and transporting the hole to the light emitting layer is referred to as a hole transporting layer. In the same manner, in the case of the electron-injecting layer, a layer for injecting an electron from the electrode is referred to as an electron-injecting layer, and a layer for receiving the electron from the electron-injecting layer and transporting the electron to the light emitting layer is referred to as an electron-transporting layer. Each of those layers is selected and used depending on factors such as the energy level of a material, heat resistance, and adhesiveness between the layer and an organic layer or a metal electrode.

Examples of a host material which can be used in the organic layer together with the pyrene derivative of the general formula (1) or (2) include, but are not limited to, anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyrane, thiopyrane, polymethine, merocyanine, imidazole-chelated oxynoid compounds, quinacridone, rubrene, a stilbene-based derivative, and fluorescent dyes.

A compound having an ability of transporting a hole, having hole injecting effect from an anode and excellent hole injecting effect to a light emitting layer or a light emitting material, an ability of preventing the migration of an exciton generated in the light emitting layer to an electron injecting layer or an electron injecting material, and having excellent thin film-formability is preferable as a hole injecting material. Specific examples of the compound include, but are not limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Of the hole injecting materials that can be used in the organic EL device of the present invention, additional effective hole injecting materials are an aromatic tertiary amine derivative or a phthalocyanine derivative.

Specific examples of the aromatic tertiary amine derivative include, but are not limited to, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, or an oligomer or a polymer having those aromatic tertiary amine skeletons.

Specific examples of the phthalocyanine (Pc) derivative include, but are not limited to, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPC$, (HO)AlPc, (HO)GaPc, VOPc, TiOPc, MoOPc, and GaPc-O-GaPc, and naphthalocyanine derivatives.

A compound having an ability of transporting electrons, having electron injecting effect from a cathode and excellent electron injecting effect to a light emitting layer or a light emitting material, an ability of preventing the migration of an exciton generated in the light emitting layer to the hole injecting layer, and having excellent thin film-formability is preferable as an electron injecting material. Specific examples of the compound include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the compound is not limited thereto.

In addition, an electron-accepting substance can be added to the hole injecting material or an electron-donating substance can be added to the electron injecting material to thereby improve properties of charge injection.

An additionally effective electron injecting material in the organic EL device of the present invention is a metal complex compound or a nitrogen-containing five-membered ring derivative.

Specific examples of the metal complex compound include, but not limited to, 8-hydroxyquinoline-based metal complexes such as tris(8-quinolinol)aluminum, bis(8-quinolinol)magnesium, bis[benzo(f)-8-quinolinol]zinc, bis(2-methyl-8-quinolinolato)aluminum oxide, tris(8-quinolinol)indium, tris(5-methyl-8-quinolinol)aluminum, 8-quinolinol lithium, tris(5-chloro-8-quinolinol)gallium, bis(5-chloro-8-quinolinol)calcium, and poly(zinc(II)-bis(8-hydroxy-5-quinolinonyl)methane), and dilithium epindolidione.

Further, preferred nitrogen-containing five-membered derivatives include, an oxazole derivative, a thiazole derivative, an oxadiazole derivative, a thiadiazole derivative, and a triazole derivative. Specific examples of the derivative include, but are not limited to, 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-t-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4- bis[2-(5-phenyloxadiazolyl)-4-t-butylbenzene], 2-(4'-tertbutylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-t-butylphenyl)-5-(4"-biphenyl)-1,3,4-triazole, 2,5-bis(1-naphthyl)-1,3,4-triazole, and 1,4-bis[2-(5-phenyltriazolyl)]benzene.

In the organic EL device of the present invention, in addition to the pyrene derivative of the general formula (1) or (2), at least one kind of a light emitting material, a doping material, a hole injecting material, and an electron injecting material may be incorporated into the same organic layer. In addition, the surface of the organic EL device obtained according to the present invention can be provided with a protective layer, or the entire device can be protected with silicone oil, a resin, or the like with a view to improving the stability of the device against temperature, humidity, an atmosphere, or the like.

A conductive material having a work function larger than 4 eV is suitably used in the anode of the organic EL device. Examples of an available conductive material include: carbon, aluminum, vanadium, iron, cobalt, nickel, tungsten, silver, gold, platinum, and palladium, and alloys thereof; metal oxides such as tin oxide and indium oxide to be used in an ITO substrate and an NESA substrate; and organic conductive resins such as polythiophene and polypyrrole.

In the organic EL device of the present invention, a conductive substance having a work function smaller than 4 eV is suitably used in the cathode of the device. Examples of an available conductive substance include, but are not limited to, magnesium, calcium, tin, lead, titanium, yttrium, lithium, ruthenium, manganese, and aluminum, and alloys thereof. Representative examples of the alloys include, but are not limited to, a magnesium/silver alloy, a magnesium/indium alloy, and a lithium/aluminum alloy. A composition ratio of an alloy is controlled depending on, for example, the temperature of a deposition source, an atmosphere, and the degree of vacuum, and is selected to be an appropriate ratio.

Each of the anode and the cathode may be formed in a layer constitution having two or more layers if needed. It is desirable that at least one surface of the organic EL device be sufficiently transparent in the luminous wavelength region of the device so that the device can efficiently emit light.

The substrate to be used in the organic EL device of the present invention is also desirably transparent. A transparent electrode is formed by any one of the above conductive materials, and is set by a method such as deposition or sputtering in such a manner that desired translucency is secured. The light transmittance of an electrode on a light emitting surface is desirably 10% or more. The substrate is not limited as long as it has mechanical strength, thermal strength, and transparency. Examples of the substrate include a glass substrate and a transparent resin film. Examples of the transparent resin film include polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyetherimide, polyimide, and polypropylene.

Any one of: dry film forming methods such as vacuum deposition, sputtering, plasma, and ion plating; and wet film forming methods such as spin coating, dipping, and flow coating is applicable to the formation of each layer of the organic EL device according to the present invention. The thickness of each layer is not particularly limited, but must be set to an appropriate thickness. An excessively large thickness requires an increased applied voltage for obtaining certain optical output, resulting in poor efficiency. An excessively small thickness causes a pin hole or the like, so sufficient emission luminance cannot be obtained even when an electric field is applied. In general, the thickness is in the range of preferably from 5 nm to 10 μm, or more preferably from 10 nm to 0.2 μm. In the case of a wet film forming method, a material of which each layer is formed is dissolved or dispersed into an appropriate solvent such as ethanol, chloroform, tetrahydrofuran, or dioxane, to thereby form a thin film. At that time, any one of the above solvents may be used. In addition, an appropriate resin or additive may be used in each of the organic thin film layers for, for example, improving film formability or preventing a pin hole in the layer. Examples of an applicable resin include: insulating resins such as polystyrene, polycarbonate, polyallylate, polyester, polyamide, polyurethane, polysulfone, polymethyl methacrylate, polymethyl acrylate, and cellulose, and copolymers thereof; photoconductive resins such as poly-N-vinylcarbazole and polysilane; and conductive resins such as polythiophene and polypyrrole. Examples of the additive include an antioxidant, a UV absorber, and a plasticizer.

As described above, the use of the pyrene derivative represented by the general formula (1) or (2) of the present invention as a light emitting material in the organic layer of an organic EL device can provide the organic EL device with high luminous efficiency, excellent heat resistance, a long lifetime, and a good color purity.

The organic EL device of the present invention can find use in applications including: a flat luminous body such as a flat panel display of a wall hanging television; a light source for the backlight, meters, or the like of a copying machine, a printer, or a liquid crystal display; a display panel; and a signal lamp.

EXAMPLES

Hereinafter, examples of the present invention will be described more specifically. However, the present invention is not limited to those examples. It should be noted that an organic EL device obtained in each example was evaluated in the following manner.

(1) Initial performance: A predetermined voltage was applied to the organic EL device, and a current value at the time of the application was measured. An emission luminance value and CIE1931 chromaticity coordinates were measured by a luminance meter (Spectroradiometer CS-1000, manufactured by Konica Minolta Sensing, Inc.) simultaneously with the measurement of the current value to evaluate the initial performance of the device.

(2) Lifetime: The organic EL device was driven at a constant current at initial luminance of 1,000 cd/m$^2$. The device was evaluated for its lifetime on the basis of the half life of the luminance and a change in chromaticity.

Example 1

Synthesis of Compound (H-1)

Compound (H-1) was synthesized according to the following reaction formula.

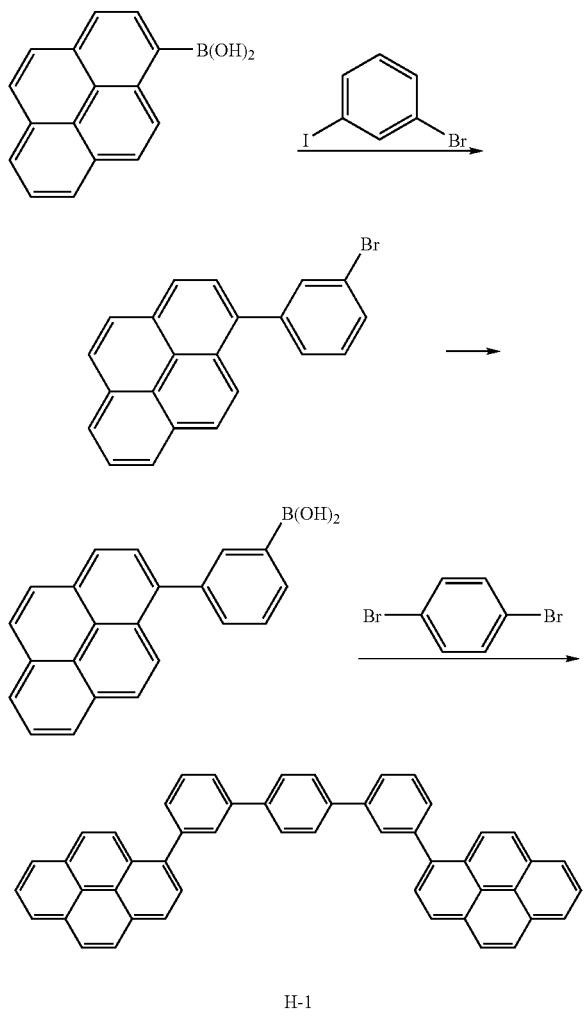

H-1

4.92 g (20 mmol) of pyrene-1-boronic acid, 5.94 g (21 mmol) of 3-bromoiodobenzene, and 0.46 g (0.4 mmol, 2 mol %) of tetrakis(triphenylphosphine)palladium(0) were loaded into a 300-ml three-necked flask, and air in the container was replaced with argon. Further, 10 ml of toluene and 30 ml (3 eq) of a 2M aqueous solution of sodium carbonate were added to the mixture, and the whole was refluxed under heat in an oil bath at 100° C. for 8 hours. After one night, the resultant was extracted with toluene/ion-exchanged water and purified by column chromatography, whereby 5.61 g of 3-pyrenylbromobenzene were obtained (79% yield).

Next, 5.36 g (15.0 mmol) of 3-pyrenylbromobenzene obtained in the foregoing were dissolved in a mixed solvent of 50 ml of toluene and 50 ml of diethyl ether. Under an argon atmosphere at −70° C., 11.3 ml (18.0 mmol) of a (1.6M) solution of n-butyllithium in hexane were added to the solution, and the mixture was stirred for 1 hour while its temperature was changed from −70° C. to 0° C. Next, the reaction solution was cooled to −70° C., 10.3 ml (45 mmol) of triisopropyl borate were dropped to the reaction solution, and the mixture was stirred at −70° C. for 1 hour. After that, the temperature of the reaction solution was increased to room temperature, and the reaction solution was stirred for 6 hours. Further, 100 ml of 5% hydrochloric acid were dropped to the reaction solution, and the mixture was stirred at room temperature for 45 minutes. After the reaction solution had been separated into two layers, the organic layer was washed with a saturated salt solution and dried with anhydrous sodium sulfate. After the organic solvent had been removed by distillation under reduced pressure so as to have a volume about one fifth of its initial volume, the precipitated crystal was filtrated and sequentially washed with a mixed solvent of toluene and n-hexane and with n-hexane, whereby 3.87 g of 3-pyrenylphenylboronic acid were obtained (80% yield).

Next, 3.38 g (10.5 mmol) of 3-pyrenylphenylboronic acid, 1.18 g (5.0 mmol) of 1,3-dibromobenzene, and 0.23 g (0.2 mmol, 2 mol %) of tetrakis(triphenylphosphine)palladium(0) were loaded into a 100-ml three-necked flask, and air in the container was replaced with argon. Further, 30 ml of toluene and 7.5 ml (3 eq) of a 2M aqueous solution of sodium carbonate were added to the mixture, and the whole was refluxed under heat in an oil bath at 100° C. for 8 hours. After one night, the precipitate was separated by filtration and washed with toluene, methanol, and ion-exchanged water, whereby 2.65 g of Compound (H-1) as a target product were obtained (84% yield).

FD-MS calcd for $C_{63}H_{46}$=631, found m/z=631 ($M^+$, 100)

(Production of Organic El Device)

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes. After that, the substrate was subjected to UV ozone cleaning for 30 minutes. The glass substrate with the transparent electrode line after the washing was mounted on a substrate holder of a vacuum deposition device. First, N,N'-bis(N,N'-diphenyl-4-aminophenyl)-N,N-diphenyl-4,4'-diamino-1,1'-bipenyl film (hereinafter referred to as "TPD232 film") was formed into a film having a thickness of 60 nm on the surface on the side where the transparent electrode line was formed to cover the transparent electrode. The TPD232 film functions as a hole injecting layer. After the forming of the TPD232 film, a N,N,N',N'-tetra(4-biphenyl)-diaminobiphenylene layer (hereinafter referred to as "TBDB layer") was formed into a film having a thickness of 20 nm on the TPD232 film. The film functions as a hole transporting layer. Further, H-1 as the host material was deposited from the vapor and formed into a film having a thickness of 40 nm. Simultaneously with this formation, Amine Compound D1 having a styryl described below, was deposited from the vapor in such a manner that a weight ratio between D1 and (H-1) would be 3:40. The film functions as a light emitting layer. Alq was formed into a film having a thickness of 10 nm on the resultant film. The film functions as an electron injecting layer. After that, Li serving as a reducing dopant (Li source: manufactured by SAES Getters) and Alq were subjected to co-deposition. Thus, an Alq:Li film (having a thickness of 10 nm) was formed as an electron injecting layer (cathode). Metal Al was deposited from the vapor onto the Alq:Li film to form a metal cathode. Thus, an organic EL device was formed.

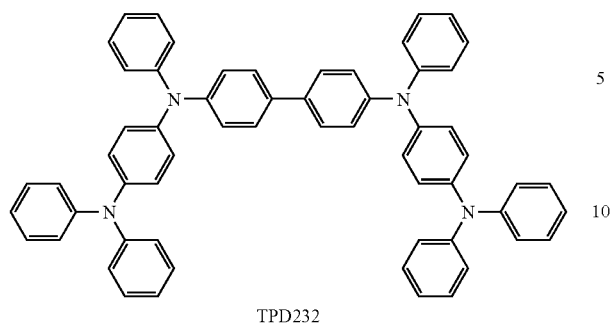

TPD232

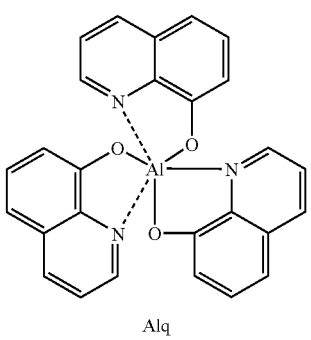

Alq

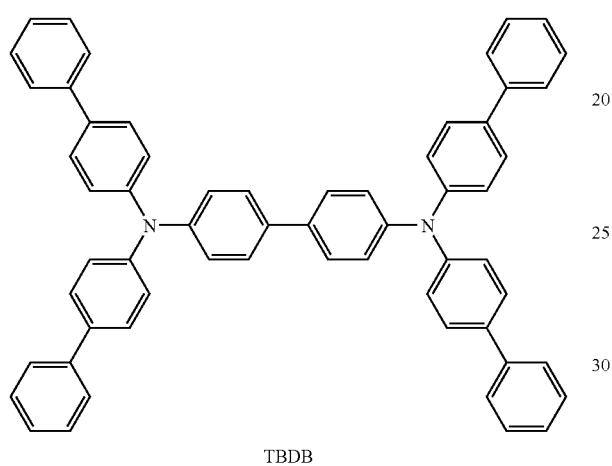

TBDB

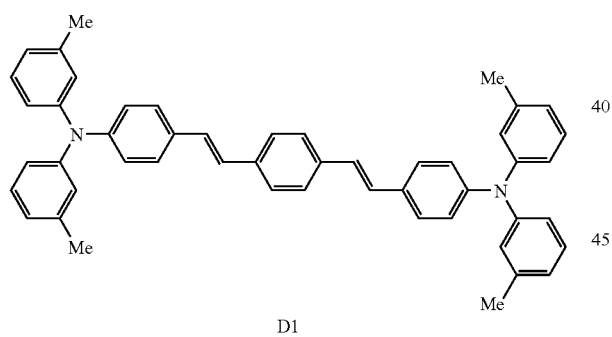

D1

Table 1 shows the results of the evaluation of the resultant organic EL device for the following items (1) and (2).

(1) Initial performance: A predetermined voltage was applied to the organic EL device, and a current value at the time of the application was measured. An emission luminance value and CIE1931 chromaticity coordinates were measured by a luminance meter (Spectroradiometer CS-1000, manufactured by Konica Minolta Sensing, Inc.) simultaneously with the measurement of the current value, followed by a calculation of current efficiency to evaluate the initial performance of the device.

(2) Lifetime: The organic EL device was driven at a constant current and initial luminance of 1,000 cd/m². The device was evaluated for its lifetime on the basis of the half time period of the luminance.

Example 2

Compound (H-2) was synthesized according to the following reaction formula.

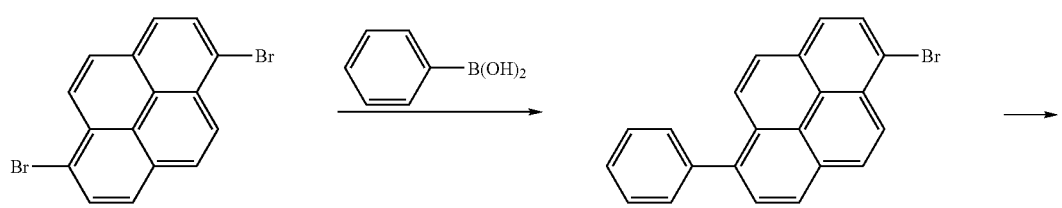

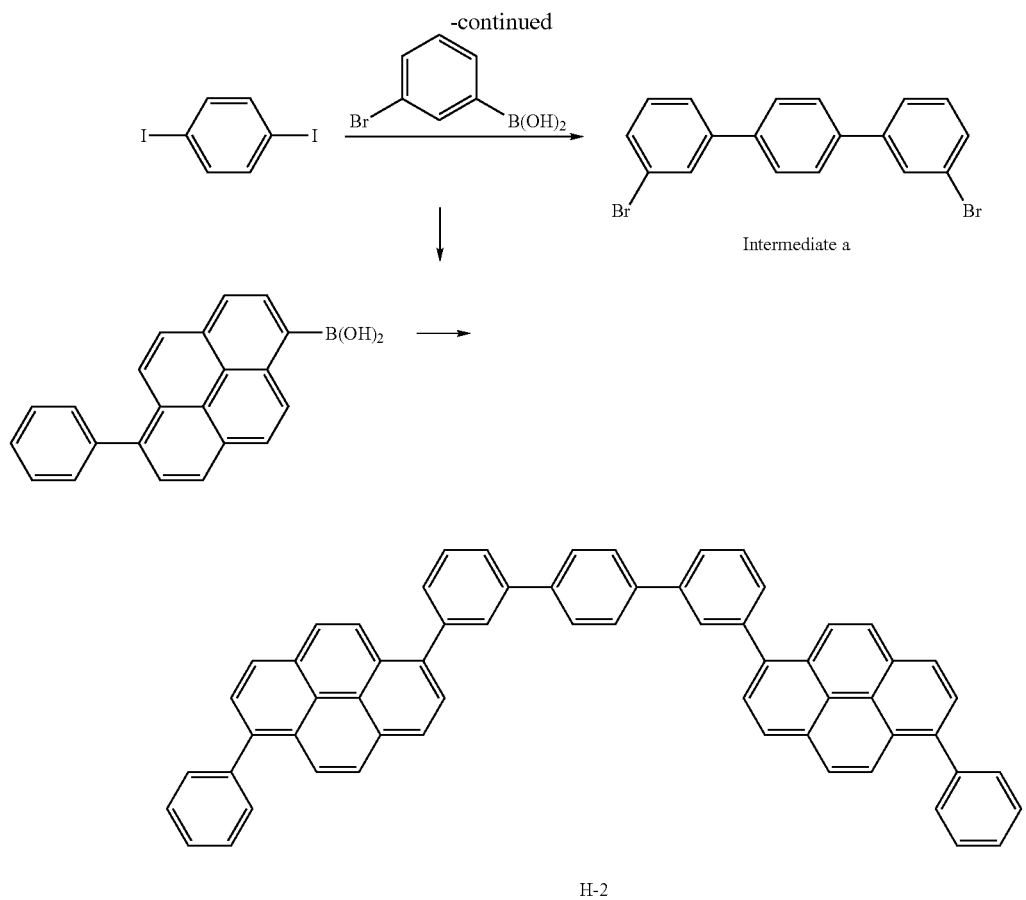

Intermediate a

H-2

8.03 g (40.0 mmol) of 3-bromophenylboronic acid, 6.93 g (21.0 mmol) of 1,4-diiodobenzene, and 0.92 g (0.8 mmol, 2 mol %) of tetrakis(triphenylphosphine)palladium(0) were loaded into a 300-ml three-necked flask, and air in the container was replaced with argon. Further, 60 ml of dimethoxyethane and 30 ml (3 eq) of a 2M aqueous solution of sodium carbonate were added to the mixture, and the whole was refluxed under heat in an oil bath at 90° C. for 8 hours. After one night, the resultant was extracted with toluene/ion-exchanged water and purified by column chromatography, whereby 6.33 g of Intermediate a were obtained (78% yield).

Next, 18.0 g (50.0 mmol) of 1,6-dibromopyrene, 6.10 g (50.0 mmol) of phenylboronic acid, and 1.16 g (1.0 mmol, 2 mol %) of tetrakis(triphenylphosphine)palladium(0) were loaded into a 300-ml three-necked flask, and air in the container was replaced with argon. Further, 150 ml of toluene and 75 ml (3 eq) of a 2M aqueous solution of sodium carbonate were added to the mixture, and the whole was refluxed under heat in an oil bath at 100° C. for 8 hours. After one night, the precipitate was separated by filtration, and the filtrate (toluene solution) was purified by column chromatography, whereby 11.6 g of 1-phenyl-6-bromopyrene were obtained (64.6% yield).

Next, 10.7 g (30.0 mmol) of 1-phenyl-6-bromopyrene obtained in the foregoing were dissolved in a mixed solvent of 100 ml of toluene and 50 ml of diethyl ether. Under an argon atmosphere at −70° C., 13.5 ml (36.0 mmol) of a (2.67M) solution of n-butyllithium in hexane were added to the solution, and the mixture was stirred for 1 hour while its temperature was changed from −70° C. to 0° C. Next, the reaction solution was cooled to −70° C., 20.6 ml (90 mmol) of triisopropyl borate were dropped to the reaction solution, and the mixture was stirred at −70° C. for 1 hour. After that, the temperature of the reaction solution was increased to room temperature, and the reaction solution was stirred for 6 hours. Further, 100 ml of 5% hydrochloric acid were dropped to the reaction solution, and the mixture was stirred at room temperature for 45 minutes. After the reaction solution had been separated into two layers, the organic layer was washed with a saturated salt solution and dried with anhydrous sodium sulfate. After the organic solvent had been removed by distillation under reduced pressure so as to have a volume about one fifth of its initial volume, the precipitated crystal was filtrated and sequentially washed with a mixed solvent of toluene and n-hexane and then with n-hexane, whereby 6.94 g of 1-phenylpyrene-6-boronic acid were obtained (72% yield).

Next, 1.94 g (5.0 mmol) of Intermediate a, 3.38 g (10.5 mmol) of 1-phenylpyrene-6-boronic acid, and 0.23 g (0.01 mmol, 2 mol %) of tetrakis(triphenylphosphine)palladium(0) were loaded into a 100-ml three-necked flask, and air in the container was replaced with argon. Further, 30 ml of toluene and 7.5 ml (3 eq) of a 2M aqueous solution of sodium carbonate were added to the mixture, and the whole was refluxed under heat in an oil bath at 100° C. for 8 hours. After one night, the precipitate was separated by filtration and washed with toluene, methanol, and ion-exchanged water, whereby 2.62 g of Compound (H-2) as a target product were obtained (67% yield).

Subsequently, a device was produced in the same manner as in Example 1 except that Compound (H-2) was used instead of Compound (H-1), and the device was evaluated for its performance. Table 1 shows the results.

FD-MS calcd for $C_{63}H_{46}$=783, found m/z=783 ($M^+$, 100)

Examples 3 to 7

Compounds (H-3) to (H-5) represented by the following structural formulae were each synthesized in the same manner as in Example 2 except that 2-naphthylboronic acid, 1-naphthylboronic acid, 4-biphenylboronic acid, 4-(1-naphthyl)phenylboronic acid, or 3-(2-naphthyl)phenylboronic acid was used instead of phenylboronic acid. A device was produced in the same manner as in Example 1 except that each of Compounds (H-3) to (H-5) was used instead of Compound (H-1), and the device was evaluated for its performance. Table 1 shows the results.

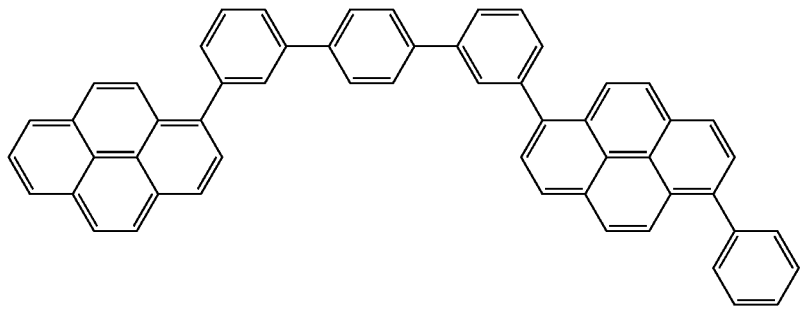

H-3

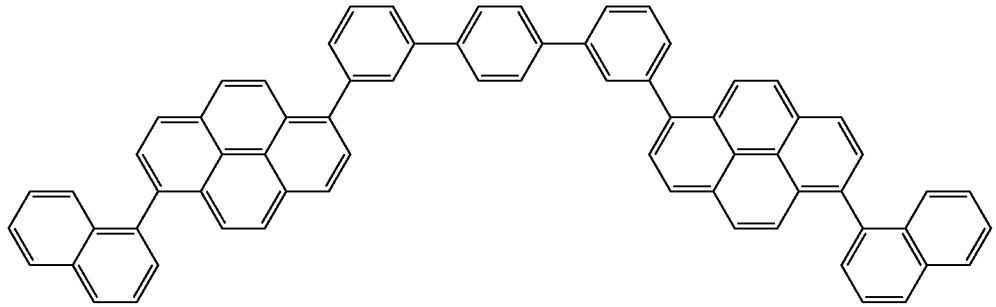

H-4

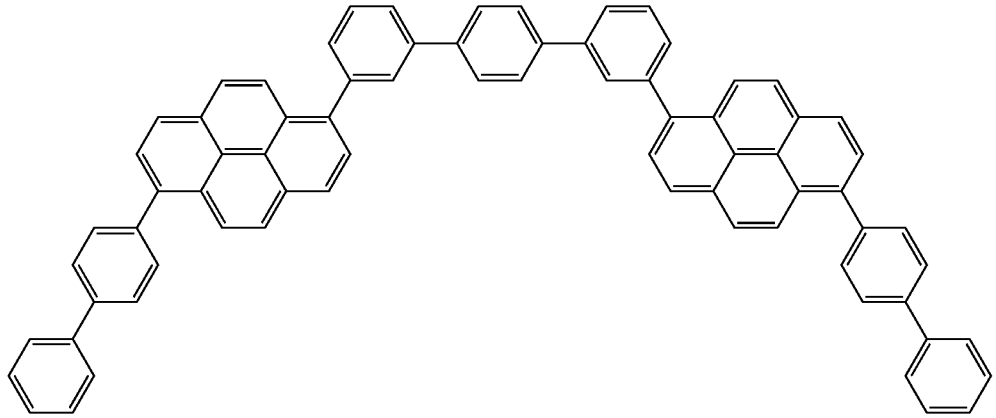

H-5

H-6
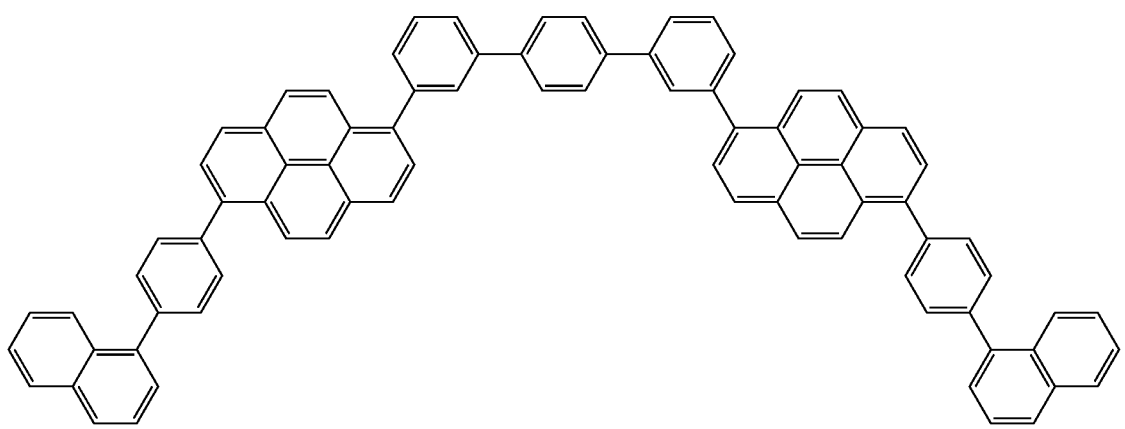
H-7
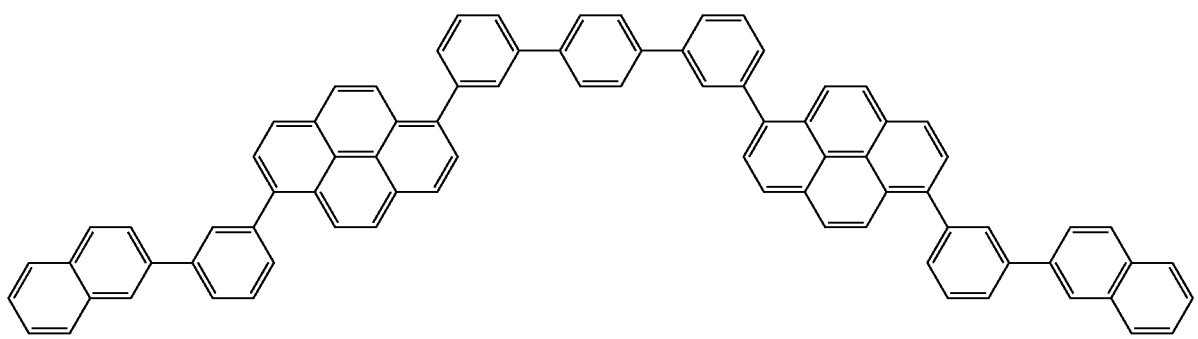
Example 8
First, Intermediate c was synthesized according to the following reaction formula.
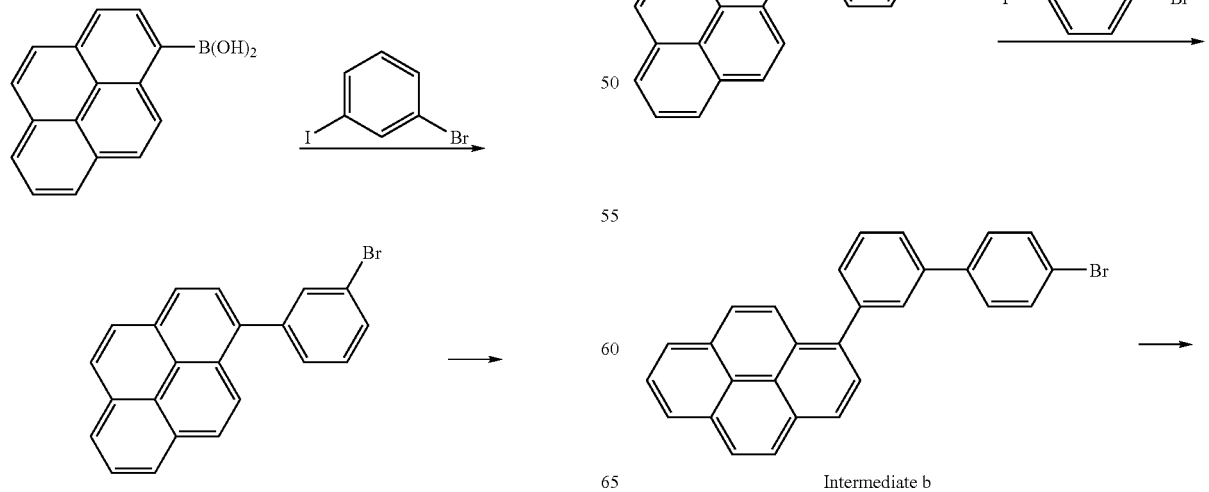
Intermediate b -continued

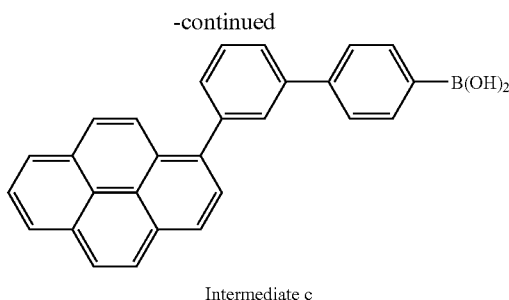

Intermediate c

Next, 6.44 g (20.0 mmol) of 3-pyrenylphenylboronic acid synthesized in the same manner as in Example 1, 5.94 g (21.0 mmol) of 4-bromoiodobenzene, and 0.46 g (0.4 mmol, 2 mol %) of tetrakis(triphenylphosphine)palladium(0) were loaded into a 300-ml three-necked flask, and air in the container was replaced with argon. Further, 60 ml of toluene and 30.0 ml (3 eq) of a 2M aqueous solution of sodium carbonate were added to the mixture, and the whole was refluxed under heat in an oil bath at 100° C. for 8 hours. After one night, the precipitate was separated by filtration and washed with toluene, methanol, and ion-exchanged water, whereby 7.62 g of Intermediate b as a target product were obtained (88% yield).

Next, 7.37 g (17.0 mmol) of Intermediate b obtained in the foregoing were dissolved in a mixed solvent of 50 ml of toluene and 50 ml of diethyl ether. Under an argon atmosphere at −70° C., 7.6 ml (20.4 mmol) of a (2.67M) solution of n-butyllithium in hexane were added to the solution, and the mixture was stirred for 1 hour while its temperature was changed from −70° C. to 0° C. Next, the reaction solution was cooled to −70° C., 11.7 ml (51 mmol) of triisopropyl borate were dropped to the reaction solution, and the mixture was stirred at −70° C. for 1 hour. After that, the temperature of the reaction solution was increased to room temperature, and the reaction solution was stirred for 6 hours. Further, 100 ml of 5% hydrochloric acid were dropped to the reaction solution, and the mixture was stirred at room temperature for 45 minutes. After the reaction solution had been separated into two layers, the organic layer was washed with a saturated salt solution and dried with anhydrous sodium sulfate. After the organic solvent had been removed by distillation under reduced pressure so as to have a volume about one fifth of its initial volume, the precipitated crystal was filtrated and sequentially washed with a mixed solvent of toluene and n-hexane and then with n-hexane, whereby 5.31 g of Intermediate c were obtained (78% yield).

Next, Intermediate d was synthesized according to the following reaction formula.

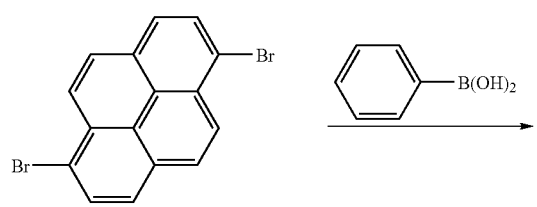

-continued

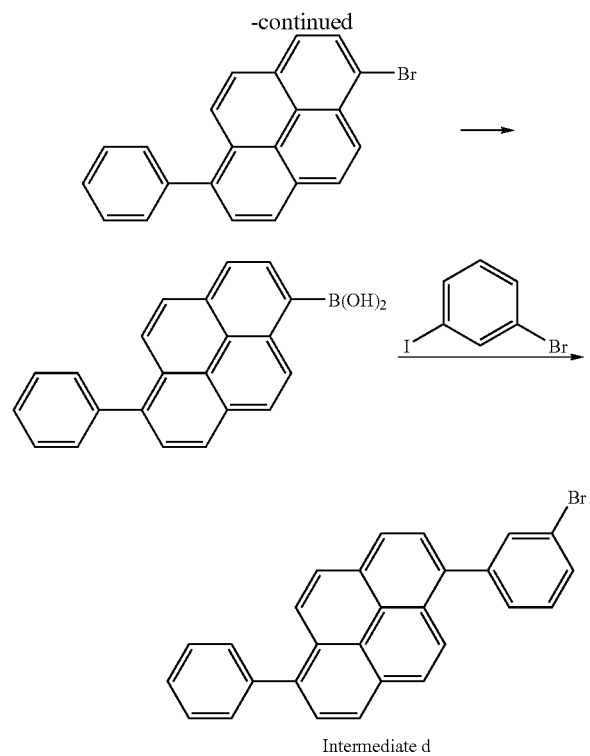

Intermediate d

Next, 3.22 g (10.0 mmol) of 1-phenylpyrene-6-boronic acid synthesized in the same manner as in Example 2, 2.97 g (10.5 mmol) of 3-bromoiodobenzene, and 0.23 g (0.2 mmol, 2 mol %) of tetrakis(triphenylphosphine)palladium(0) were loaded into a 300-ml three-necked flask, and air in the container was replaced with argon. Further, 30 ml of toluene and 15.0 ml (3 eq) of a 2M aqueous solution of sodium carbonate were added to the mixture, and the whole was refluxed under heat in an oil bath at 100° C. for 8 hours. After one night, the precipitate was separated by filtration and washed with toluene, methanol, and ion-exchanged water, whereby 3.55 g of Intermediate d as a target product were obtained (82% yield).

Finally, Compound (H-8) was synthesized by causing Intermediate c and Intermediated to react with each other as described below.

2.09 g (5.3 mmol) of Intermediate c, 2.17 g (5.0 mmol) of Intermediate d, and 0.12 g (0.1 mmol, 2 mol %) of tetrakis(triphenylphosphine)palladium(0) were loaded into a 100-ml three-necked flask, and air in the container was replaced with argon. Further, 15 ml of toluene and 7.5 ml (3 eq) of a 2M aqueous solution of sodium carbonate were added to the mixture, and the whole was refluxed under heat in an oil bath at 100° C. for 8 hours. After one night, the precipitate was separated by filtration and washed with toluene, methanol, and ion-exchanged water, whereby 2.79 g of Compound (H-8) as a target product were obtained (79% yield). Subsequently, a device was produced in the same manner as in Example 1 except that Compound (H-8) was used instead of Compound (H-1), and the device was evaluated for its performance. Table 1 shows the results.

FD-MS calcd for $C_{63}H_{46}$=708, found m/z=707 ($M^+$, 100)

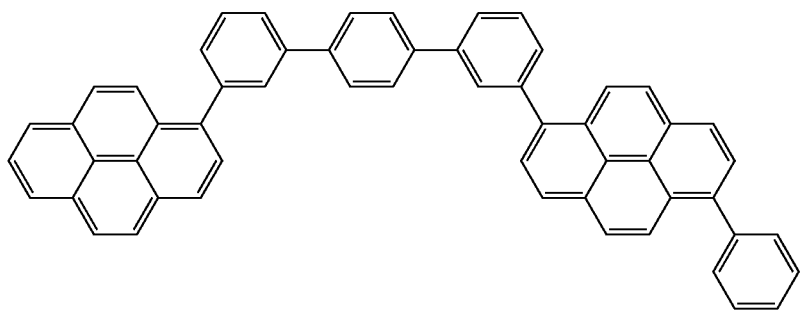

H-8

Examples 9 to 14

Compounds (H-9) to (H-14) were each synthesized in the same manner as in Example 8 except that: biphenylboronic acid, 2-naphthylboronic acid, 1-naphthylboronic acid, 4-(1-naphthyl)phenylboronic acid, 4-(2-naphthyl)phenylboronic acid, or 3-(2-naphthyl)boronic acid was used to synthesize a compound having the corresponding aryl group instead of the phenyl group of Intermediate d; and the synthesized compound was caused to react with Intermediate c. A device was produced from each of the compounds in the same manner as in Example 1, and was evaluated for its performance. Table 1 shows the results.

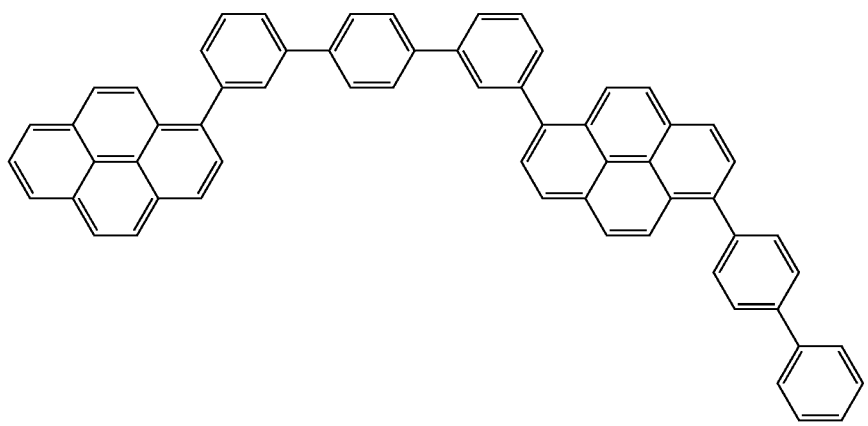

H-9

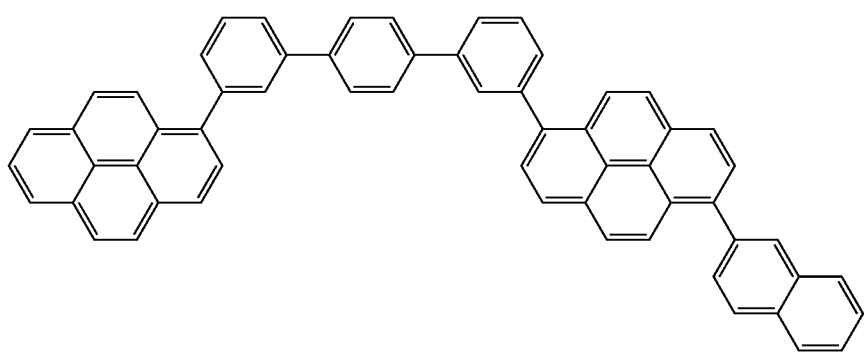

H-10

-continued
H-11
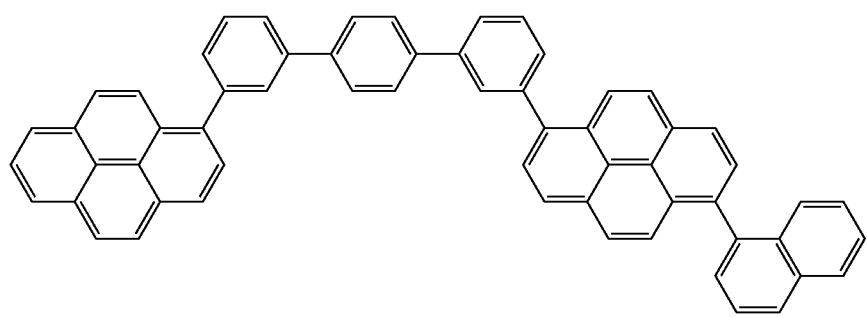
H-12
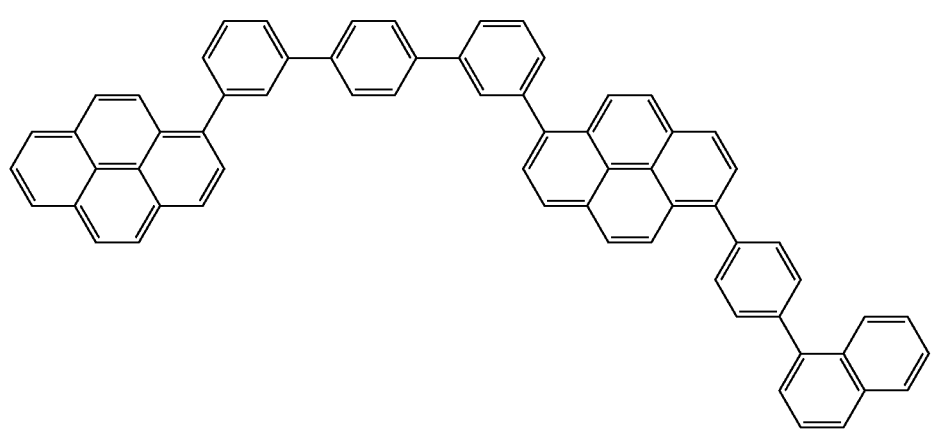
H-13
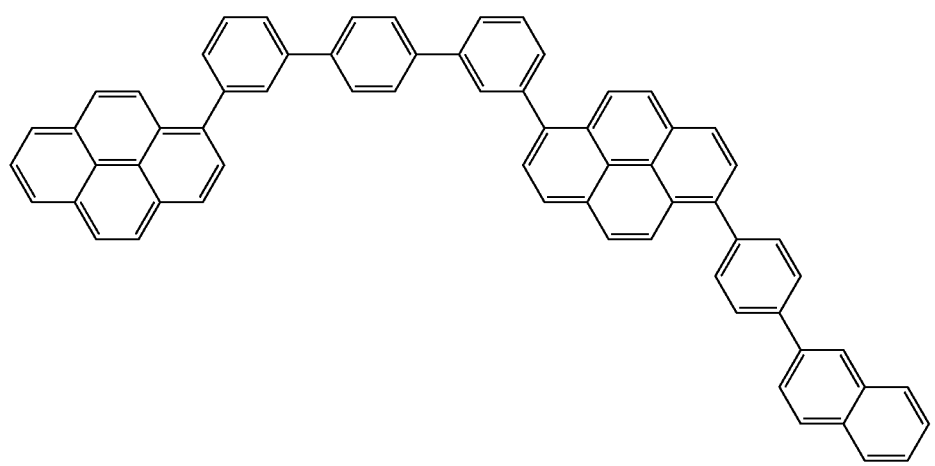
H-14
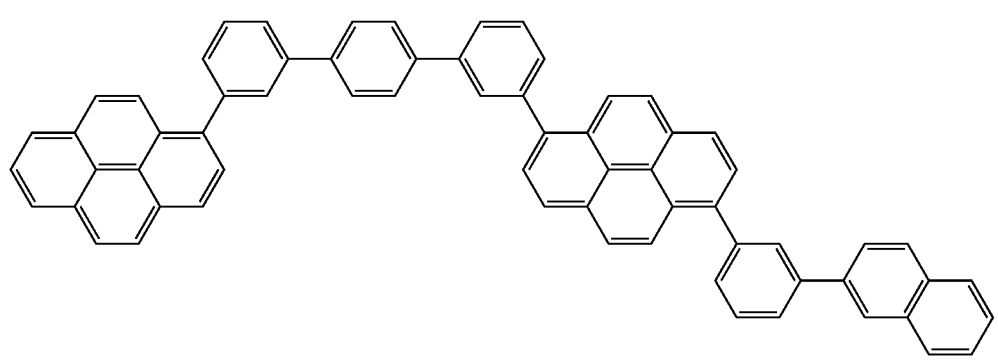

Examples 15 to 34
Compounds (H-15) to (H-34) having the following structures were synthesized by applying the synthesis methods in Examples 1 to 15 and investigating various raw materials. A device was produced from each of the compounds in the same manner as in Example 1, and was evaluated for its performance. Table 1 shows the results.
H-15
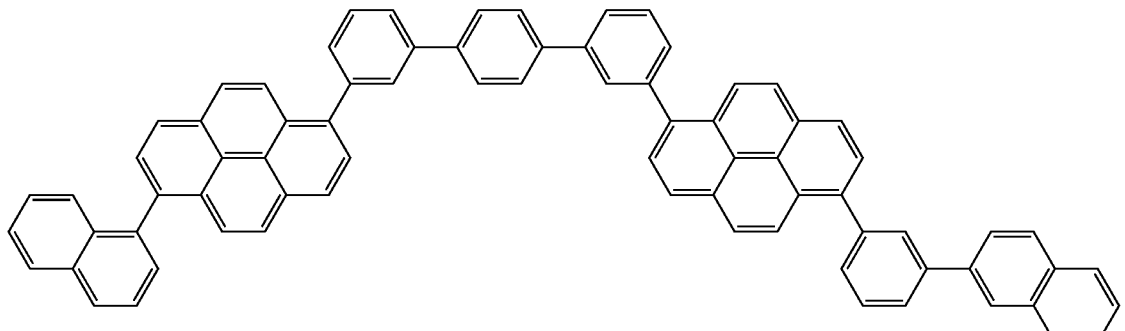
H-16
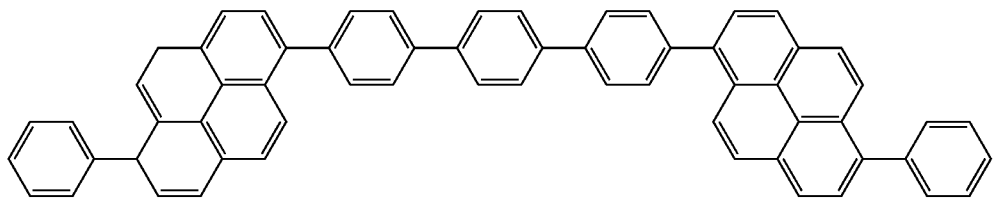
H-17
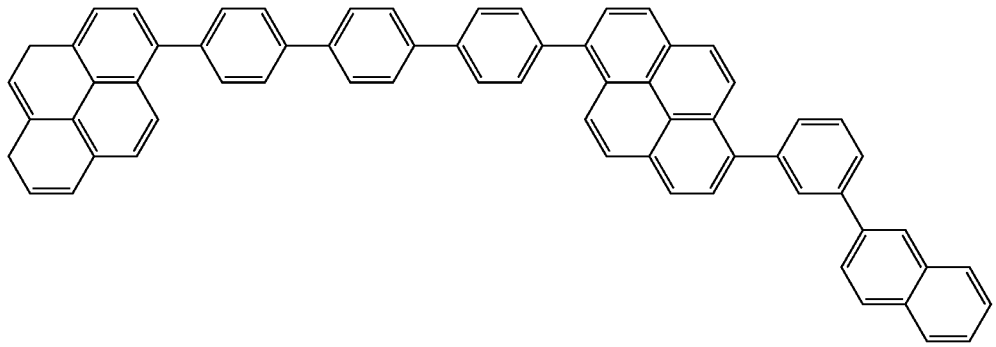
H-18
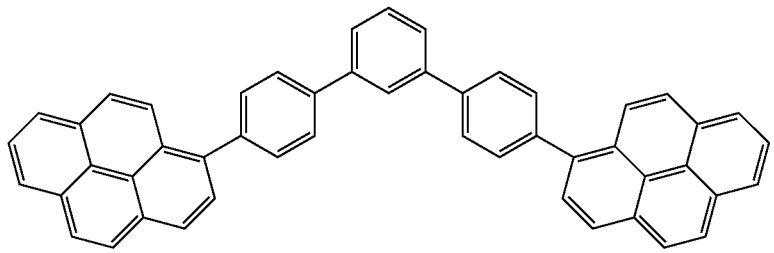
H-19
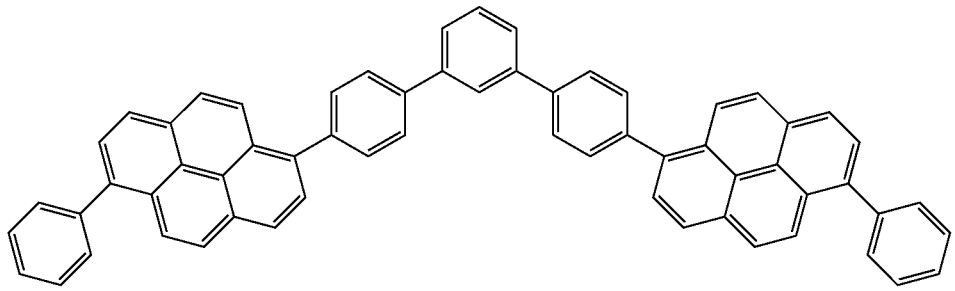

H-20
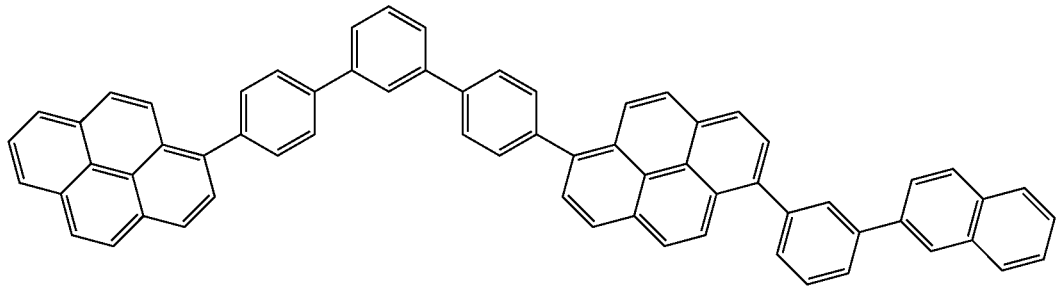
H-21
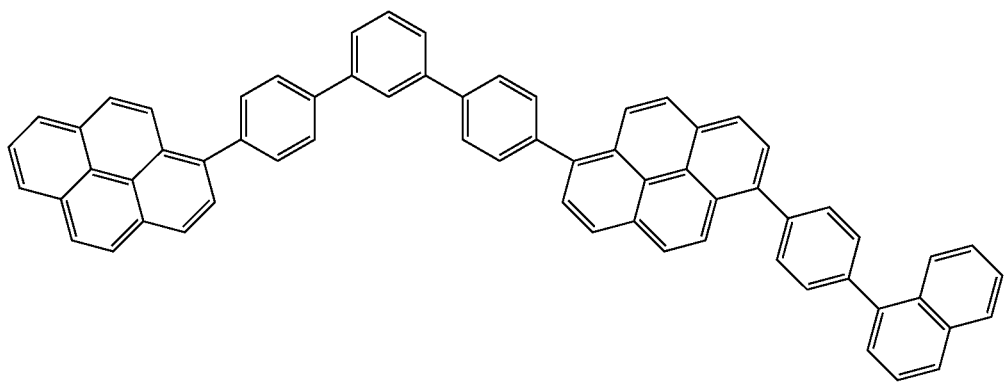
H-22
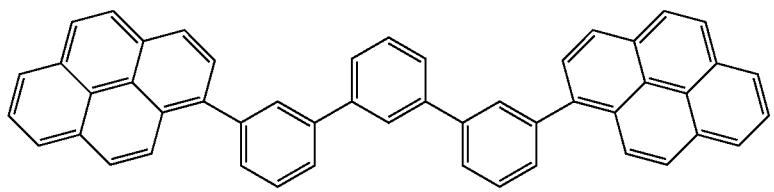
H-23
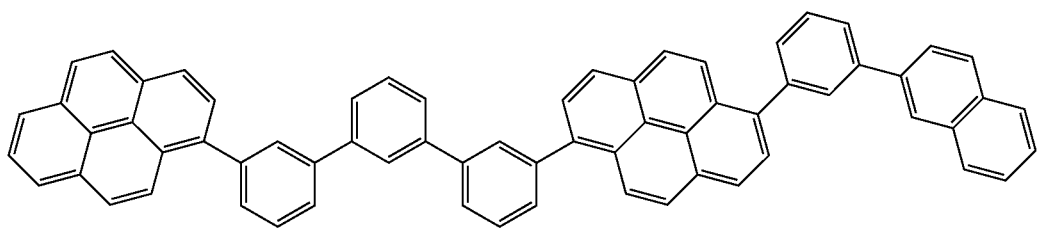
H-24
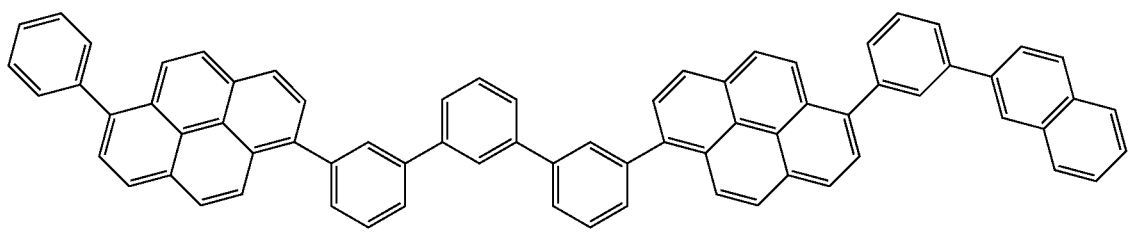

-continued
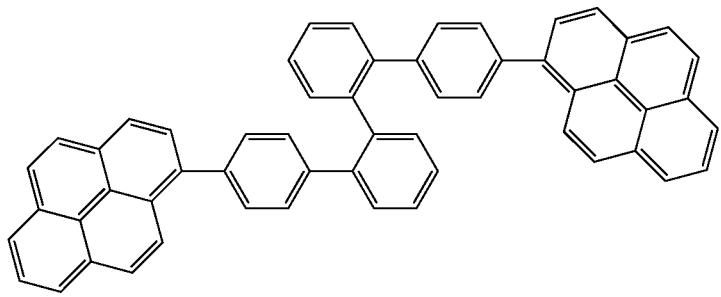
H-25
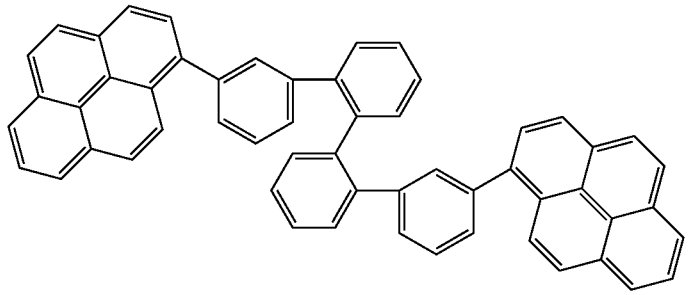
H-26
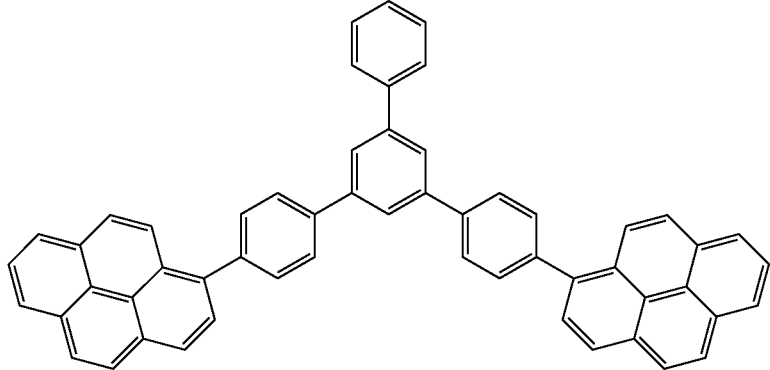
H-27
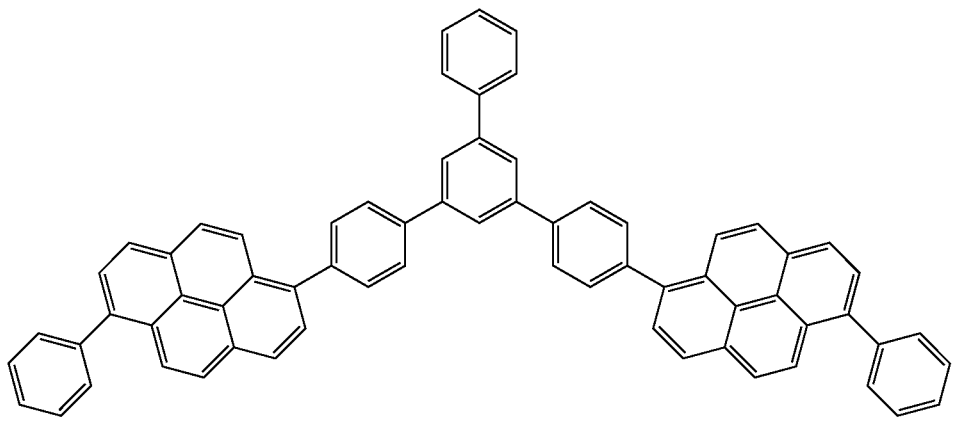
H-28

-continued
H-29
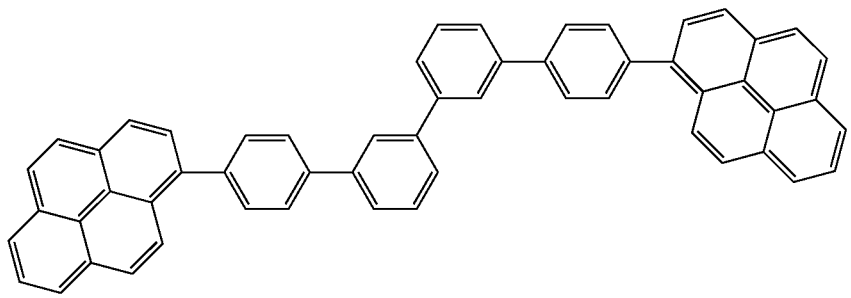
H-30
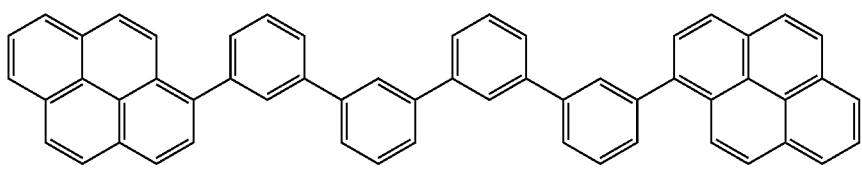
H-31
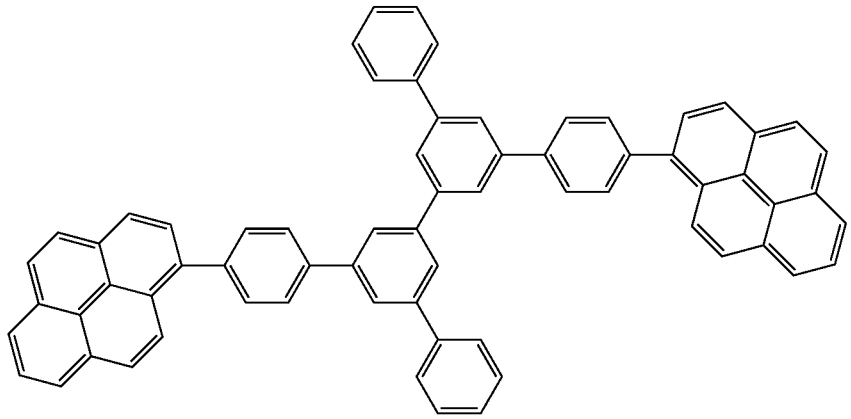
H-32
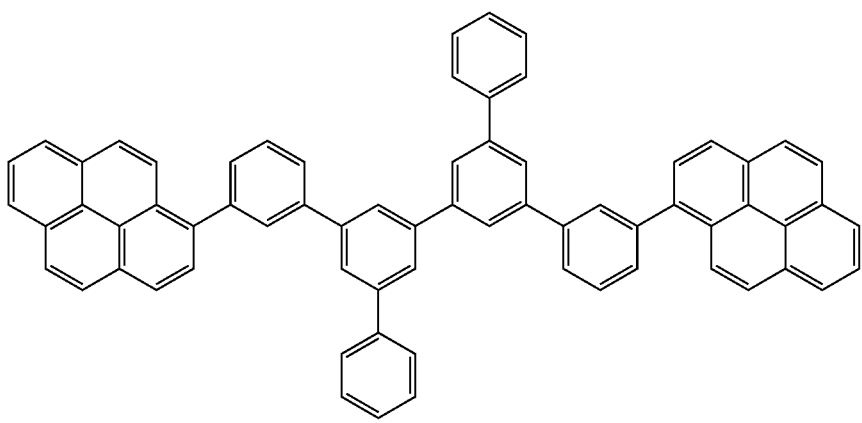
H-33
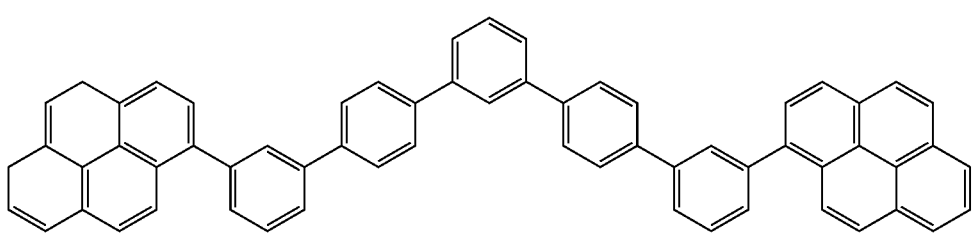

-continued

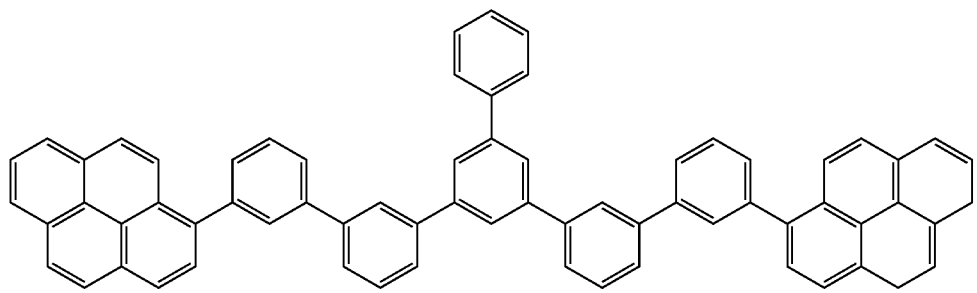

H-34

Comparative Examples 1 to 4

Comparative Compounds 1 to 4 were synthesized by the following reactions, and an organic EL device was produced in the same manner as in Example 1 except that each of the compounds was used instead of Compound (H-1). Table 1 shows the results of the evaluation of each of the devices.

TABLE 1

| | Light emitting material (host material) | Chromaticity (CIEx, CIEy) | Current efficiency (cd/A) | Luminance half life (hours) Initial 1000 cd/m² |
|---|---|---|---|---|
| Example 1 | H-1 | (0.14, 0.16) | 11.6 | 10250 |
| Example 2 | H-2 | (0.15, 0.17) | 10.9 | 8980 |
| Example 3 | H-3 | (0.15, 0.16) | 11.2 | 9740 |
| Example 4 | H-4 | (0.15, 0.17) | 11.1 | 8190 |
| Example 5 | H-5 | (0.16, 0.17) | 11.2 | 7760 |
| Example 6 | H-6 | (0.15, 0.18) | 10.7 | 7870 |
| Example 7 | H-7 | (0.14, 0.17) | 11.2 | 8860 |
| Example 8 | H-8 | (0.15, 0.18) | 10.7 | 8300 |
| Example 9 | H-9 | (0.16, 0.19) | 12.2 | 7860 |
| Example 10 | H-10 | (0.15, 0.18) | 10.7 | 8300 |
| Example 11 | H-11 | (0.16, 0.19) | 11.8 | 7680 |
| Example 12 | H-12 | (0.16, 0.18) | 10.9 | 8080 |
| Example 13 | H-13 | (0.16, 0.19) | 11.2 | 7590 |
| Example 14 | H-14 | (0.15, 0.18) | 10.9 | 7690 |
| Example 15 | H-15 | (0.15, 0.17) | 11.3 | 9220 |
| Example 16 | H-16 | (0.15, 0.18) | 11.0 | 9020 |
| Example 17 | H-17 | (0.15, 0.17) | 11.5 | 9050 |
| Example 18 | H-18 | (0.15, 0.18) | 11.2 | 8450 |
| Example 19 | H-19 | (0.16, 0.18) | 11.3 | 8340 |
| Example 20 | H-20 | (0.15, 0.17) | 10.8 | 9100 |
| Example 21 | H-21 | (0.14, 0.15) | 11.7 | 8960 |
| Example 22 | H-22 | (0.15, 0.16) | 11.2 | 8680 |
| Example 23 | H-23 | (0.16, 0.18) | 12.2 | 8500 |
| Example 24 | H-24 | (0.15, 0.17) | 11.9 | 8350 |
| Example 25 | H-25 | (0.14, 0.17) | 12.6 | 9300 |
| Example 26 | H-26 | (0.15, 0.18) | 12.0 | 9260 |
| Example 27 | H-27 | (0.14, 0.17) | 11.6 | 12300 |
| Example 28 | H-28 | (0.15, 0.18) | 12.0 | 11260 |
| Example 29 | H-29 | (0.16, 0.18) | 10.2 | 8800 |
| Example 30 | H-30 | (0.15, 0.17) | 11.7 | 9350 |
| Example 31 | H-31 | (0.14, 0.18) | 11.4 | 9370 |
| Example 32 | H-32 | (0.15, 0.19) | 12.0 | 9860 |
| Example 33 | H-33 | (0.14, 0.18) | 11.6 | 8900 |
| Example 34 | H-34 | (0.15, 0.18) | 12.0 | 9340 |

TABLE 1-continued

| Comparative Example 1 | Comparative Compound 1 | (0.17, 0.20) | 8.9 | 3530 |
|---|---|---|---|---|
| Comparative Example 2 | Comparative Compound 2 | (0.17, 0.22) | 6.5 | 4360 |
| Comparative Example 3 | Comparative Compound 3 | (0.26, 0.38) | 7.5 | — |
| Comparative Example 4 | Comparative Compound 4 | (0.17, 0.28) | 6.5 | 4490 |

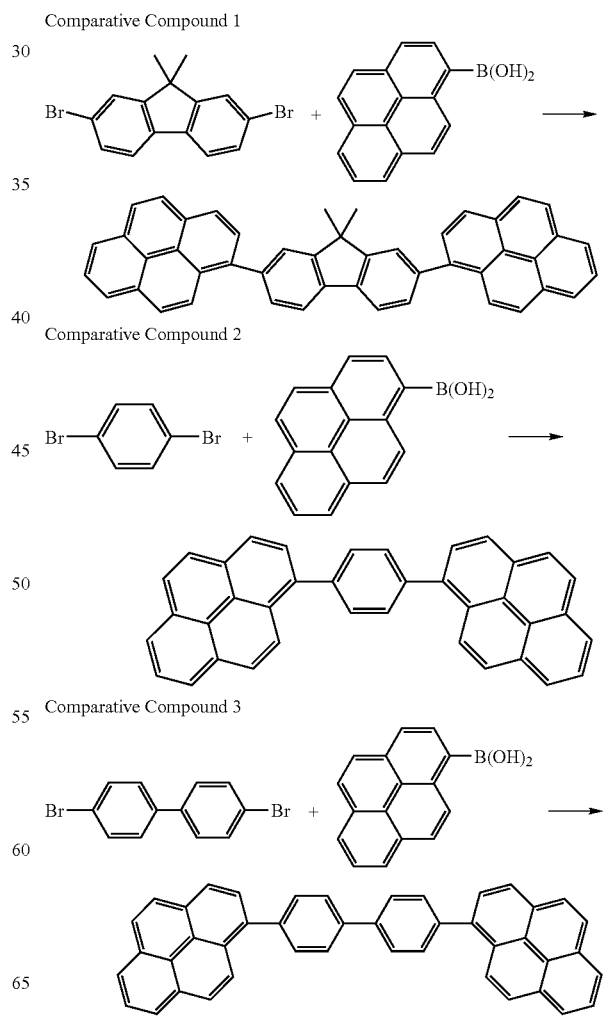

TABLE 1-continued

Comparative Compound 4

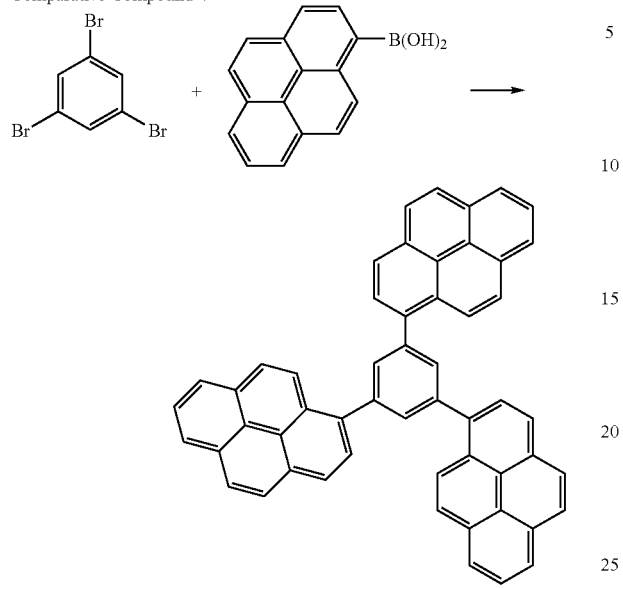

As described above, in the present invention, the formation of a light emitting layer from a material containing a bispyrenyl compound using a substituted or unsubstituted phenylene group having a specific structure as a linker lengthened the lifetime of an organic EL device having the light emitting layer as compared to that of an organic EL device using a conventional fluorene linker compound. In addition, the following was found: a bispyrene derivative or tripyrenylbenzene based on a phenylene or biphenylene group conventionally disclosed remarkably deteriorates the color purity of an organic EL device as described in each of Comparative Examples 2, 3, and 4, but the use of the bispyrene derivative based on a phenylene group having a specific structure of the present invention has significant effects by which the deterioration of the color purity of the device is prevented, and the efficiency and lifetime of the device are improved. The foregoing results have revealed that the bispyrenyl derivative using a phenylene group having a specific structure as a linker of the present invention is an extremely excellent light emitting material.

INDUSTRIAL APPLICABILITY

As described above in detail, the organic EL device using the pyrene derivative of the present invention can emit blue light with high luminous efficiency for a longtime period. Accordingly, the device is extremely useful as the organic EL device having high practicability.

The invention claimed is:

1. A pyrene derivative represented by the following general formula (1):

$$(A)_k\text{-}(X)_m\text{---}(Ar)_n\text{---}(Y)_p\text{---}(B)_q \qquad (1)$$

where:

X's each represent a substituted or unsubstituted pyrene residue;

A's and B's each independently represent a hydrogen atom, a substituted or unsubstituted aromatic hydrocarbon group having 3 to 50 ring carbon atoms, a substituted or unsubstituted aromatic heterocyclic group having 1 to 50 ring carbon atoms, a substituted or unsubstituted alkyl or alkylene group having 1 to 50 carbon atoms, or a substituted or unsubstituted alkenyl or alkenylene group having 1 to 50 carbon atoms;

Y's represent at least any one of a substituted or unsubstituted fused ring group having 5 to 50 ring carbon atoms and a fused heterocyclic group;

m is 1;

k and q each independently represent an integer of 0 to 4;

p is 1; and n is 1

Ar group in the general formula (1) is represented by one of the following structures, which is substituted by an alkyl group or not substituted:

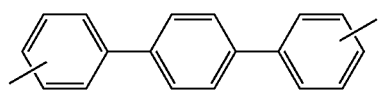

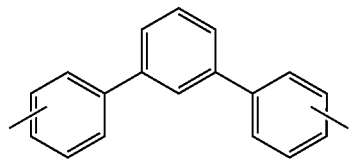

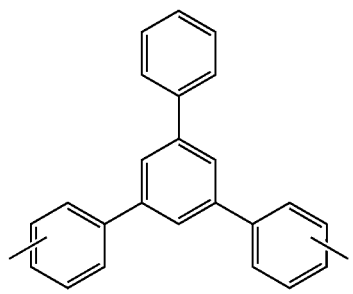

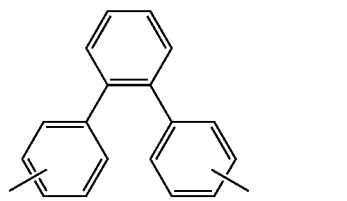

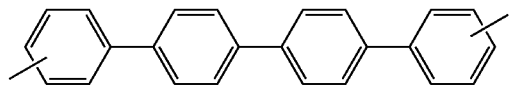

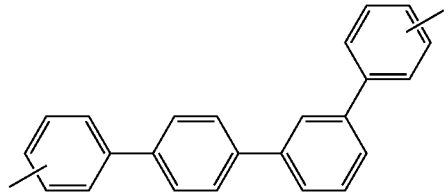

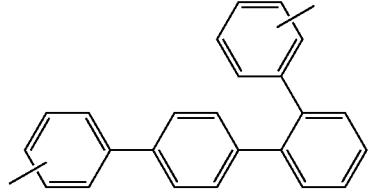

-continued
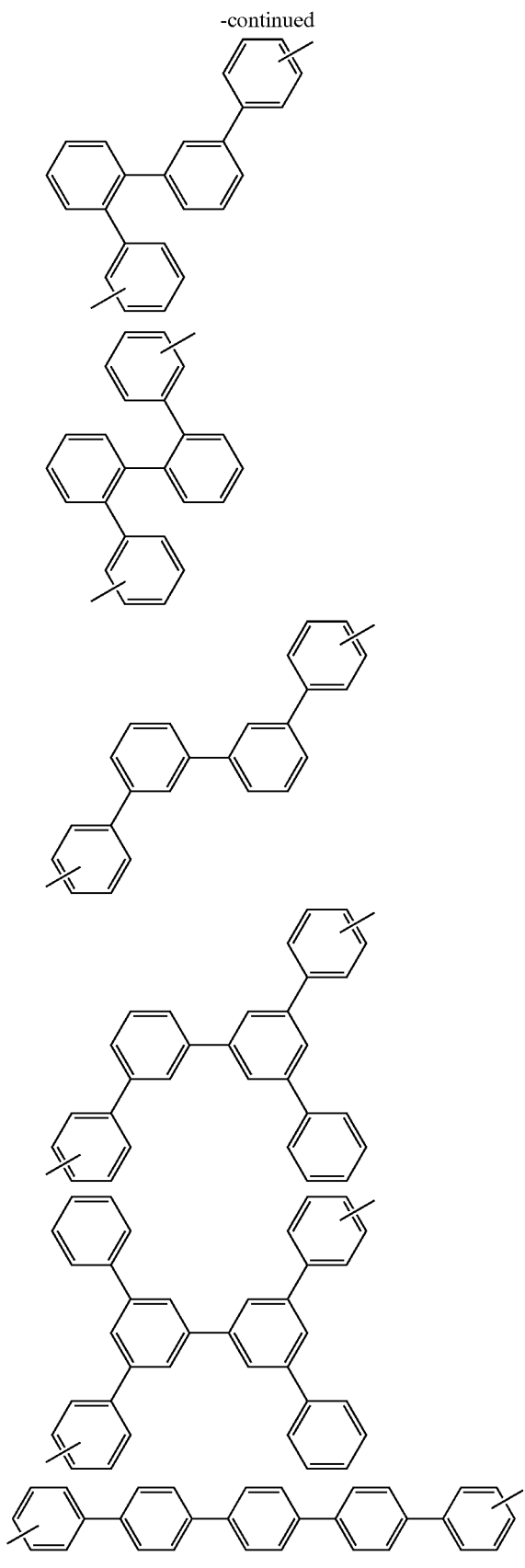
-continued
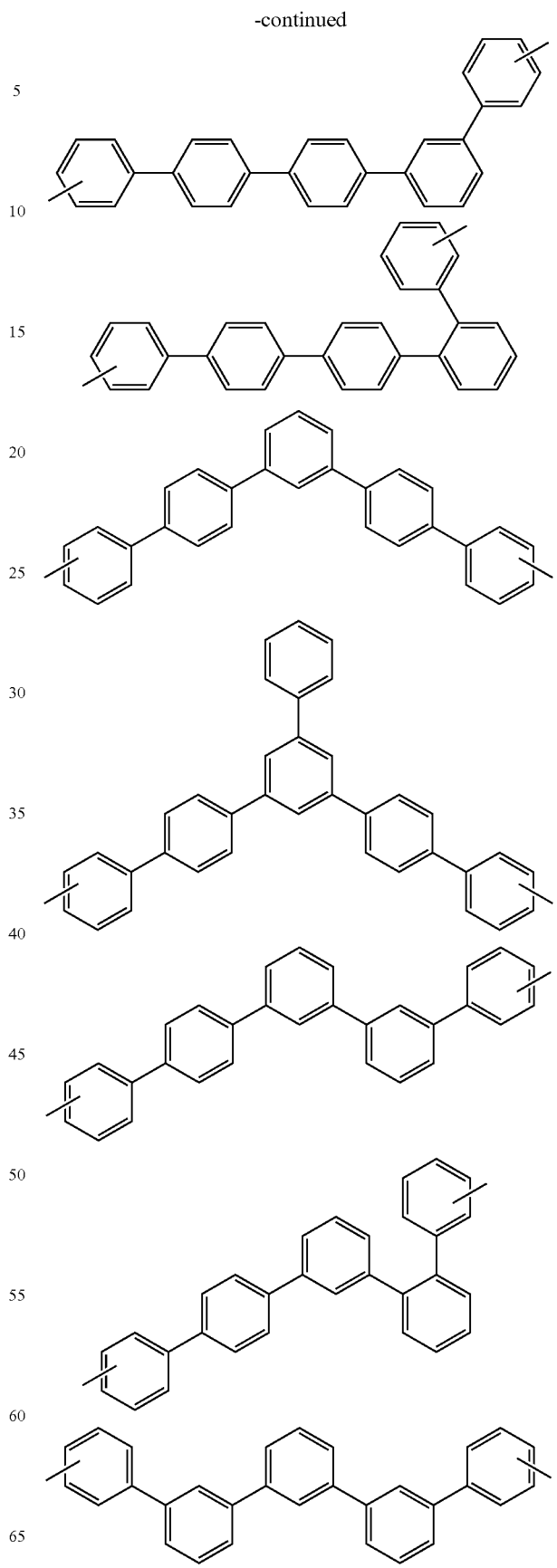

-continued
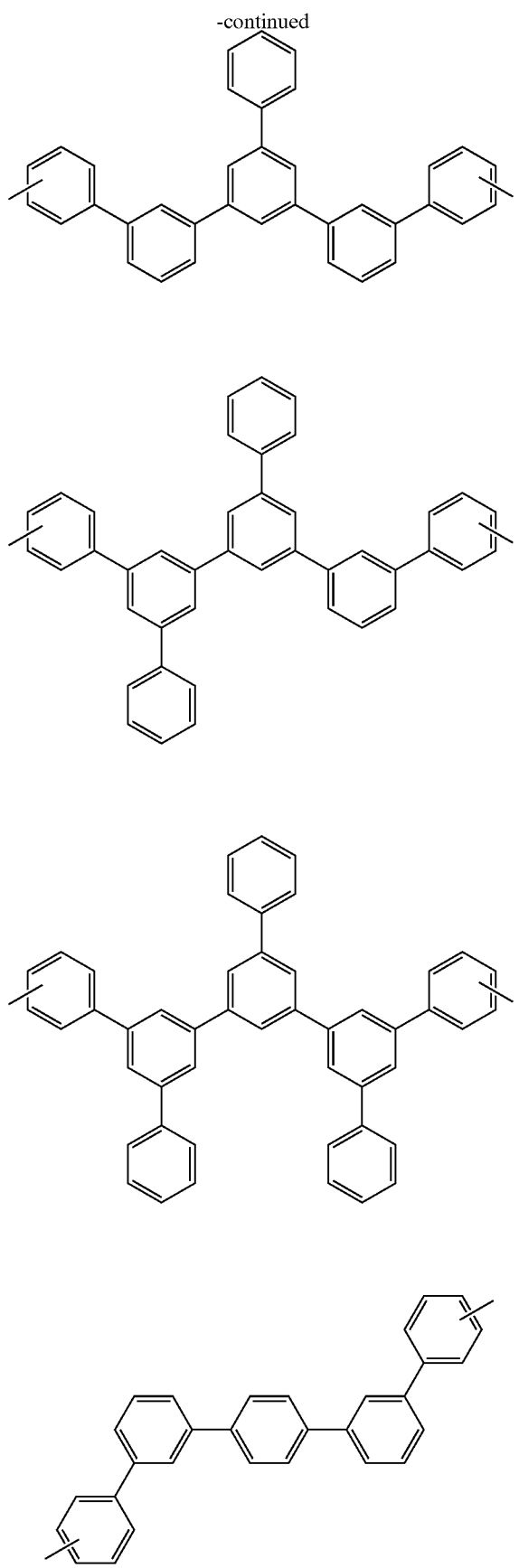
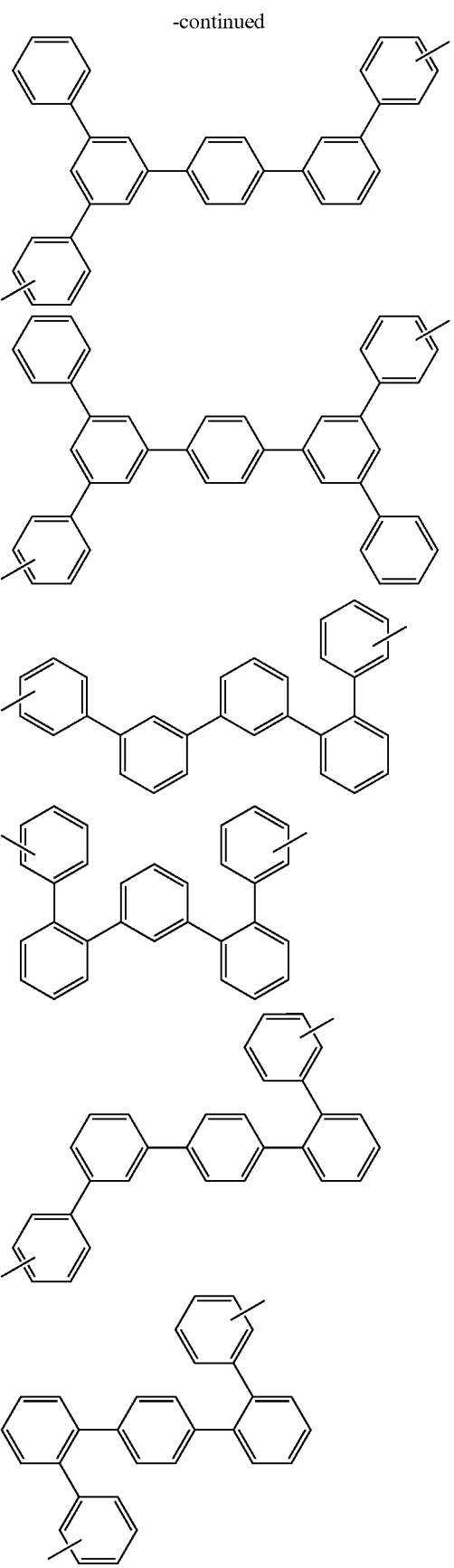

183
-continued
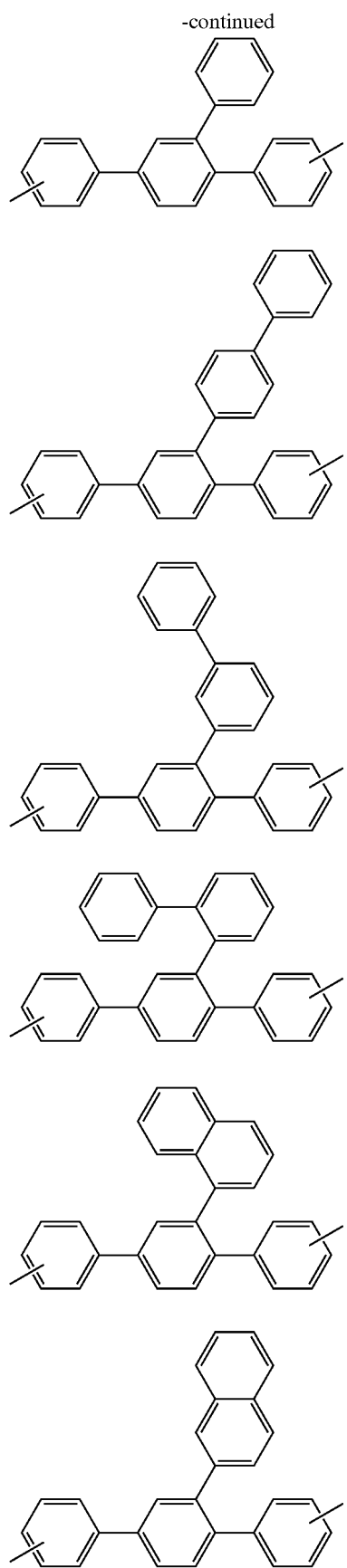
184
-continued
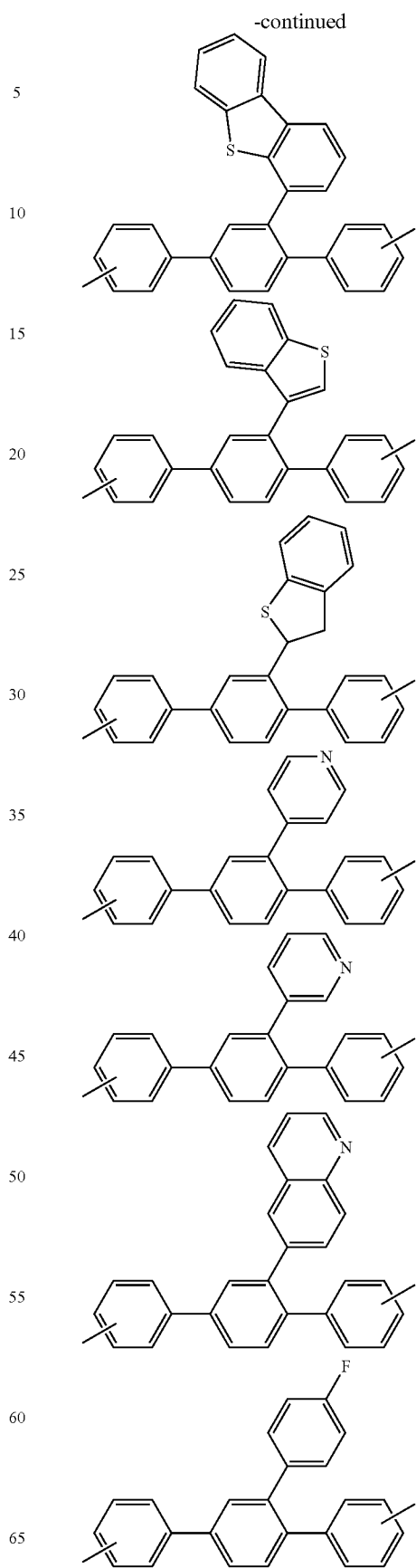

-continued
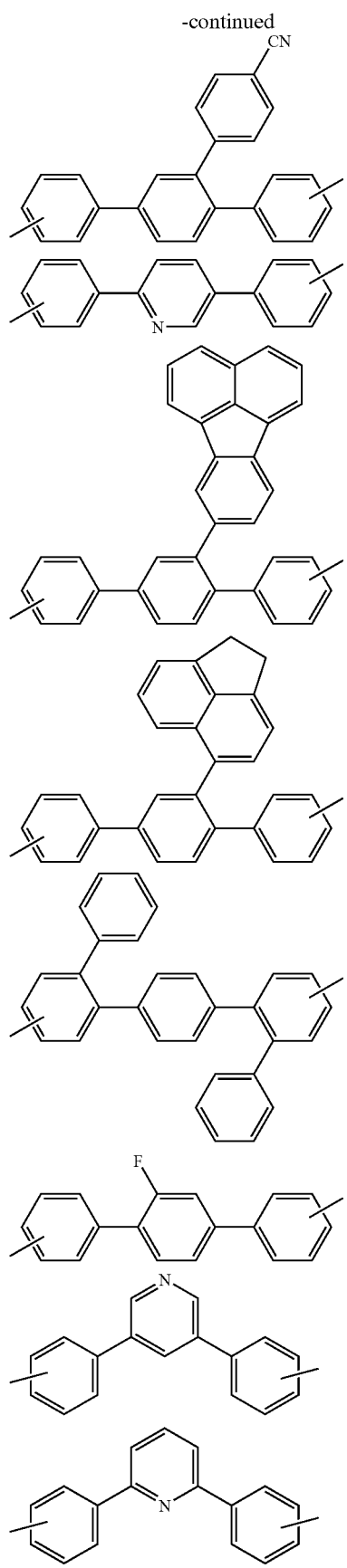
-continued
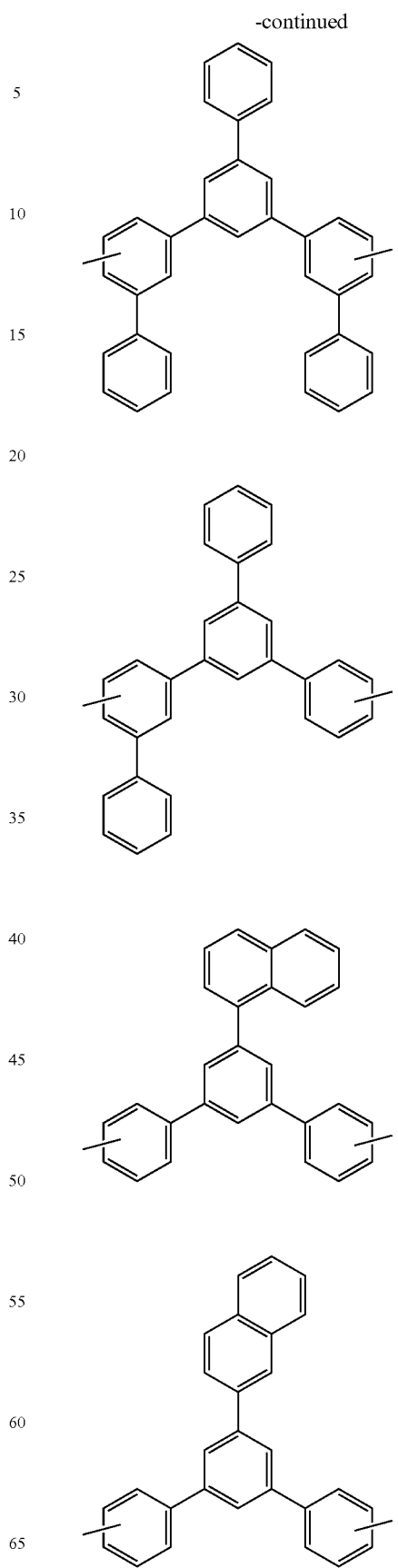

-continued

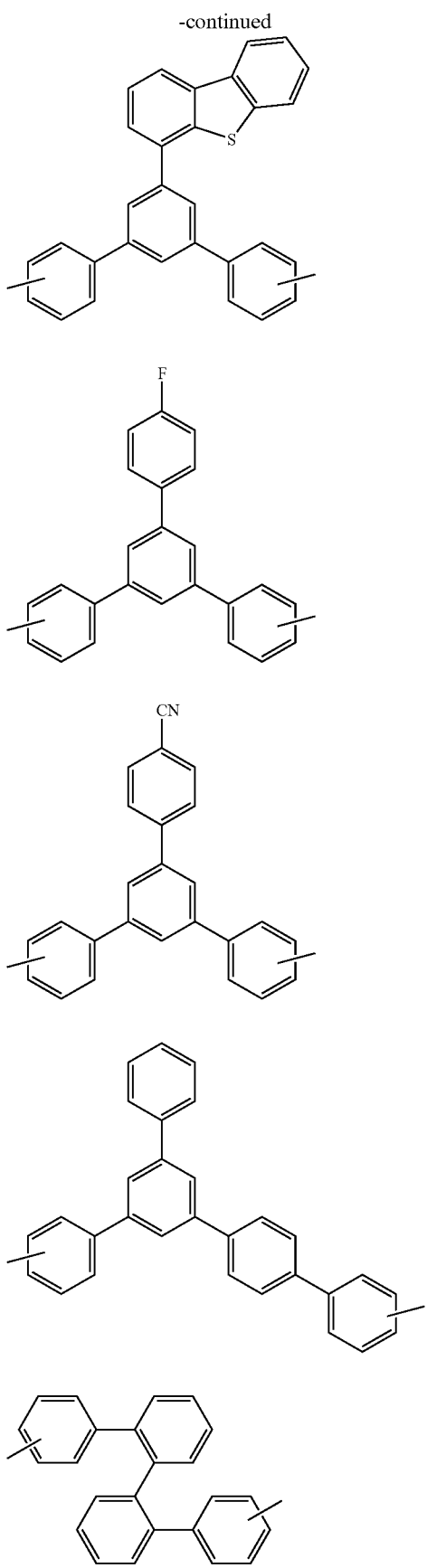
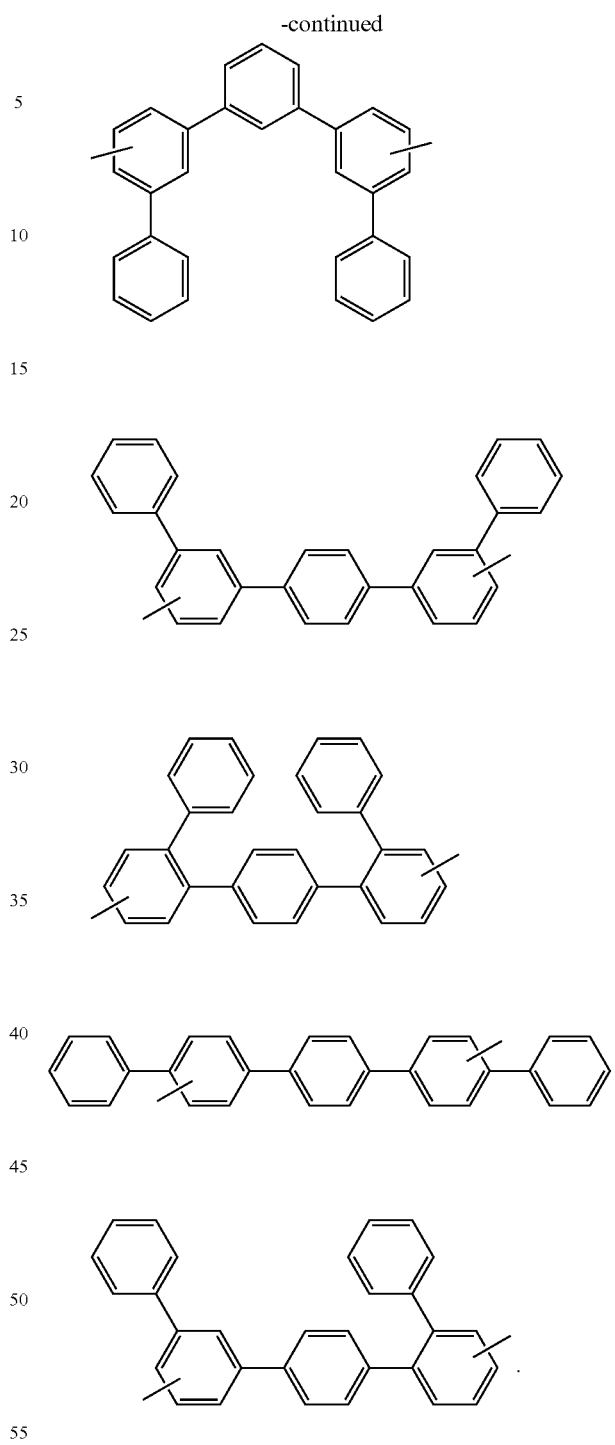

2. The pyrene derivative according to claim 1, wherein an Ar group in the general formula (1) is not substituted.

3. The pyrene derivative according to claim 1, wherein k+q≧1 in the general formula (1).

4. The pyrene derivative according to any one of claims 1, 2 and 3, wherein the pyrene derivative comprises a light emitting material for an organic electroluminescence device.

5. The pyrene derivative according to any one of claims 1, 2 and 3, wherein the pyrene derivative comprises a host material for an organic electroluminescence device.

6. An organic electroluminescence device, comprising an organic thin film layer formed of one or more layers including at least a light emitting layer, the organic thin film layer being interposed between a cathode and an anode, wherein at least one layer of the organic thin film layer contains the pyrene derivative according to any one of claims 1, 2 and 3 alone or as a component of a mixture.

7. The organic electroluminescence device according to claim 6, wherein the light emitting layer contains the pyrene derivative.

8. The organic electroluminescence device according to claim 7, wherein the light emitting layer further contains an arylamine compound.

9. The organic electroluminescence device according to claim 7, wherein the light emitting layer further contains a styrylamine compound.

10. The organic electroluminescence device according to claim 7, wherein the light emitting layer further contains a phosphorescent metal complex.

\* \* \* \* \*